United States Patent
Lobie et al.

(10) Patent No.: US 11,292,773 B2
(45) Date of Patent: Apr. 5, 2022

(54) SMALL MOLECULE INHIBITORS OF BCL-2-ASSOCIATED DEATH PROMOTER (BAD) PHOSPHORYLATION

(71) Applicants: NATIONAL UNIVERSITY OF SINGAPORE, Singapore (SG); UNIVERSITY OF MYSORE, Mysore (IN); BANGALORE UNIVERSITY, Bangalore (IN)

(72) Inventors: Peter Edward Lobie, Singapore (SG); Vijay Kumar Pandey, Singapore (SG); Rangappa Kanchugarakoppal Subbegowda, Mysore (IN); Bassappa Salundi, Bangalore (IN); Mohan Chakrabhavi Dhananjaya, Mysore (IN); Shobith Rangappa, Mysore (IN); Srinivasa Venkatachalaiah, Bangalore (IN)

(73) Assignees: NATIONAL UNIVERSITY OF SINGAPORE, Singapore (SG); UNIVERSITY OF MYSORE, Mysore (IN); BANGALORE UNIVERSITY, Bangalore (IN)

(*) Notice: Subject to any disclaimer, the term of this patent is extended or adjusted under 35 U.S.C. 154(b) by 0 days.

(21) Appl. No.: 16/605,630

(22) PCT Filed: Apr. 18, 2018

(86) PCT No.: PCT/SG2018/050194
§ 371 (c)(1),
(2) Date: Oct. 16, 2019

(87) PCT Pub. No.: WO2018/194520
PCT Pub. Date: Oct. 25, 2018

(65) Prior Publication Data
US 2020/0131139 A1   Apr. 30, 2020

(30) Foreign Application Priority Data
Apr. 19, 2017 (GB) .................................. 1706162

(51) Int. Cl.
| | |
|---|---|
| C07D 241/04 | (2006.01) |
| A61P 35/00 | (2006.01) |
| C07D 405/06 | (2006.01) |
| C07D 409/06 | (2006.01) |
| C07D 413/04 | (2006.01) |
| C07D 471/06 | (2006.01) |
| C07D 213/53 | (2006.01) |
| C07D 295/096 | (2006.01) |
| C07D 295/155 | (2006.01) |
| C07D 295/192 | (2006.01) |
| C07D 307/52 | (2006.01) |
| C07D 333/20 | (2006.01) |
| A61K 31/495 | (2006.01) |
| A61K 31/496 | (2006.01) |

(52) U.S. Cl.
CPC ............ *C07D 241/04* (2013.01); *A61P 35/00* (2018.01); *C07D 405/06* (2013.01); *C07D 409/06* (2013.01); *C07D 413/04* (2013.01); *C07D 471/06* (2013.01)

(58) Field of Classification Search
CPC .. C07D 241/04; C07D 405/06; C07D 409/06; C07D 413/04; C07D 471/06; C07D 333/20; C07D 295/096; C07D 295/155; C07D 295/192; C07D 213/53; C07D 307/52; A61P 35/00; A61K 31/495; A61K 31/496
See application file for complete search history.

(56) References Cited

U.S. PATENT DOCUMENTS

2020/0131139 A1*   4/2020   Lobie ...................... A61P 35/00

FOREIGN PATENT DOCUMENTS

| JP | 2017128541 A | 7/2017 |
| WO | WO-01/07050 A1 | 2/2001 |

OTHER PUBLICATIONS

Neto, Í.,"Multicomponent Petasis-borono Mannich preparation of alkylaminophenols and antimicrobial activity studies." ChemMedChem 11.18 (2016): 2015-2023.*
Chemical Abstracts Service CAS Registry No. 1797320-83-2, CAplus database entry date of Jul. 8, 2015 (see below) and the compound represented by Chemical Abstracts Service CAS Registry No. 1088182-85-7, CAplus database entry date of Dec. 22, 2008. p. 1.*
Tabassum, S., "Sonochemistry—an innovative opportunity towards a one-pot three-component synthesis of novel pyridylpiperazine derivatives catalysed by meglumine in water." New Journal of Chemistry 41.9 (2017): 3515-3523.*

(Continued)

*Primary Examiner* — John M Mauro
(74) *Attorney, Agent, or Firm* — Marshall, Gerstein & Borun LLP

(57) ABSTRACT

The invention relates to compounds of general formula (I): wherein $R^1$, n, $R^{2a}$, $R^{2b}$, and $R^3$ are as defined herein. The compounds are inhibitors of Bcl-2-associated death promoter (BAD) phosphorylation and have anti-apoptotic activity and are useful in the treatment of cancer, particularly breast cancer, endometrial cancer, ovarian cancer, liver cancer, colon cancer, prostate cancer or pancreatic cancer.

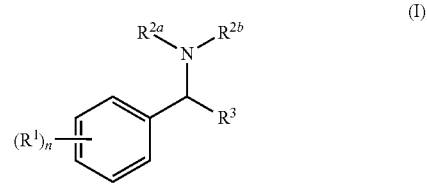

18 Claims, 33 Drawing Sheets

(56) References Cited

OTHER PUBLICATIONS

Erb, W.,"Sequential One-Pot Access to Molecular Diversity through Aniline Aqueous Borylation." The Journal of organic chemistry 79.21 (2014): 10568-10580.*

Ambrosini et al., A novel anti-apoptosis gene, survivin, expressed in cancer and lymphoma. Nat. Med. 1997; 3(8):917-921.

Anderson et al., Targeting BCL2 for the treatment of lymphoid malignancies. Semin. Hematol. 2014; 51(3):219-227.

Anilkumar et al., Anti-apoptotic BCL-2 family proteins in acute neural injury. Front. Cell Neurosci. 2014; 8:281.

Boisvert-Adamo et al., Mutant B-RAF mediates resistance to anoikis via Bad and Bim. Oncogene. 2008; 27(23):3301-3312.

Bruncko et al., Studies leading to potent, dual inhibitors of Bcl-2 and Bcl-xL. J. Med. Chem. 2007; 50(4):641-662.

Christov et al., Short-term modulation of cell proliferation and apoptosis and preventive/therapeutic efficacy of various agents in a mammary cancer model, Clin. Cancer Res., 13(18 Pt 1):5488-96 (Sep. 2007).

Czabotar et al., Bcl-2 family proteins as therapeutic targets. Curr. Pharm. Design. 2010; 16(28):3132-3148.

Datta et al., Cellular survival: a play in three Akts. Genes Dev. 1999; 13(22):2905-2927.

Doerflinger et al., BH3-only proteins: A 20-year stock-take. FEBS J. 2015. 282(6):1006-16.

Fang et al., Regulation of BAD phosphorylation at serine 112 by the Ras-mitogen-activated protein kinase pathway. Oncogene. 1999; 18(48):6635-6640.

Harada et al., Phosphorylation and inactivation of BAD by mitochondria-anchored protein kinase A. Mol. Cell. 1999; 3(4):413-422.

Hardwick et al., Multiple functions of BCL-2 family proteins. Cold Spring Harb. Perspect. Biol. 2013; 5(2).

Hayakawa et al., Inhibition of BAD phosphorylation either at serine 112 via extracellular signal-regulated protein kinase cascade or at serine 136 via Akt cascade sensitizes human ovarian cancer cells to cisplatin. Cancer Res. 2000; 60(21):5988-5994.

Hosseinzadeh et al., A green protocol for the one-pot multicomponent Petasis boronic Mannich reaction using ball milling, J. Iran Chem. Soc., 14(2):347-55 (Oct. 2016).

Hutt, The role of BH3-only proteins in apoptosis within the ovary. Reproduction (Cambridge, England). 2015; 149(2):R81-R89.

International Application No. PCT/SG2018/050194, International Preliminary Report on Patentability, dated Oct. 22, 2019.

International Application No. PCT/SG2018/050194, International Search Report and Written Opinion, dated Jul. 4, 2018.

Jiang et al., The Bad guy cooperates with good cop p53: Bad is transcriptionally up-regulated by p53 and forms a Bad/p53 complex at the mitochondria to induce apoptosis. Mol. Cell Biol. 2006; 26(23):9071-82.

Kanamori et al., Correlation between loss of PTEN expression and Akt phosphorylation in endometrial carcinoma. Clin. Cancer Res. 2001; 7(4):892-895.

Karube et al., Comprehensive gene expression profiles of NK cell neoplasms identify vorinostat as an effective drug candidate, Cancer Lett., 333(1):47-55 (Jun. 2013).

Keerthy et al., Novel synthetic biscoumarins target tumor necrosis factor-? in hepatocellular carcinoma in vitro and in vivo. J. Biol. Chem. 2014; 289(46):31879-90.

Keerthy et al., Synthesis and characterization of novel 2-amino-chromene-nitriles that target Bcl-2 in acute myeloid leukemia cell lines. PloS One. 2014; 9(9):e107118.

Krautwald et al., Effective blockage of both the extrinsic and intrinsic pathways of apoptosis in mice by TAT-crmA. J. Biol. Chem. 2010; 285(26):19997-20005.

Lin et al., Induction of apoptosis and cell-cycle arrest in human colon cancer cells by meclizine, Food Chem. Toxicol., 45(6):935-44 (Dec. 2006).

Macdonald et al., Pim kinases phosphorylate multiple sites on Bad and promote 14-3-3 binding and dissociation from Bcl-XL. BMC Cell Biol. 2006; 7:1.

Marchion et al. BAD phosphorylation determines ovarian cancer chemosensitivity and patient survival. Clin. Cancer Res. 2011; 17(19):6356-6366.

Masters et al., 14-3-3 inhibits Bad-induced cell death through interaction with serine-136. Mol. Pharm. 2001; 60(6):1325-1331.

Oltersdorf et al., An inhibitor of Bcl-2 family proteins induces regression of solid tumours. Nature. 2005; 435(7042):677-681.

Pandey et al. Trefoil factor 3 promotes metastatic seeding and predicts poor survival outcome of patients with mammary carcinoma. Breast Cancer Res. 2014;16(5):429.

Petros et al., Rationale for Bcl-xL/Bad peptide complex formation from structure, mutagenesis, and biophysical studies. Protein Sci. 2000; 9(12):2528-2534.

Rakesh et al., A New Ibuprofen Derivative Inhibits Platelet Aggregation and ROS Mediated Platelet Apoptosis. PloS one. 2014; 9(9):e107182.

Richard et al., Hydroxyquinoline-derived compounds and analoguing of selective Mcl-1 inhibitors using a functional biomarker, Bioorg. Med. Chem., 21(21):6642-9 (Nov. 2013).

Riedl et al., Molecular mechanisms of caspase regulation during apoptosis. Nat Rev Mol Cell Biol. 2004; 5(11):897-907.

Sastry et al., Targeting proapoptotic protein BAD inhibits survival and self-renewal of cancer stem cells. Cell Death Differentiation. 2014; 21(12):1936-1949.

Seow et al., Immunohistochemical detection of phospho-Akt, phospho-BAD, HER2 and oestrogen receptors alpha and beta in Malaysian breast cancer patients. Pathol. Oncol. Res. 2010; 16(2):239-248.

Smith et al., Expression of the Bcl-2 protein BAD promotes prostate cancer growth. PloS One. 2009; 4(7):e6224.

Thakran et al., Synthesis and pharmacological evaluation of 1-benhydryl piperazine derivatives, Int. J. Pharm. Sci. Res., 3(1):213-217 (Jan. 2012).

Wang et al. Trefoil factor 3 as a novel biomarker to distinguish between adenocarcinoma and squamous cell carcinoma. Medicine (Baltimore). 2015;94(20):e860.

You et al. Trefoil factor 3 mediation of oncogenicity and chemoresistance in hepatocellular carcinoma is AKT-BCL-2 dependent. Oncotarget, 8(24):39323-39344 (2017).

* cited by examiner

Figure 11

IC$_{50}$ values of NPB in a range of carcinoma cell lines

| Panel of cell lines | | NPB (µM) | |
|---|---|---|---|
| Tissue | Cells | IC$_{50}$^ | ±SD |
| Mammary | #MCF10A | NV | NV |
| | #MCF12A | NV | NV |
| | MCF7 | 6.5 | 1.06 |
| | T47D | 7.24 | 1.91 |
| | BT474 | 5.31 | 2.04 |
| | BT549 | 4.88 | 1.31 |
| | MDA-MB-231 | 6.94 | 1.86 |
| Endometrial | Ishikawa | 7.51 | 2.08 |
| | ECC1 | 2.61 | 0.97 |
| | RL95-2 | 6.38 | 1.85 |
| | AN3 | 11.37 | 2.61 |
| Ovarian | SK-OV-3 | 7.34 | 2.03 |
| | OVCAR-2 | 4.21 | 1.74 |
| | Caov-3 | 3.95 | 0.93 |
| | HEY C2 | 6.82 | 1.94 |
| | Ovca433 | 9.79 | 2.48 |
| Hepatocellular | #LO2 | NV | NV |
| | Hep3B | 6.94 | 1.07 |
| | H2P | 4.18 | 0.83 |
| | H2M | 5.57 | 2.61 |
| Colon | HCT116 | 7.29 | 2.02 |
| | DLD-1 | 2.46 | 0.91 |
| | Caco-2 | 3.08 | 0.76 |
| Prostate | PC3 | 3.77 | 1.51 |
| | LNCaP | 8.02 | 3.3 |
| | DU145 | 6.99 | 1.72 |
| Pancreatic | AsPC-1 | 3.83 | 1.14 |
| | BxPC-3 | 7.25 | 2.09 |

Note: NV, No value; #, Normal cells;
^IC50 values calculated using GraphPad Prism software (Version 5.0). Cell viability measured Using AlamarBlue® cell viability assay.

Figure 12
A. Cell viability
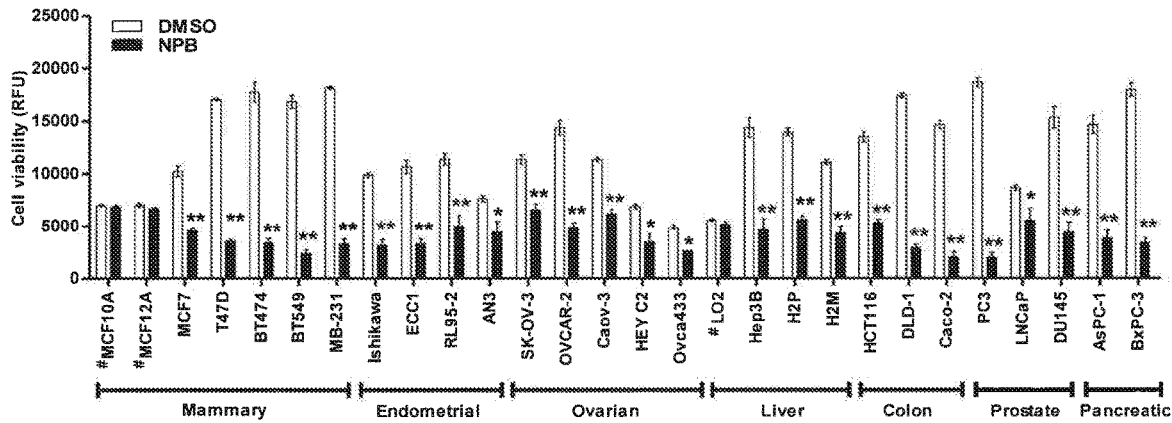
B. Caspase 3/7 activity (Apoptosis)
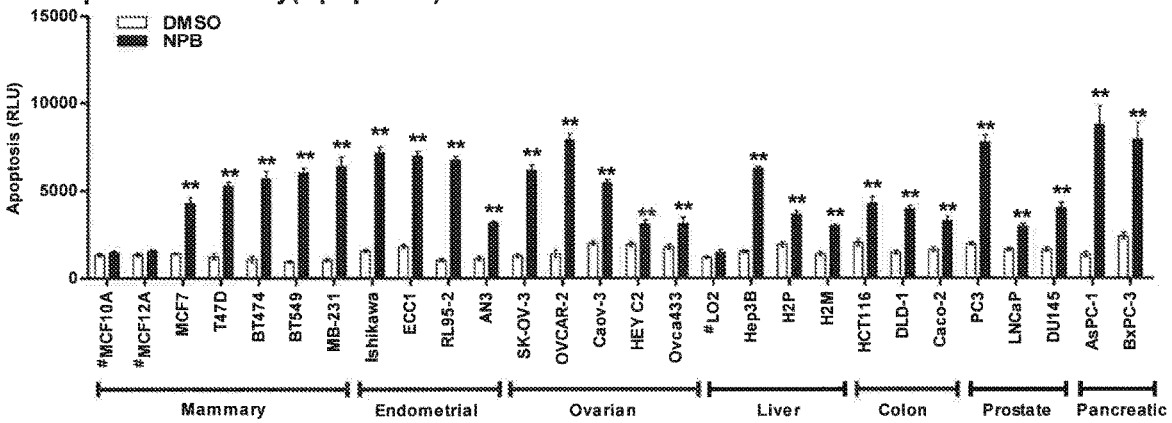
C. Cytotoxicity
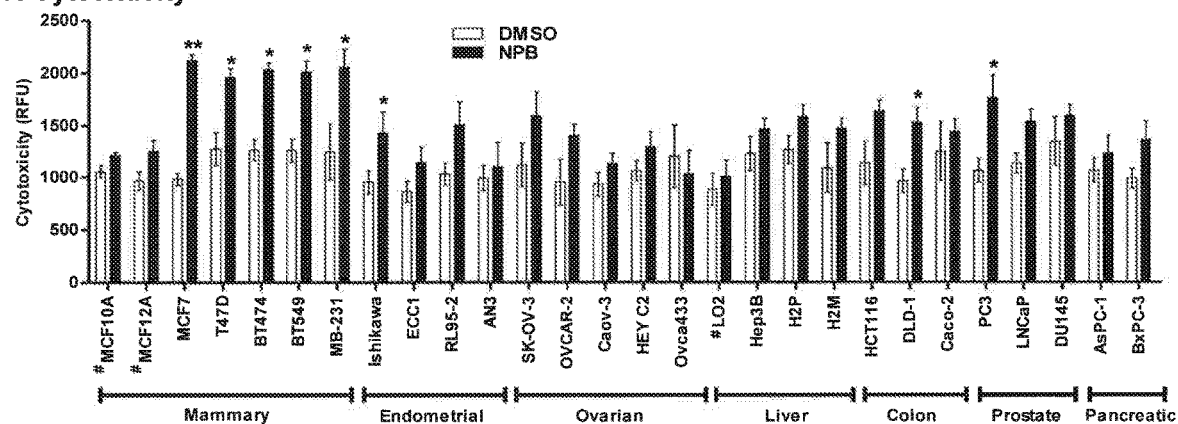

Figure 13:
A. Flow cytometry
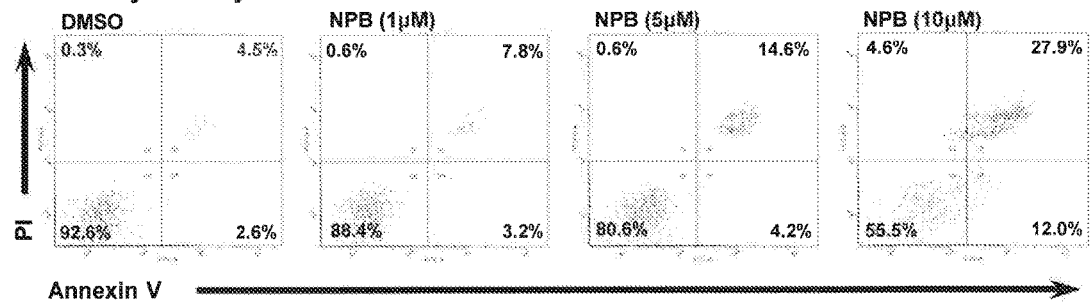
B. Cell cycle analysis
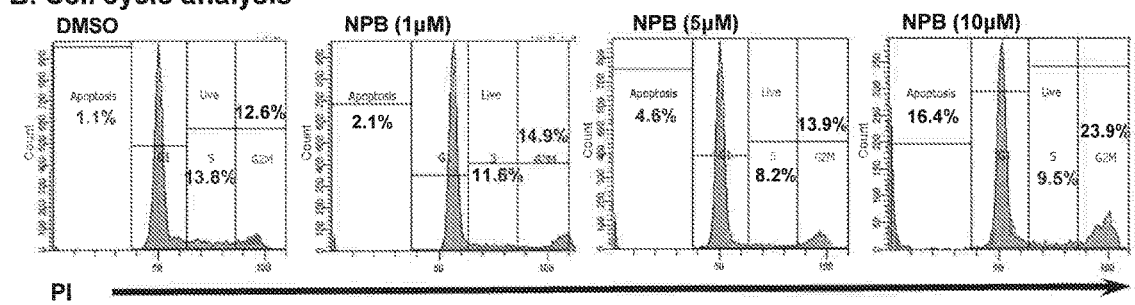
C. 3D matrigel growth
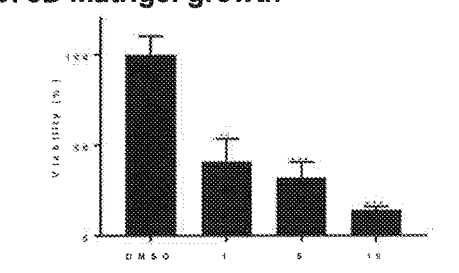
D. Soft agar colony formation
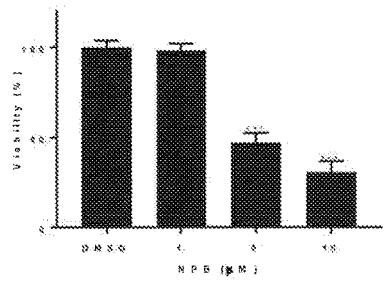
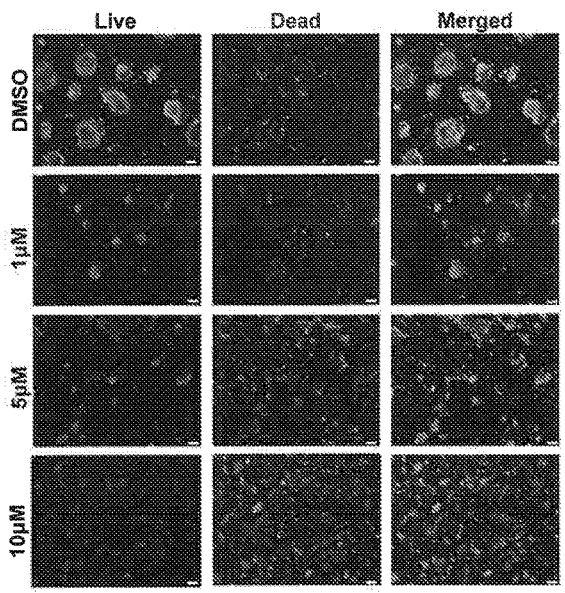
E. Foci formation
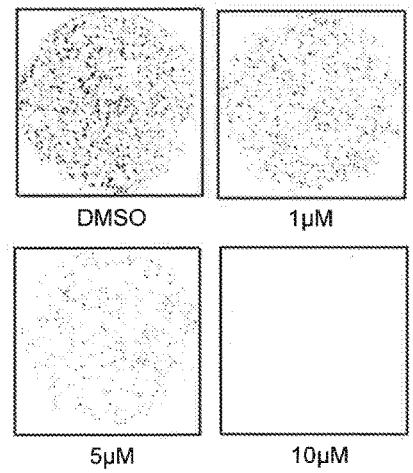

Figure 14:
A. Surface Plasmon Resonance (SPR)
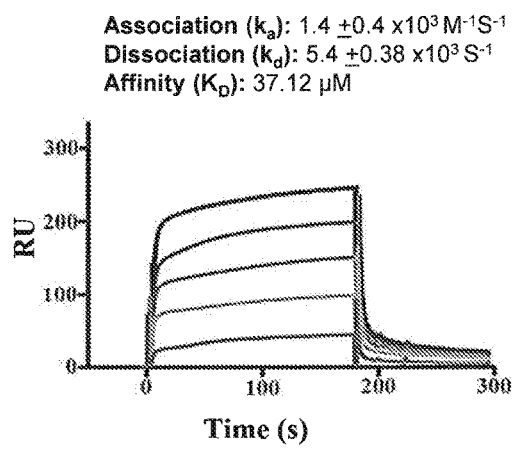
C. Western blot
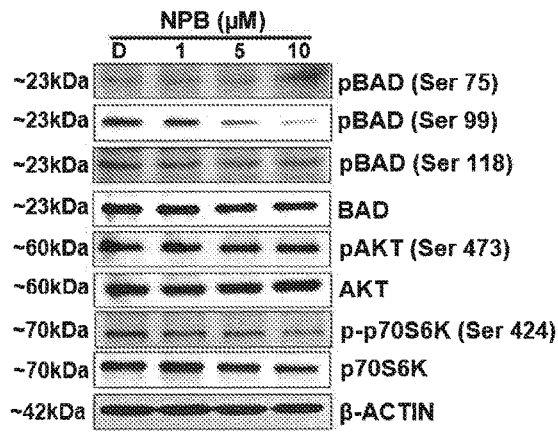
B. Western blot
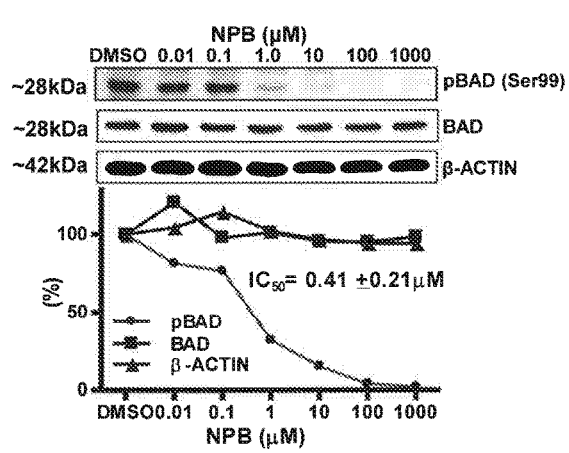
D. Western blot
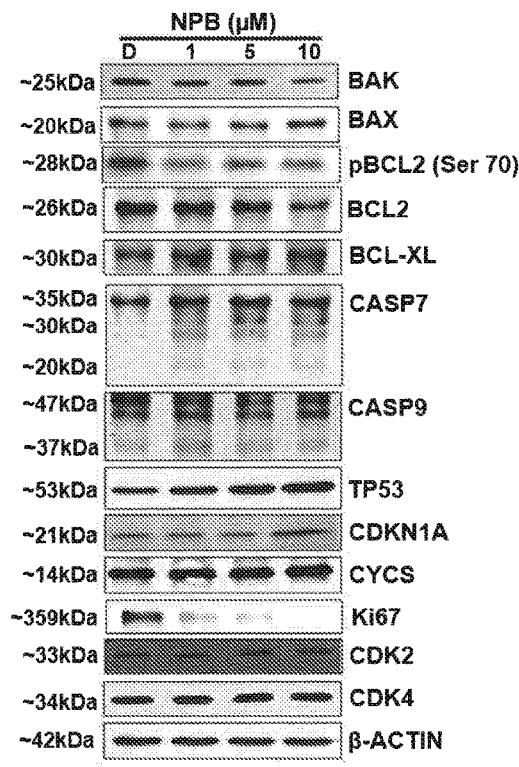

A. Western blot
B. Western blot

Figure 16:
A. Western blot
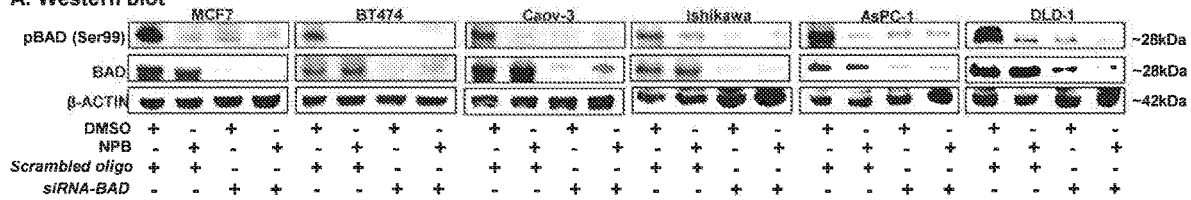
B. Cell viability
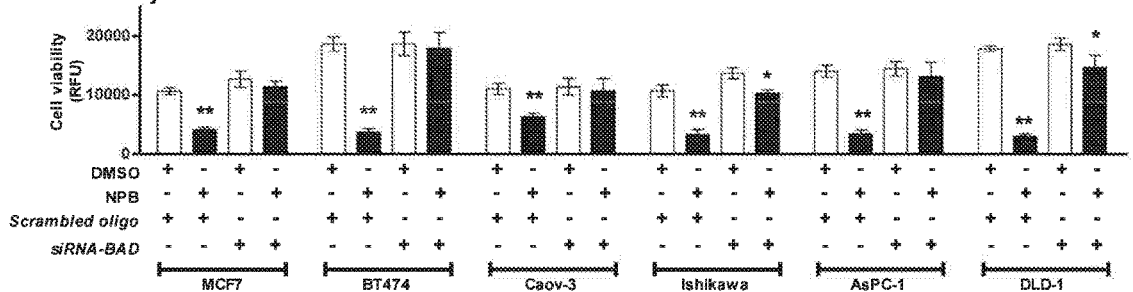
C. Caspase 3/7 activity
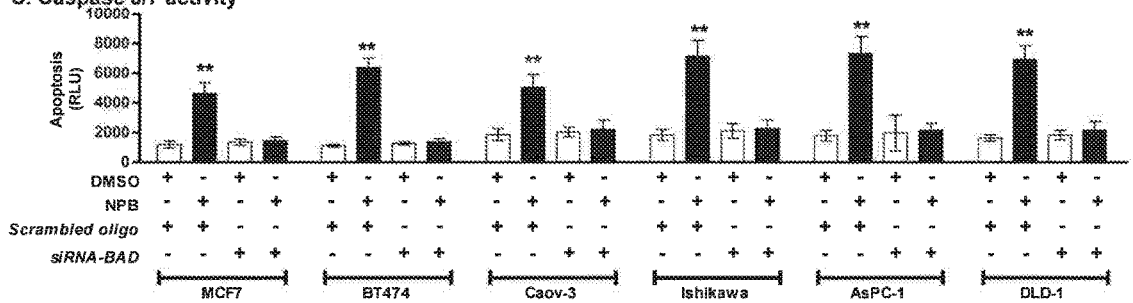

Figure 17
A. Xenograft assay
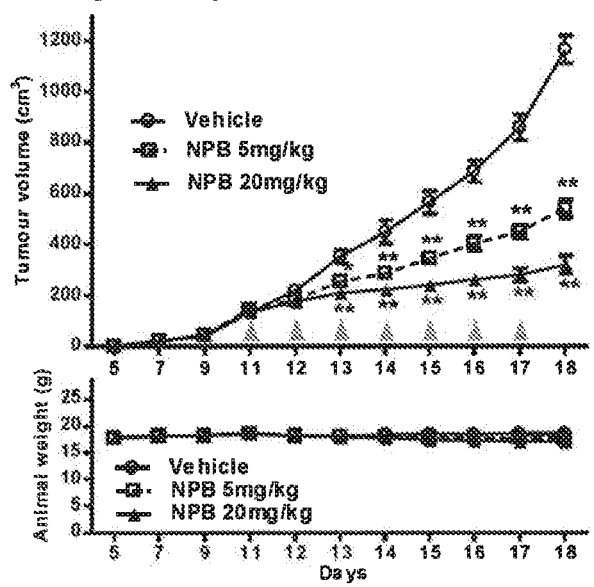
B. Tumour weight
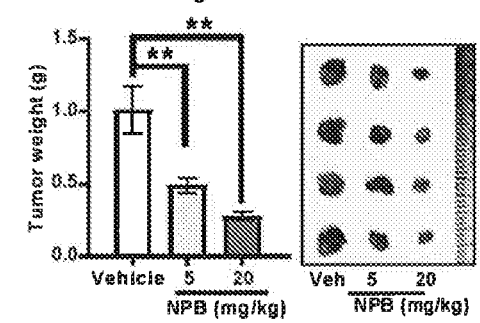
C. Western blot
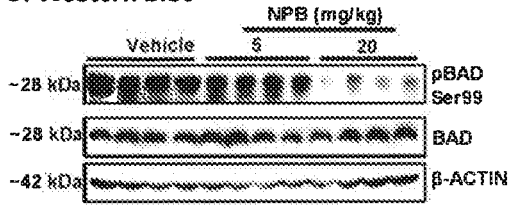

Figure 18:
A. Western blot
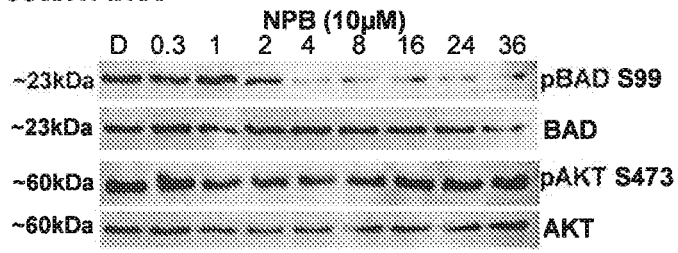
B. Kinase array
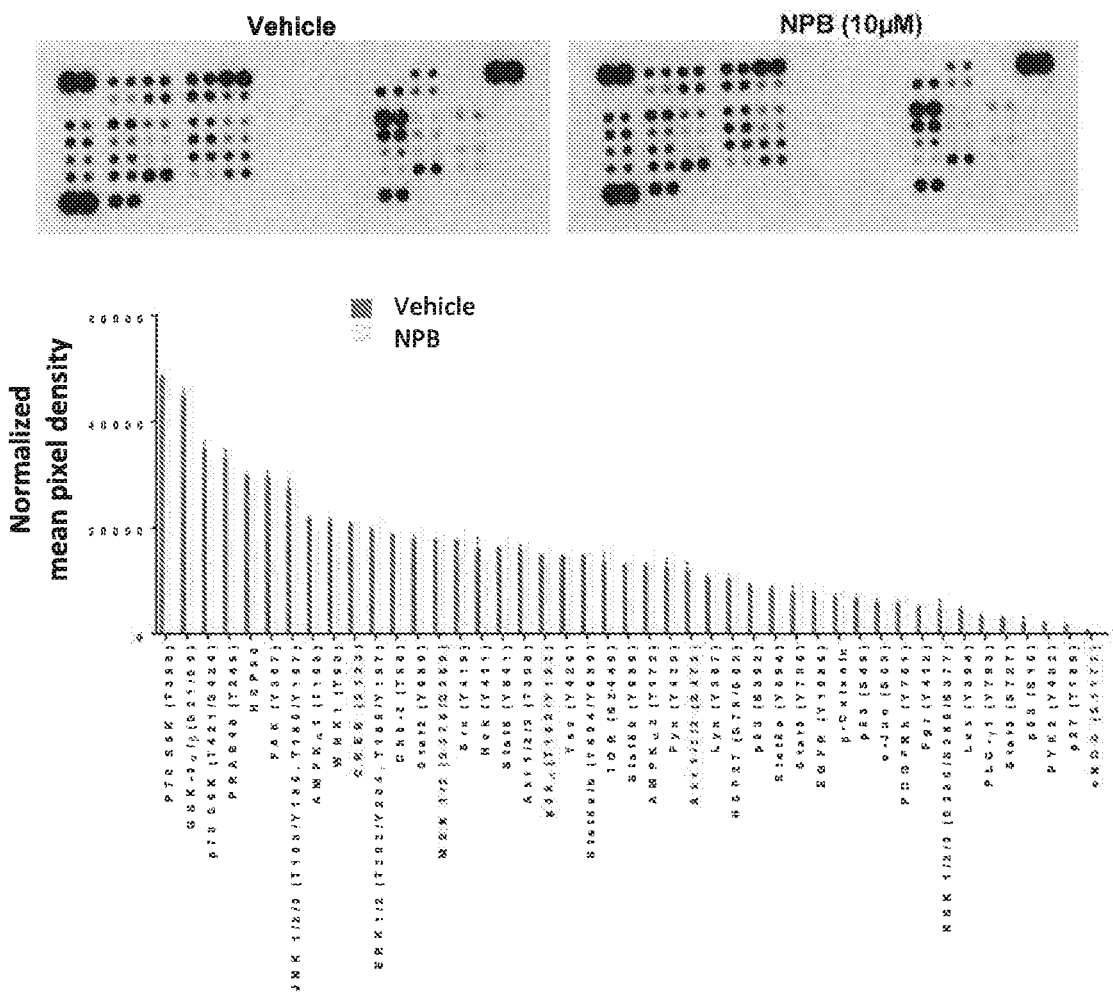

Figure 22
A
| Analogues | Structure | MCF7 IC$_{50}$ | A2780 IC$_{50}$ |
|---|---|---|---|
| NPB | 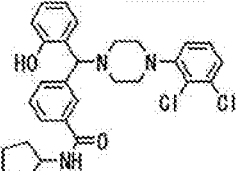 MW: 523 | 9.52 | 5.33 |
| NCK1 | 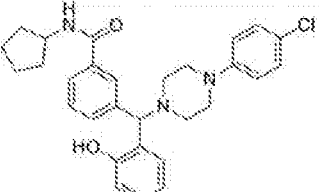 Molecular Weight: 490.0363 | NV | 26.63 |
| NCK2 | 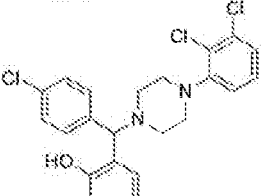 Molecular Weight: 447.7846 | NV | 19.74 |
| NCK3 | 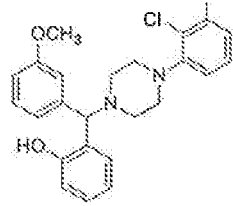 Molecular Weight: 443.3656 | NV | 50.82 |
| NCK4 | 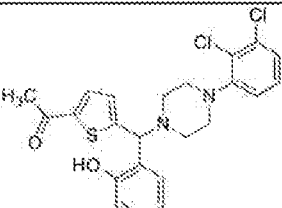 Molecular Weight: 461.4040 | NV | NV |

Figure 22
B
| | | | |
|---|---|---|---|
| NCK5 | 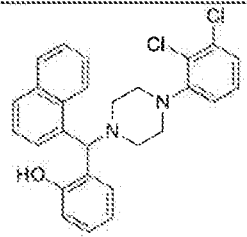<br>Molecular Weight: 463.3983 | 5.907 | 27.39 |
| NCK6 | 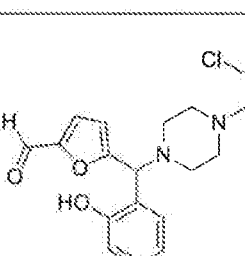<br>Molecular Weight: 431.3118 | 3.114 | 6.68 |
| NCK7 | 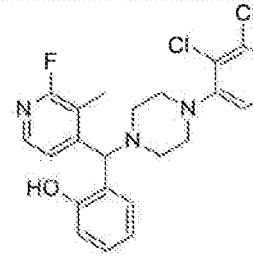<br>Molecular Weight: 448.3606 | 47.28 | 38.74 |
| NCK8 | 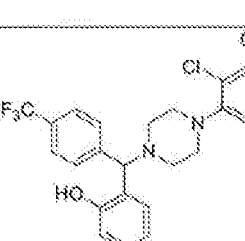<br>Molecular Weight: 481.338 | 59.52 | 23.66 |
| NCK9 | 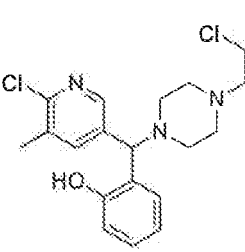<br>Molecular Weight: 462.7993 | NV | 16.06 |

Figure 22
| C | | | | |
|---|---|---|---|---|
| NCK10 | 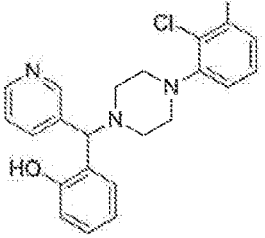<br>Molecular Weight: 414.3276 | 24.83 | 35.86 | |
| NCK14 | 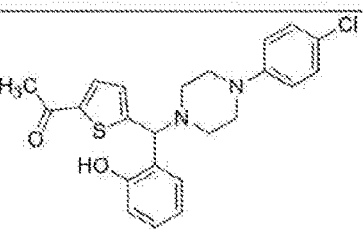<br>Molecular Weight: 426.9589 | NV | 23.26 | |
| NCK16 | 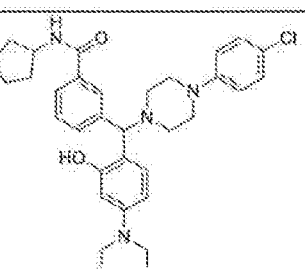<br>Molecular Weight: 561.16 | 23.35 | 9.53 | |
| NCK18 | 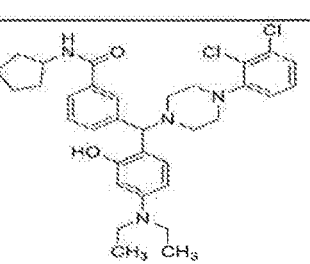<br>Molecular Weight: 595.60 | 20.93 | 2.97 | |
| NCK19 | 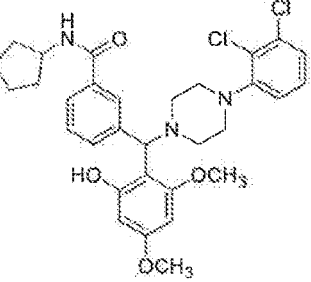<br>Molecular Weight: 584.53 | NV | 48.02 | |

Figure 22
D
| | | | |
|---|---|---|---|
| NCK20 | 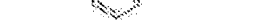<br>Molecular Weight: 413.34 | 253.8 | 8.395 |
| NCK21 | 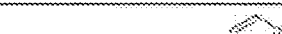<br>Molecular Weight: (not shown) | 20.91 | 21.90 |
| SG2 | 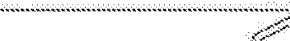<br>Molecular Weight: 426.4740 | 155.6 | 89.69 |
| SG1 | <br>Molecular Weight: 372.5026 | NV | NV |
| SG3 | <br>Molecular Weight: 469.6178 | 56.47 | 20.69 |

E

| SG7 |  | 49.87 | 41.61 |
|---|---|---|---|
| SG 4, 5, and 6 | NOT TESTED | | |

SMALL MOLECULE INHIBITORS OF BCL-2-ASSOCIATED DEATH PROMOTER (BAD) PHOSPHORYLATION

The present invention relates to novel compounds, and in particular to compounds which are inhibitors of Bcl-2-associated death promoter (BAD) in cancer cells, to the compounds for use in the treatment or prevention of cancer and to pharmaceutical compositions comprising the compounds.

Apoptosis or programmed cell death is a regulatory mechanism pivotally involved in elimination of auto-reactive immune cells, aged cells and cells with irreparable DNA damage [1]. Apoptosis is executed by two distinct mechanisms in vertebrates—the extrinsic and the intrinsic pathway [2]. The intrinsic pathway is activated under hypoxic conditions, after severe genomic damage, oxidative stress or after growth factor depletion [3]. BCL-2 family proteins possess a pivotal role in regulating the intrinsic apoptotic pathway [4]. More than 20 BCL-2 family members have been identified and broadly classified into anti-apoptotic, pro-apoptotic, and BH3-only proteins. BCL-2, BCL-xL and BCL-w are anti-apoptotic; BAK and BAX are pro-apoptotic; and BAD, BIM, PUMA, NOXA are the predominant pro-apoptotic BH3 only proteins [5-7]. Hence, the members of the BCL-2 family serve both pro- and anti-apoptotic functions with an equilibrium maintained between them, and pro-apoptotic BH3 only proteins are normally repressed to ensure homeostasis [8].

Suppression of apoptosis contributes to inappropriate cell survival and cancer development and/or progression [9-11]. In most malignancies, expression of anti-apoptotic proteins is increased leading to the development of resistance to apoptosis. Bcl-2 associated death promoter (BAD) plays a critical role in regulating apoptosis by interacting with Bcl-2, Bcl-xL and Bcl-w [12]. Human BAD is phosphorylated at Ser75 (equivalent murine residue is Ser112) by p44/42 MAP kinase and Ser99 (equivalent murine residue is Ser136) by AKT/p70S6K [13]. Both serine residues are also phosphorylated by Pim family kinases to prevent apoptosis [14]. Phosphorylation of BAD at either of these residues results in loss of the ability of hBAD to heterodimerize with BCL-xL or BCL-2 [15]. Phosphorylated BAD protein is heterodimerized with 14-3-3 protein and sequestered in the cytoplasm [16]. Upon initiation of apoptosis, BAD undergoes dephosphorylation and heterodimerizes with BCL-2, BCL-xL or BCL-w which allows BAK and BAX to promote the release of cytochrome C to the cytoplasm with subsequent promotion of the intrinsic apoptotic pathway [17]. BAD has also been reported to possess other protein and functional interactions within the cell. For example, BAD expression is regulated by p53 and BAD complexes with p53 to promote apoptosis [18]. Bad is transcriptionally up-regulated by p53 and forms a Bad/p53 complex at the mitochondria to induce apoptosis [18.]. Clinically, high BAD expression is associated with high Gleason scores in prostate cancer [15] and BAD phosphorylation has been reported to predict poor overall survival in ovarian cancer [19] and to be associated with resistance to cisplatin [19]. Furthermore, phosphorylated BAD is observed in more than 80% of the CD44 positive cancer stem cell (CSC) population in breast cancer and BAD phosphorylation has been reported to be essential for CSC survival [20].

Numerous small molecule modulators of programmed cell death have been developed, targeting BCL-2 family proteins for therapeutic use against various human malignancies [21-23]. To date there has been no reported small molecule modulators of BH3-only proteins such as BAD. Thus, there is a necessity to develop better and efficient compounds/therapies for managing cancer by inhibiting BAD phosphorylation without affecting the upstream events.

In the present invention there is provided a compound of general formula (I):

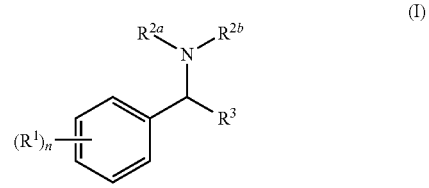

(I)

wherein:

each $R^1$ is independently halo, OH, cyano, nitro, $NR^{10}R^{11}$, $C(O)R^{10}$, $C(O)OR^{10}$, $C(O)NR^{10}R^{11}$, $-S(O)_qNR^{10}R^{11}$, $C_{1-6}$ alkyl, $C_{1-6}$ haloalkyl, $-O(C_{1-6}$ alkyl), $-O(C_{1-6}$ haloalkyl), aryl, heteroaryl, $-O$-aryl or $-O$-heteroaryl, wherein each $R^{10}$ and $R^{11}$ is independently selected from H or $C_{1-6}$ alkyl optionally substituted with one or more substituents selected from OH, halo, cyano, $NH_2$, aryl or heteroaryl;

alkyl and haloalkyl groups $R^1$ are optionally substituted with one or more substituents selected from OH, cyano, $-S(O)_pNR^4R^5$, $-C(O)NR^4R^5$, aryl, heteroaryl, $-O$-aryl or $-O$-heteroaryl $-O(C_{1-6}$ alkyl) optionally substituted with aryl or $-O(C_{1-6}$ haloalkyl);

aryl or heteroaryl groups $R^1$ are optionally substituted with one or more substituents selected from halo, OH, cyano, nitro, $-NR^4R^5$, $-S(O)_pNR^4R^5$, $-C(O)NR^4R^5$, $-C(O)R^4$, $-C(O)OR^4$ or $-C_{1-6}$ alkyl or $-O(C_{1-6}$ alkyl), either of which is optionally substituted with one or more substituents selected from OH, halo, aryl, heteroaryl, $-O(C_{1-6}$ alkyl), $O(C_{1-6}$ haloalkyl), $-O$-aryl or $-O$-heteroaryl);

p is 1 or 2;

each $R^4$ and $R^5$ is independently selected from H or $C_{1-4}$ alkyl or $R^4$ and $R^5$ together with a nitrogen atom to which they are attached may form a 3- or 8-membered heterocyclic ring, optionally containing one or more additional heteroatoms selected from O, N and S;

n is 0, 1, 2, 3 4, or 5;

$R^{2a}$ and $R^{2b}$ are each independently $C_{1-6}$ alkyl optionally substituted with one or more substituents selected from halo, OH, aryl or heteroaryl; or $R^{2a}$ and $R^{2b}$ together with the nitrogen atom to which they are attached form a 5- or 6-membered heterocyclic ring optionally containing one or more further heteroatoms selected from O, N or S and optionally substituted with one or more substituents $R^6$;

each $R^6$ is independently selected from aryl, heteroaryl, $-O$-aryl, $-O$-heteroaryl, carbocyclyl, heterocyclyl, $-O$-carbocyclyl, $-O$-heterocyclyl, $R^{12}$, $OR^{12}$, $C(O)R^{12}$, $C(O)OR^{11}$, $C(O)NR^{11}R^{12}$, CN, OH, each $R^{11}$ and $R^{12}$ is independently H or $C_{1-4}$ alkyl, either or which may be substituted with one or more aryl or heteroaryl groups, wherein aryl and heteroaryl groups are substituted with one or more substituent selected from halo, OH, cyano, nitro, $-NR^4R^5$, $-S(O)_pNR^4R^5$, $-C(O)NR^4R^5$, $-C(O)R^4$, $-C(O)$ OR$^4$ or —C$_{1-6}$ alkyl or —O(C$_{1-6}$ alkyl), either of which is optionally substituted with one or more substituents selected from OH, halo, aryl, heteroaryl, —O(C$_{1-6}$ alkyl), O(C$_{1-6}$ haloalkyl), —O-aryl or —O-heteroaryl); wherein R$^4$ and R$^5$ are as defined above; or R$^{11}$ and R$^{12}$ may combine with a nitrogen atom to which they are attached to form a 3 to 8-membered heterocyclic ring optionally containing one or more further heteroatoms selected from N, O and S and optionally substituted with C$_{1-4}$ alkyl, C$_{1-4}$ haloalkyl or halo;

R$^3$ is aryl, heteroaryl, carbocyclyl or heterocyclyl any of which is optionally substituted with one or more substituents R$^7$ selected from halo, —C$_{1-4}$ alkyl optionally substituted with aryl, —O(C$_{1-4}$ alkyl) optionally substituted with aryl, —C$_{1-4}$ haloalkyl, —O(C$_{1-4}$ haloalkyl) or —C(O)NR$^8$R$^9$;

each R$^8$ and R$^9$ is independently selected from H, C$_{1-4}$ alkyl or C$_{3-6}$ cycloalkyl or R$^8$ and R$^9$ together with the nitrogen atom to which they are attached may form a 5- or 6-membered heterocyclic ring, optionally containing one or more additional heteroatoms selected from O, N and S;

or a pharmaceutically acceptable salt, solvate or hydrate thereof or a deuterated or tritiated variant thereof, including all stereoisomers.

The compounds of general formula (I) inhibit of site-specific BAD phosphorylation without affecting its upstream kinase and are therefore of use in promoting apoptosis in multiple cancer-derived cells.

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

In the present specification the term "C$_{1-6}$ alkyl" refers to a fully saturated straight or branched hydrocarbon chain having from 1 to 6 carbon atoms. Examples include methyl, ethyl, n-propyl, isopropyl, t-butyl, n-hexyl.

The term "C$_{1-4}$ alkyl" has a similar meaning but refers to alkyl groups with between 1 and 4 carbon atoms.

The term "C$_{1-6}$ haloalkyl" refers to a C$_{1-6}$ alkyl group as defined above in which one or more hydrogen atoms are replaced by halo atoms. Haloalkyl groups may have any number of halo substituents from 1 to perhalosubstituted. Examples include chloromethyl, trifluoromethyl, 1-bromoethyl, 1,1,2,2-tetrafluoroethyl etc.

The term "carbocyclyl" refers to a non-aromatic hydrocarbon ring having from 3 to 7 carbon atoms and optionally containing one or more carbon-carbon double bond. Examples include C$_{3-7}$ cycloalkyl groups such as cyclopropyl, cyclobutyl, cyclopentyl, cyclohexyl and cycloheptyl and cycloalkenyl groups such as cyclohexenyl.

The term "heterocyclyl" refers to a non-aromatic ring having from 5 to 7 carbon atoms and at least one ring heteroatom selected from N, O and S. Examples include piperazinyl, piperidinyl, morpholinyl, pyrrolidinyl and imidazolinyl.

In the present specification, "halo" refers to fluoro, chloro, bromo or iodo.

The term "aryl" in the context of the present specification refer to a ring system with aromatic character having from 5 to 14 ring carbon atoms unless specified otherwise, and containing up to three rings. Where an aryl group contains more than one ring, not all rings must be fully aromatic in character. Examples of aromatic moieties are benzene, naphthalene, indane and indene.

The term "heteroaryl" in the context of the specification refer to a ring system with aromatic character having from 5 to 14 ring atoms (unless specified otherwise) at least one of which is a heteroatom selected from N, O and S, and containing up to three rings. Where a heteroaryl group contains more than one ring, not all rings must be fully aromatic in character. Examples of heteroaryl groups include pyridine, pyrimidine, indole, isoindole, benzofuran, benzimidazole, benzoxazole, benzisoxazole and indolene.

In the compounds of general formula (I), n is suitably 2 or 3, for example 2. At least one R$^1$ group may be OH. In this case, the OH group is suitably at the position adjacent to the —CH(R$^3$)NR$^{2a}$R$^{2b}$ group.

Suitably, the compound of general formula (I) is a compound of general formula general formula (IA):

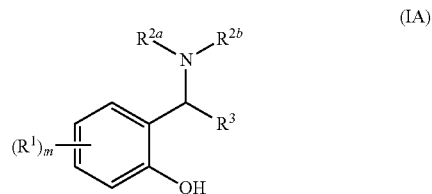

(IA)

wherein R$^1$, R$^{2a}$, R$^{2b}$ and R$^3$ are as defined above and m is 0, 1, 2, 3 or 4.

Suitably, in the compound of general formulae (I) and (IA):

each R$^1$ is independently halo, C$_{1-6}$ alkyl, C$_{1-6}$ haloalkyl, aryl or heteroaryl, wherein aryl or heteroaryl groups are optionally substituted with one or more substituents selected from halo, OH, cyano, nitro, —S(O)$_p$NR$^4$R$^5$, —C(O)NR$^4$R$^5$, —C$_{1-6}$ alkyl optionally substituted with aryl, —C$_{1-6}$ haloalkyl, —O(C$_{1-6}$ alkyl) optionally substituted with aryl or —O(C$_{1-6}$ haloalkyl);

p is 0, 1 or 2;

each R$^4$ and R$^5$ is independently selected from H or C$_{1-4}$ alkyl or R$^4$ and R$^5$ together with the nitrogen atom to which they are attached may form a 5- or 6-membered heterocyclic ring, optionally containing one or more additional heteroatoms selected from O, N and S;

R$^{2a}$ and R$^{2b}$ are each independently C$_{1-6}$ alkyl optionally substituted with one or more substituents selected from halo, OH, aryl or heteroaryl; or R$^{2a}$ and R$^{2b}$ together with the nitrogen atom to which they are attached form a 5- or 6-membered heterocyclic ring optionally containing one or more further heteroatoms selected from O, N or S and optionally substituted with one or more substituents R$^6$;

each R$^6$ is independently selected from aryl, heteroaryl, —O-aryl, —O-heteroaryl or C$_{1-4}$ alkyl substituted with one or more aryl or heteroaryl groups, wherein aryl and heteroaryl groups are substituted with one or more substituent selected from halo, C$_{1-4}$ alkyl, C$_{1-4}$ haloalkyl, —O(C$_{1-4}$ alkyl) or —O(C$_{1-4}$ haloalkyl);

R$^3$ is aryl, heteroaryl, carbocyclyl or heterocyclyl any of which is optionally substituted with one or more substituents R$^7$ selected from halo, —C$_{1-4}$ alkyl optionally substituted with aryl, —O(C$_{1-4}$ alkyl) optionally substituted with aryl, —C$_{1-4}$ haloalkyl, —O(C$_{1-4}$ haloalkyl) or —C(O)NR$^8$R$^9$;

each R$^8$ and R$^9$ is independently selected from H, C$_{1-4}$ alkyl or C$_{3-6}$ cycloalkyl or R$^8$ and R$^9$ together with the nitrogen atom to which they are attached may form a 5- or 6-membered heterocyclic ring, optionally containing one or more additional heteroatoms selected from O, N and S;

or a pharmaceutically acceptable salt, solvate or hydrate thereof or a deuterated or tritiated variant thereof, including all stereoisomers.

In some suitable compounds of general formula (IA), m is 0 so that the group $R^1$ is not present.

In other suitable compounds m is 1 or 2, but more usually 1.

In such cases, $R^1$ is suitably halo, particularly chloro or fluoro; or alternatively $R^1$ is an aryl or heteroaryl group optionally substituted as described above. More usually, $R^1$ is chloro, fluoro or aryl optionally substituted as described above.

When $R^1$ is an aryl or heteroaryl group it is suitably at the 4-position of the phenyl ring (where the carbon substituted with the OH group is designated as position 1).

Suitable substituents for aryl or heteroaryl groups $R^1$ include halo, OH, cyano, nitro, —$SO_2NH_2$, —$C(O)NR^4R^5$, —$C_{1-4}$ alkyl optionally substituted with aryl, —$C_{1-4}$ haloalkyl, —$O(C_{1-4}$ alkyl) optionally substituted with aryl or —$O(C_{1-4}$ haloalkyl), where $R^4$ and $R^5$ together with the nitrogen atom to which they are attached form a piperidine or pyrrolidine ring.

More suitable substituents for aryl or heteroaryl groups $R^1$ include chloro, fluoro, methyl, ethyl, trifluoromethyl, benzyl, methoxy, ethoxy, benzyloxy, trifluoromethoxy and piperidine-1-carbonyl.

In some suitable compounds of the invention, $R^{2a}$ and $R^{2b}$ together with the nitrogen atom to which they are attached form a 5- or 6-membered heterocyclic ring optionally containing one or more further heteroatoms selected from O, N or S and optionally substituted with one or more substituents $R^6$, wherein $R^6$ is as defined above.

More suitably, $R^{2a}$ and $R^{2b}$ together with the nitrogen atom to which they are attached form a 6-membered heterocyclic ring optionally substituted with one or more substituents $R^6$.

Still more suitably, the 6-membered ring formed by $R^{2a}$ and $R^{2b}$ is a piperidine or piperazine ring, most suitably a piperazine ring. When $R^{2a}$ and $R^{2b}$ form a piperazine ring, it may optionally be substituted by one or more substituents $R^6$ as defined above but is suitably substituted by a single $R^6$ substituent at the piperazine 4-position such that the compound of general formula (I) is a compound of general formula (IB):

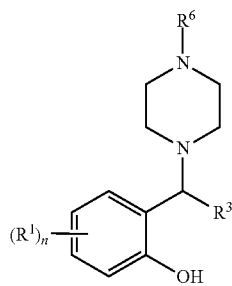

(IB)

wherein $R^1$, n, $R^3$ and $R^6$ are as defined for general formulae (I) and (IA).

Particularly suitable substituents $R^6$ include aryl, heteroaryl, —O-aryl, —O-heteroaryl or methyl substituted with one or two aryl or heteroaryl groups; wherein aryl and heteroaryl groups are substituted with one or more substituents selected from halo, methyl, ethyl, trifluoromethyl, methoxy, ethoxy or trifluoromethoxy.

Still more suitable substituents $R^6$ include phenyl, heteroaryl, —O-phenyl, —O-heteroaryl, benzyl, —CH(phenyl)$_2$, —$CH_2$-heteroaryl and —CH(heteroaryl)$_2$, where the heteroaryl group is selected from pyridinyl, indolyl, isoindolyl, benzoxazolyl and benzisoxazolyl and wherein any of the above $R^6$ groups may be substituted as described above, but more suitably with one or more substituents selected from halo, methyl ethyl and trifluoromethyl.

In more suitable compounds of general formula (I) and (IA), $R^3$ is aryl or heteroaryl optionally substituted with one or more substituents $R^7$ as described above.

Most suitably, $R^3$ is phenyl optionally substituted with one or more substituents $R^7$ such that the compound of general formula (I) is a compound of general formula (IC):

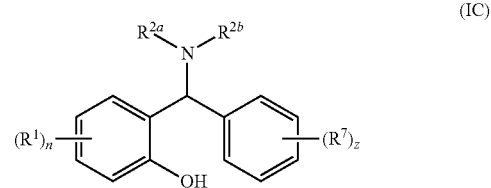

(IC)

wherein $R^1$, n, $R^{2a}$, $R^{2b}$ and $R^7$ are as defined for general formula (I) or (IA) and z is 0 to 5.

More suitably, z is 0, 1, 2 or 3, most suitably 0, 1 or 2.

$R^7$ is as defined above but in some suitable compounds $R^7$ not present (i.e. z is 0), or $R^7$ is halo, —$C_{1-4}$ alkyl, benzyl, —$O(C_{1-4}$ alkyl) benzyloxy, —$C_{1-4}$ haloalkyl, —$O(C_{1-4}$ haloalkyl) or —$C(O)NR^8R^9$, where $R^8$ and $R^9$ together with the nitrogen atom to which they are attached form a piperidinyl ring or wherein $R^8$ is H and $R^9$ is $C_{3-7}$ cycloalkyl.

More suitably, $R^7$ not present or each $R^7$ is independently halo, especially chloro or fluoro, methyl, ethyl, benzyl, methoxy, ethoxy, benzyloxy, —C(O)-piperidinyl or —C(O)NH—$C_{3-7}$ cycloalkyl.

Some particularly suitable compounds of the invention are compounds of general formula (ID):

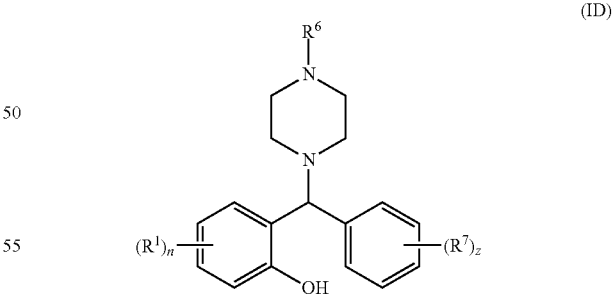

(ID)

wherein $R^1$, n, $R^6$, $R^7$ and z are as defined above for general formulae (I), (IA), (IB) and (IC).

Example compounds of general formula (I) include:
2-((2-chlorophenyl)(4-(4-methoxyphenyl)piperazin-1-yl) methyl)phenol (Compound 1);
2-((4-chlorophenyl)(4-(4-methoxyphenyl)piperazin-1-yl) methyl)phenol (Compound 2);
2-((4-(benzyloxy)-3-fluorophenyl)(4-(4-methoxyphenyl) piperazin-1-yl)methyl)phenol (Compound 3);

(4-((2-hydroxyphenyl)(4-(4-Methoxyphenyl)piperazinyl) methyl)phenyl)(piperidin-1-yl)methanone (Compound 4);

3-((5-chloro-2-hydroxyphenyl)(4-(4-methoxyphenyl)piperazin-1-yl)methyl)-N-cyclopentylbenzamide (Compound 5);

2-((4-(benzyloxy)-3-fluorophenyl)(4-(4-methoxyphenyl) piperazin-1-yl)methyl)-4-chlorophenol (Compound 6);

2-((4-(benzyloxy)-3-fluorophenyl)(4-(6-fluorobenzo[d] isoxazol-3-yl)piperidin-1-yl)methyl)phenol (Compound 7);

2-((4-(2,3-dichlorophenyl)piperazin-1-yl)(o-tolyl)methyl) phenol (Compound 8);

N-cyclopentyl-3-((4-(2,3-dichlorophenyl)piperazin-1-yl)(2-hydroxyphenyl)methyl) benzamide (Compound 9, NPB);

2-((4-(benzyloxy)-3-fluorophenyl)(4-(2,3-dichlorophenyl) piperazin-1-yl)methyl)phenol (Compound 10);

2-((4-((4-chlorophenyl)(phenyl)methyl)piperazin-1-yl) (phenyl)methyl)phenol (Compound 11);

2-((4-((4-chlorophenyl)(phenyl)methyl)piperazin-1-yl)(p-tolyl)methyl)phenol (Compound 12);

2-((4-chlorophenyl)(4-((4-chlorophenyl)(phenyl)methyl) piperazin-1-yl)methyl)phenol (Compound 13);

2-((4-((4-chlorophenyl)(phenyl)methyl)piperazin-1-yl)(4-ethylphenyl)methyl)phenol (Compound 14);

(4-((4-((4-chlorophenyl)(phenyl)methyl)piperazin-1-yl)(2-hydroxyphenyl)methyl)phenyl) (piperidin-1-yl)methanone (Compound 15);

N-cyclopentyl-3-((4-(2,3-dichlorophenyl)piperazin-1-yl)(4-hydroxy-[1,1'-biphenyl]-3-yl)methyl)benzamide (Compound 16);

N-cyclopentyl-3-((4-(2,3-dichlorophenyl)piperazin-1-yl)(4-hydroxy-2'-methyl-[1,1'-biphenyl]-3-yl)methyl)benzamide (Compound 17);

N-cyclopentyl-3-((4-(2,3-dichlorophenyl)piperazin-1-yl)(4-hydroxy-3'-methyl-[1,1'-biphenyl]-3-yl)methyl)benzamide (Compound 18);

N-cyclopentyl-3-((4-(2,3-dichlorophenyl)piperazin-1-yl)(4-hydroxy-4'-methyl-[1,1'-biphenyl]-3-yl)methyl)benzamide (Compound 19);

3-((2'-chloro-4-hydroxy-[1,1'-biphenyl]-3-yl)(4-(2,3-dichlorophenyl)piperazin-1-yl)methyl)-N-cyclopentylbenzamide (Compound 20);

3-((3'-chloro-4-hydroxy-[1,1'-biphenyl]-3-yl)(4-(2,3-dichlorophenyl)piperazin-1-yl)methyl)-N-cyclopentylbenzamide (Compound 21);

3-((4'-chloro-4-hydroxy-[1,1'-biphenyl]-3-yl)(4-(2,3-dichlorophenyl)piperazin-1-yl)methyl)-N-cyclopentylbenzamide (Compound 22);

N-cyclopentyl-3-((4-(2,3-dichlorophenyl)piperazin-1-yl) (4'-ethyl-4-hydroxy-[1,1'-biphenyl]-3-yl)methyl)benzamide (Compound 23);

N-cyclopentyl-3-((4-(2,3-dichlorophenyl)piperazin-1-yl)(4-hydroxy-4'-(piperidine-1-carbonyl)-[1,1'-biphenyl]-3-yl)methyl)benzamide (Compound 24);

N-cyclopentyl-3-((4-(2,3-dichlorophenyl)piperazin-1-yl)(4-hydroxy-4'-methoxy-[1,1'-biphenyl]-3-yl)methyl)benzamide (Compound 25);

N-cyclopentyl-3-((4-(2,3-dichlorophenyl)piperazin-1-yl) (2'-ethyl-4-hydroxy-[1,1'-biphenyl]-3-yl)methyl)benzamide (Compound 26);

N-cyclopentyl-3-((4-(2,3-dichlorophenyl)piperazin-1-yl) (2'-fluoro-4-hydroxy-[1,1'-biphenyl]-3-yl)methyl)benzamide (Compound 27);

N-cyclopentyl-3-((4-(2,3-dichlorophenyl)piperazin-1-yl) (3'-fluoro-4-hydroxy-[1,1'-biphenyl]-3-yl)methyl)benzamide (Compound 28);

N-cyclopentyl-3-((4-(2,3-dichlorophenyl)piperazin-1-yl) (4'-fluoro-4-hydroxy-[1,1'-biphenyl]-3-yl)methyl)benzamide (Compound 29);

N-cyclopentyl-3-((4-(2,3-dichlorophenyl)piperazin-1-yl)(4-hydroxy-3'-nitro-[1,1'-biphenyl]-3-yl)methyl)benzamide (Compound 30);

N-cyclopentyl-3-((4-(2,3-dichlorophenyl)piperazin-1-yl)(4-hydroxy-3'-sulfamoyl-[1,1'-biphenyl]-3-yl)methyl)benzamide (Compound 31);

N-cyclopentyl-3-((4-(2,3-dichlorophenyl)piperazin-1-yl)(4-hydroxy-2'-(trifluoromethyl)-[1,1'-biphenyl]-3-yl) methyl)benzamide (Compound 32);

N-cyclopentyl-3-((4-(2,3-dichlorophenyl)piperazin-1-yl)(4-hydroxy-3'-(trifluoromethyl)-[1,1'-biphenyl]-3-yl) methyl)benzamide (Compound 33);

N-cyclopentyl-3-((4-(2,3-dichlorophenyl)piperazin-1-yl)(4-hydroxy-4'-(trifluoromethyl)-[1,1'-biphenyl]-3-yl) methyl)benzamide (Compound 34);

3-((2'-cyano-4-hydroxy-[1,1'-biphenyl]-3-yl)(4-(2,3-dichlorophenyl)piperazin-1-yl)methyl)-N-cyclopentylbenzamide (Compound 35);

3-((3'-cyano-4-hydroxy-[1,1'-biphenyl]-3-yl)(4-(2,3-dichlorophenyl)piperazin-1-yl)methyl)-N-cyclopentylbenzamide (Compound 36)

3-((4'-cyano-4-hydroxy-[1,1'-biphenyl]-3-yl)(4-(2,3-dichlorophenyl)piperazin-1-yl)methyl)-N-cyclopentylbenzamide (Compound 37);

3-((2'-chloro-4-hydroxy-4'-(trifluoromethyl)-[1,1'-biphenyl]-3-yl)(4-(2,3-dichlorophenyl) piperazin-1-yl)methyl)-N-cyclopentylbenzamide (Compound 38);

N-cyclopentyl-3-((2',4'-dichloro-4-hydroxy-[1,1'-biphenyl]-3-yl)(4-(2,3-dichlorophenyl) piperazin-1-yl)methyl)benzamide (Compound 39);

3-((4'-chloro-2',4-dihydroxy-[1,1'-biphenyl]-3-yl)(4-(2,3-dichlorophenyl)piperazin-1-yl)methyl)-N-cyclopentylbenzamide (Compound 40);

3-((4-(4-chlorophenyl)piperazin-1-yl)(2-hydroxyphenyl) methyl)-N-cyclopentylbenzamide (Compound 41, NCK1);

2-((4-chlorophenyl)(4-(2,3-dichlorophenyl)piperazin-1-yl) methyl)phenol (Compound 42, NCK2);

2-((4-(2,3-dichlorophenyl)piperazin-1-yl)(3-methoxyphenyl)methyl)phenol (Compound 43, NCK3);

1-(5-((4-(2,3-dichlorophenyl)piperazin-1-yl)(2-hydroxyphenyl)methyl)thiophen-2-yl)ethanone (Compound 44, NCK4);

2-((4-(2,3-dichlorophenyl)piperazin-1-yl)(naphthalen-1-yl) methyl)phenol (Compound 45, NCK5);

5-((4-(2,3-dichlorophenyl)piperazin-1-yl)(2-hydroxyphenyl)methyl)furan-2-carbaldehyde (Compound 46, NCK6);

2-((2,3-dichlorophenyl) piperazin-1-yl)(2-fluoro-3-methylpyridin-4-yl)methyl)phenol (Compound 47, NCK7);

2-((4-(2,3-dichlorophenyl)piperazin-1-yl)(4-(trifluoromethyl)phenyl)methyl)phenol (Compound 48, NCK8);

2-((6-chloro-5-methylpyridin-3-yl)(4-(2,3-dichlorophenyl) piperazin-1-yl)methyl)phenol (Compound 49, NCK9);

2-((4-(2,3-dichlorophenyl)piperazin-1-yl)(pyridin-3-yl) methyl)phenol (Compound 50, NCK10);

1-(5-((4-(4-chlorophenyl)piperazin-1-yl)(2-hydroxyphenyl) methyl)thiophen-2-yl)ethanone (Compound 51, NCK14);

3-((4-(4-chlorophenyl)piperazin-1-yl)(4-(diethylamino)-2-hydroxyphenyl)methyl)-N-cyclopentylbenzamide (Compound 52, NCK16);

N-cyclopentyl-3-((4-(2,3-dichlorophenyl)piperazin-1-yl)(4-(diethylamino)-2-hydroxyphenyl)methyl)benzamide (Compound 53, NCK18);

N-cyclopentyl-3-((4-(2,3-dichlorophenyl)piperazin-1-yl)(2-hydroxy-4,6-dimethoxyphenyl)methyl)benzamide (Compound 54, NCK19);

2-((4-chlorophenyl)(4-(4-chlorophenyl)piperazin-1-yl)methyl)phenol (Compound 55, NCK20);

2-((4-(4-chlorophenyl)piperazin-1-yl)(6-methylpyridin-3-yl)methyl)phenol (Compound 56, NCK21);

2-(o-tolyl(4-(p-tolyl)piperazin-1-yl)methyl)phenol (Compound 57, SG1);

2-((4-(p-tolyl) piperazin-1-yl)(4-(trifluoromethyl)phenyl) methyl)phenol (Compound 58, SG2);

N-cyclopentyl-4-((2-hydroxyphenyl)(4-(p-tolyl) piperazin-1-yl)methyl)benzamide (Compound 59, SG3);

2-((4-chlorophenyl)(4-(p-tolyl)piperazin-1-yl)methyl)phenol (Compound 60, SG4);

2-((3-methoxyphenyl)(4-(p-tolyl)piperazin-1-yl)methyl)phenol (Compound 61, SG5);

5-((2-hydroxyphenyl)(4-(p-tolyl)piperazin-1-yl)methyl)furan-2-carbaldehyde (Compound 62, SG6); and 2-((6-methylpyridin-3-yl)(4-(p-tolyl)piperazin-1-yl)methyl)phenol (Compound 63, SG7).

Compounds of general formula (I) may be prepared by reacting an aldehyde of general formula (II):

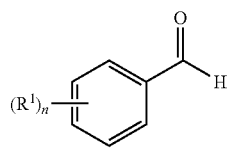
(II)

wherein $R^1$ and n are as defined for general formula (I); with a compound of general formula (III):

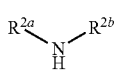
(III)

wherein $R^{2a}$ and $R^{2b}$ are as defined for general formula (I);

and a boronic acid of general formula (IV):

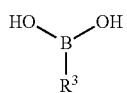
(IV)

wherein $R^3$ is as defined for general formula (I).

The reaction is a Petasis reaction, which is a 3-component boronic mannich-type reaction which uses boronic acids of general formula (IV) as a potential nucleophilic species to react with the salicylaldehyde derivative of general formula (II) and the amine of general formula (III) to form a new carbon-carbon bond. The Petasis reaction proceeds via the formation of an iminium species, which reacts with the boronic acid to yield tertiary amines.

Suitable reaction solvents include organic solvents, for example cyclic ethers such as dioxane.

Suitably, the process comprises:
i. reacting the compound of general formula (II) with the compound of general formula (III) to form a mixture comprising intermediate iminium species;
ii. reacting the product of step (i) with the compound of general formula (IV).

Suitably step (ii) is carried out at elevated temperature, for example 50 to 100° C., for example at the reflux temperature of the solvent. When the solvent is dioxane, this is about 85 to 95° C., typically about 90° C.

The product may be extracted into a second solvent such as ethyl acetate, dried and purified using standard methods such as described below in the examples.

Compounds of general formulae (II), (III) and (IV) are known and are commercially available or may be prepared using known methods.

Compounds of general formula (I) may also be prepared from other compounds of general formula (I). For example, a compound of general formula (I) in which $R^1$ is optionally substituted aryl or heteroaryl may be prepared from compounds of general formula (I) in which $R^1$ is halo by reaction with a compound of general formula (V):

(V)

wherein $R^{1a}$ is aryl or heteroaryl optionally substituted as defined for general formula (I).

The reaction may be carried out using a Suzuki coupling reaction over a palladium catalyst.

Compounds of general formula (V) are known and are commercially available or may be prepared using known methods.

The methods for preparing compounds of general formula (I) represent a further aspect of the present invention.

The compounds of general formula (I) are capable of inhibiting/downregulating/suppressing Bcl-2 associated death promoter (BAD) protein, particularly inhibiting/downregulating/suppressing phosphorylation of Bcl-2 associated death promoter (BAD) protein in a cancer cell. The inhibition/downregulation/suppression of BAD occurs without affecting the upstream Ser/Thr kinase called Akt/protein kinase B (PKB). Therefore, the compounds of general formula (I) preferentially inhibit/downregulate/suppresses phosphorylation of BAD.

The inhibition/downregulation of BAD is carried out by the compound of general formula (I) occupying the hydrophobic groove within the protein-protein interface of Bcl-2/BAD. Additionally, the compound of general formula (I) occupies an additional hydrophobic side pocket within the interface formed by the side-chains of Leu-97, Trp-144, and Phe-198 of the human protein with a dichlorophenyl moiety.

The compounds of formula (I) are potent inhibitors/downregulators of BAD in cancer cells, particularly breast cancer, endometrial cancer, ovarian cancer, liver cancer, colon cancer, prostate cancer and pancreatic cancer cells and induce apoptosis due to the downregulation/inhibition of BAD phosphorylation. Said compounds enhance cytotoxicity of cancer cells and carry out target specific downregulation/inhibition of BAD phosphorylation without affecting the upstream kinases.

The compounds of general formula (I) were screened for their anticancer activity against MCF7 cells and NPB (Compound 9) was found to be the most potent compound. NPB was subsequently evaluated against panel of normal immortalized mammary epithelial cells (MCF10A and MCF12A), normal hepatocytes (LO2), mammary carcinoma (BT549, MDA-MB-231, MCF7, T47D, BT474), endometrial cancer (Ishikawa, Ecc1, RL95-2, AN3), ovarian cancer (SK-OV-3, OVCAR-2, Caov-3, HEY C2, Ovca433), liver cancer (Hep3B, H2P, H2M), colon cancer (HCT116, DLD-1, Caco-2), prostate cancer (PC3, LNCaP, DU145) and pancreatic cancer (AsPC-1, BxPC-3) cells. NPB significantly enhanced apoptosis in all the tested cancer cell lines and NPB exhibited no substantial activity against normal hepatocytes and immortalized mammary epithelial cells. Using a Laplacian-modified Naïve Bayes classifier, NPB is subjected to in silico analysis which anticipates the human target of NPB as BAD protein.

NPB was found to induce apoptotic cell death in a range of carcinoma cells but did not have cytotoxic effect on normal (immortalized) epithelial cells.

The hallmark features of cells undergoing apoptosis are phosphatidylserine externalization, caspase activation and genomic DNA fragmentation. In an embodiment, NPB exhibits apoptosis against MCF7 cells using FITC-annexin-V and propidium iodide staining. FITC-annexin-V staining confirms the loss of membrane integrity and PI staining confirms the late apoptotic events and these results are correlated with caspase 3/7 activity.

Therefore in a further aspect of the invention, there is provided a compound of general formula (I) for use in medicine.

The compounds of general formula (I) are of particular use in the treatment of cancer, suitably, a cancer in which there is BAD phosphorylation.

In a further aspect, therefore, there is provided a compound of general formula (I) for use in the treatment of cancer.

Further, there is provided the use of a compound of general formula (I) in the preparation of an agent for the treatment of cancer.

There is also provided a method for the treatment of cancer, the method comprising administering to a patient in need of such treatment an effective amount of a compound of general formula (I).

The compounds are particularly useful for treating cancer in which there is BAD phosphorylation and, for example, the cancer may be breast cancer, endometrial cancer, ovarian cancer, liver cancer, colon cancer, prostate cancer or pancreatic cancer or other epithelial-derived cancers in which BAD is phosphorylated.

The compounds of general formula (I) are suitably administered in a pharmaceutical composition and therefore in a further aspect of the invention there is provided a pharmaceutical composition comprising a compound of general formula (I) and a pharmaceutically acceptable excipient.

The pharmaceutically acceptable excipient may be an adjuvant, diluent, carrier, granulating agent, binding agent, lubricating agent, disintegrating agent, sweetening agent, glidant, anti-adherent, anti-static agent, surfactant, anti-oxidant, gum, coating agent, coloring agent, flavouring agent, coating agent, plasticizer, preservative, suspending agent, emulsifying agent, plant cellulosic material, spheronization agent, other conventionally known pharmaceutically acceptable excipient or any combination of excipients thereof.

In another embodiment, the pharmaceutical composition of the present invention is formulated for intraperitoneal administration, hepatoportal administration, intravenous administration, intra articular administration, pancreatic duodenal artery administration or intramuscular administration, or any combination thereof.

The invention will now be described in greater detail with reference to the examples and to the drawings in which:

FIGS. 1(a) and 1(b) depict the $^1$H-NMR and $^{13}$C-NMR spectra of Compound 1.
FIG. 2 depicts the $^{13}$C-NMR spectra of compound 2.
FIGS. 3(a) and 3(b) depict the $^1$H-NMR and $^{13}$C-NMR spectra of Compound 3.
FIGS. 4(a) and 4(b) depict the $^1$H-NMR and $^{13}$C-NMR spectra of Compound 4.
FIGS. 5(a) and 5(b) depict the $^1$H-NMR and $^{13}$C-NMR spectra of Compound 5.
FIG. 6 depicts the $^1$H-NMR spectra of compound 6.
FIGS. 7(a) and 7(b) depict the $^1$H-NMR and $^{13}$C-NMR spectra of Compound 7.
FIG. 8 depicts the $^{13}$C-NMR spectra of Compound 8.
FIGS. 9(a) and 9(b) depict the $^1$H-NMR and LCMS spectra of Compound 9.
FIG. 10 depicts the $^1$H-NMR spectra of Compound 10.
FIG. 11: IC50 values of NPB in a range of carcinoma cell lines.
FIG. 12: NPB suppresses cell viability and promote apoptosis in carcinoma cell lines.

Effect of NPB (5 µM) on carcinoma cell viability including, mammary, endometrial, ovarian, liver, colon, prostate, and pancreatic carcinoma cell lines. (A) Cell viability (B) caspase 3/7 activities and (C) cytotoxicity were evaluated using ApoTox-Glo™ Triplex Assay Kit as described in methodology. Statistical significance was assessed by an unpaired two-tailed Student's t-test using GraphPad Prism5. The column represents mean of triplicate determinations; bars, ±SD. **$P<0.001$, *$P<0.05$. Note: RFU, relative fluorescence unit; RLU, relative luminescence unit, #; non-transformed, immortalized epithelial cells; MB-231, MDA-MB-231.

FIG. 13: NPB stimulates apoptotic cell death in MCF7 cells.

(A) Apoptotic cell death of MCF7 cells measured after treatment with 10 µM NPB using flow cytometry analysis. Annexin V-FITC staining is indicated on the X-axis and PI staining on the Y-axis. The lower left quadrant represents live cells, the lower right quadrant represents early apoptotic cells, the upper left quadrant represents necrotic cells, and the upper right quadrants display late apoptotic cells. Acquisition of Annexin V and PI data were represented as a percentage (%) in each quadrant. (B) Cell cycle analysis of MCF7 cells measured after treatment with 10 µM NPB using flow cytometry analysis. (C) Cell viability of performed colonies generated by MCF7 cell after exposure to NPB or DMSO cultured 14 days in 3D Matrigel using AlamarBlue® viability assay. Microscopic visualization (below) of Calcein AM stained colonies generated by MCF7 cells after exposure to NPB or DMSO cultured in 3D Matrigel. (D) Cell viability in colonies generated by MCF7 cell after exposure to NPB or DMSO cultured in Soft agar using AlamarBlue® viability assay. (E) Crystal Violet staining of foci colonies generated by MCF7 cells after exposure to NPB or DMSO. All assays performed as described in methodology. Statistical significance was assessed by an unpaired two-tailed Student's t-test using GraphPad Prism5. The column represents mean of triplicate determinations; bars, ±SD. **$P<0.001$, *$P<0.05$.

FIG. 14: Cheminformatics and surface plasmon resonance (SPR) analysis predicts an interaction of NPB compound to BAD protein.

(A) Sensorgrams obtained by SPR analysis of NPB with the BAD protein subunit. The BAD protein subunit was immobilized onto the surface of a CM5 sensor chip. A solution of NPB at variable concentrations (20-100 µM) was injected to generate result binding responses (RU) recorded as a function of time (sec). The results were analyzed using BIA evaluation 3.1. (B) Western blot (WB) analysis was used to assess the level of Ser99 phosphorylation of BAD in MCF7 cells after treatment with NPB. (Below) Calculated $IC_{50}$ of NPB from dose-response for BAD phosphorylation (Ser99), BAD and β-ACTIN as in shown above by use of ImageJ software from NIH, USA (http://imagej.nih.gov/ij/). (C) WB analysis was used to assess the level of a multiple proteins involved upstream of BAD in MCF7 cells after treatment with NPB. (D) WB analysis was used to assess the level of a multiple protein involved cell survival and cell proliferation in MCF7 cells after treatment with NPB. For WB analysis, soluble whole cell extracts were run on an SDS-PAGE and immunoblotted as described in methodology. β-ACTIN (ACTB) was used as an input control for cell lysate. The sizes of detected protein bands in kDa are shown on the left side.

FIG. 15: NPB specifically inhibits phosphorylation of BAD (at Ser99) in carcinoma cell lines independent of AKT signalling (A) WB analysis was used to assess the levels of phosphorylated human BAD (at Ser75 and Ser99) and BAD protein in the range of carcinoma cell lines, including mammary, ovarian, pancreatic, endometrial, hepatocellular, colon and prostate cancer after treatment with NPB (5 µM). Total BAD was used as an input control for cell lysate. (B) WB analysis was used to assess the levels of pBAD (Ser99) and pAKT (Ser473), AKT and BAD in MCF7, Caov-3, Ishikawa, and AsPC-1 cells. 5 µM each of AKT inhibitor (IV) and NPB was used to treat cells. Depletion of AKT expression was achieved using transient-transfection of short hairpin (sh)-RNA (1&2) directed to AKT transcript as described in methodology. β-ACTIN was used as an input control for cell lysate. For WB analysis, soluble whole cell extracts were run on an SDS-PAGE and immunoblotted as described in materials methodology. The sizes of detected protein bands in kDa are shown on the left side. Note: #; non-transformed immortalized-cell line.

FIG. 16: siRNA-mediated depletion of BAD expression prevents the effect of NPB in carcinoma cell lines.

(A) WB analysis was used to assess the levels of pBAD (Ser99) activity and BAD protein in MCF7, BT474, Caov-3, Ishikawa, AsPC-1, and DLD-1 cells after treatment with 5 µM NPB. Depletion of BAD expression was achieved using transient-transfection of small interfering (si)-RNA directed to the BAD transcript. Soluble whole cell extracts were run on an SDS-PAGE and immunoblotted as described in materials and methods. β-ACTIN was used as input control. Effects of NPB (5 µM) in MCF7, BT474, Caov-3, Ishikawa, AsPC-1, and DLD-1 cells. (B) Cell viability and (C) caspase 3/7 activities were evaluated using the ApoTox-Glo™ Triplex Assay Kit. All assays performed as described in methodology. Statistical significance was assessed by an unpaired two-tailed Student's t-test (P<0.05 was considered as significant) using GraphPad Prism5. The column represents mean of triplicate determinations; bars, ±SD. **P<0.001, *P<0.05. Note RFU, relative fluorescence unit; RLU, relative luminescence unit.

FIG. 17: NPB inhibits phosphorylation of BAD Ser99 in mammary carcinoma and inhibits tumour growth (A) Measurement of tumour volume in BALB/c-nu female mice as described in materials and methods. Animals (n=5 each group) were treated with vehicle, 5 mg/kg NPB or 20 mg/kg NPB, and relative tumour burden was recorded. Animal weight was measured daily for the duration of the experiment. (B) Tumours were excised after the NPB treatment regime and weighed. Representative resected tumours are shown in the right side. (C) WB of tumour tissue to determine levels of p-BAD (Ser99) and BAD. Soluble whole cell extracts were run on an SDS-PAGE and immunoblotted as described in methodology. β-ACTIN was used as an input control. The sizes of detected protein bands in kDa are shown on the left side. (D) Histological analyses of phospho-BAD, BAD, Ki67 and TUNEL staining. Tumour tissue sections were immunolabeled with goat anti-pBAD (Ser 136) polyclonal antibody (Santa Cruz Biotechnology), mouse anti-BAD monoclonal (Santa Cruz Biotechnology) and anti-Ki67 antibody (Abcam, ab15580) and stained with hematoxylin. Apoptotic DNA fragmentation was detected using TUNEL Apoptosis Detection Kit (Gen Script USA Inc.) as described in methodology. Statistical significance was assessed by an unpaired two-tailed Student's t-test (P<0.05 was considered as significant) using GraphPad Prism5. The point represents mean of triplicate experiments; bars, ±SD. **P<0.001, *P<0.05.

FIG. 18:

(A) Western blot analysis was used to assess the level of BAD Ser99 phosphorylation of pBAD, BAD, pAKT, and AKT in MCF7 cells after an increasing period of treatment with NPB (10 µM). Soluble whole cell extracts were run on an SDS-PAGE and immunoblotted as described in methodology. The sizes of detected protein bands in kDa are shown on the left side. (B) Kinases and phosphorylated substrates were detected using a Western Blot array (Proteome Profiler Human Phospho-Kinase Array Kit. MCF7 cells treated with NPB (10 µM) or DMSO for 12 h at 37° C. before preparation of cell lysate. Mean pixel density was analysed using ImageJ software and is represented below.

Figure 1A:
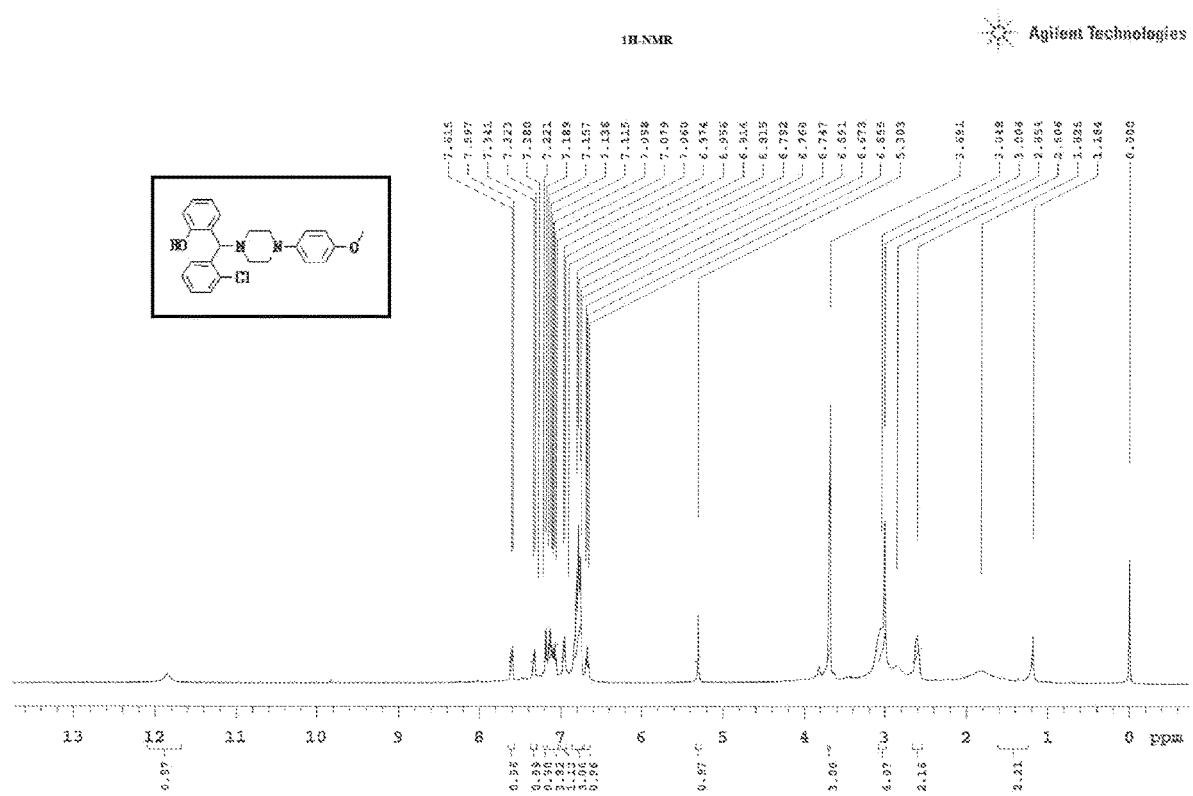

FIGS. 22A, 22B, 22C, 22D and 22E: $IC_{50}$ values of NPB structure-based analogues in a carcinoma cell lines.

Note: NV, no value

MATERIALS EMPLOYED TO ARRIVE AT THE EXAMPLES OF THE PRESENT DISCLOSURE

Cell Culture and Reagents—

The human immortalized mammary epithelial cell lines, MCF10A, and MCF12A; and immortalized hepatocellular epithelial cell line, LO2 were obtained from the American Type Culture Collection (ATCC, Rockville, Md.) and were cultured as per ATCC propagation instructions. MC cell lines, MCF7, T47D, BT474, BT549, and MDA-MB-231 (denoted as MB-231); endometrial carcinoma cell lines, Ishikawa, ECC1, RL95-2 and AN3; hepatocellular carcinoma cell lines, Hep3B, H2P, and H2M; colon carcinoma cell lines, HCT116, DLD-1, and Caco-2; and prostate carcinoma cell lines, PC3, LNCaP, DU145 were obtained from the American Type Culture Collection (ATCC, Rockville, Md.). Ovarian carcinoma cell lines, SK-OV-3, OVCAR-2, Caov-3, HEY C2, and Ovca433 were obtained from Dr Ruby Huang's laboratory at The Cancer Science Institute of Singapore, National University of Singapore (NUS). Pancreatic carcinoma cell lines were obtained from Prof. H. Phillip Koeffler's laboratory at The Cancer Science Institute of Singapore, National University of Singapore (NUS). All carcinoma cell lines were cultured as per ATCC propagation instructions. AKT inhibitor IV was purchased from Calbiochem (San Diego, Calif., USA). BAD directed stealth (sh)-RNA-BAD (shRNA-BAD1, 5'-GCUCCGCAC-CAUGAGUGACGAGUUU-3' and shRNA-BAD2, 5'AAA-CUCGUCACUCAUCCUCCGGAGC3') was purchased from Life Technologies (Singapore). AKT directed shRNA (shRNA-AKT1, 5'-CCGGCGCGTGACCAT-GAACGAGTTTCTCGAGAAACTCGTTCATGGT-CACGCGTTTTTG-3' and shRNA2-AKT, 5'-CCGGGGACTACCTGCACTCG-GAGAACTCGAGTTCTCCGAGTGCAGGTAGT CCTTTTTG-3') was purchased from Life Technologies (Singapore), and cloned in to PLKO.1 vector (Sigma, Singapore). Cells were transiently-transfected with 20 nM shRNA (AKT or BAD) or universal negative control (Invitrogen, Carlsbad, Calif., USA) using FuGENE HD (Promega) for 24 h and further assays performed. Alanine transaminase (ALT), aspartate transaminase (AST), lactate dehydrogenase (LDH), creatine kinase (CK), blood urea nitrogen (BUN) commercial kits were purchased from AGAPPE Diagnostics Ltd, Kerala, India.

Example 1

Synthesis and Characterization of Formula I Compounds
General Synthesis of Compound of Formula I Piperazines (0.8 mmol) and salicylaldehyde (0.8 mmol) are taken in an RBF and stirred for about 10 minutes using Dioxane as solvent. After about 10 minutes, Aryl boronic acid (0.8 mmol) is added to the mixture and refluxed with continuous stirring for about 8 hours using Dioxane as solvent on a hot plate maintained at about 90° C. After about 8 hours, ethyl acetate and water are added to the reaction mixture and the ethyl acetate layer is separated using separating funnel and dried over anhydrous sodium sulfate. Ethyl acetate is evaporated to obtain the product. The desired phenolic compound product is obtained by separation using column chromatography.

The specific reagents used to obtain Compounds 1 to 15 and 41 to 63 are provided in Table 1 below.

TABLE 1

| No | Salicylaldehyde | Piperazine | Aryl boronic acid | Product |
|---|---|---|---|---|
| 1 | | | | |
| 2 | | | | |
| 3 | | | | |
| 4 | | | | |

TABLE 1-continued

| No | Salicylaldehyde | Piperazine | Aryl boronic acid | Product |
|---|---|---|---|---|
| 5 | | | | |
| 6 | | | | |
| 7 | | | | |
| 8 | | | | |
| 9 | | | | |
| 10 | | | | |
| 11 | | | | |

TABLE 1-continued

| No | Salicylaldehyde | Piperazine | Aryl boronic acid | Product |
|---|---|---|---|---|
| 12 | | | | |
| 13 | | | | |
| 14 | | | | |
| 15 | | | | |
| 41 | | | | Molecular Weight: 490.0363 |
| 42 | | | | Molecular Weight: 447.7846 |

TABLE 1-continued

| No | Salicylaldehyde | Piperazine | Aryl boronic acid | Product |
|----|---|---|---|---|
| 43 | 2-hydroxybenzaldehyde | 1-(2,3-dichlorophenyl)piperazine | 3-methoxyphenylboronic acid | Molecular Weight: 443.3656 |
| 44 | 2-hydroxybenzaldehyde | 1-(2,3-dichlorophenyl)piperazine | 5-acetylthiophene-2-boronic acid | Molecular Weight: 461.4040 |
| 45 | 2-hydroxybenzaldehyde | 1-(2,3-dichlorophenyl)piperazine | naphthalen-1-ylboronic acid | Molecular Weight: 463.3983 |
| 46 | 2-hydroxybenzaldehyde | 1-(2,3-dichlorophenyl)piperazine | 5-formylfuran-2-boronic acid | Molecular Weight: 431.3118 |

TABLE 1-continued

| No | Salicylaldehyde | Piperazine | Aryl boronic acid | Product |
|---|---|---|---|---|
| 47 | salicylaldehyde | 1-(2,3-dichlorophenyl)piperazine | 2-fluoro-3-methylpyridin-4-yl boronic acid | Molecular Weight: 448.3606 |
| 48 | salicylaldehyde | 1-(2,3-dichlorophenyl)piperazine | 4-(trifluoromethyl)phenylboronic acid | Molecular Weight: 481.338 |
| 49 | salicylaldehyde | 1-(2,3-dichlorophenyl)piperazine | 6-chloro-5-methylpyridin-3-yl boronic acid | Molecular Weight: 462.7993 |
| 50 | salicylaldehyde | 1-(2,3-dichlorophenyl)piperazine | pyridin-3-yl boronic acid | Molecular Weight: 414.3276 |
| 51 | salicylaldehyde | 1-(4-chlorophenyl)piperazine | 5-acetylthiophen-2-yl boronic acid | Molecular Weight: 426.9589 |

TABLE 1-continued

| No | Salicylaldehyde | Piperazine | Aryl boronic acid | Product |
|---|---|---|---|---|
| 52 | | | | Molecular Weight: 561.16 |
| 53 | | | | Molecular Weight: 595.60 |
| 54 | | | | Molecular Weight: 584.53 |
| 55 | | | | Molecular Weight: 413.34 |
| 56 | | | | |

TABLE 1-continued

| No | Salicylaldehyde | Piperazine | Aryl boronic acid | Product |
|---|---|---|---|---|
| 58 | (2-hydroxybenzaldehyde) | (1-(p-tolyl)piperazine) | (4-(trifluoromethyl)phenylboronic acid) | Molecular Weight: 426.4740 |
| 57 | (2-hydroxybenzaldehyde) | (1-(p-tolyl)piperazine) | (o-tolylboronic acid) | Molecular Weight: 372.5026 |
| 59 | (2-hydroxybenzaldehyde) | (1-(p-tolyl)piperazine) | (2-hydroxyphenylboronic acid) | (N-cyclopentyl benzamide product) |
| 61 | (2-hydroxybenzaldehyde) | (1-(p-tolyl)piperazine) | (3-methoxyphenylboronic acid) | Molecular Weight: 388.5020 |
| 60 | (2-hydroxybenzaldehyde) | (1-(p-tolyl)piperazine) | (4-chlorophenylboronic acid) | Molecular Weight: 392.9211 |

TABLE 1-continued

| No | Salicylaldehyde | Piperazine | Aryl boronic acid | Product |
|---|---|---|---|---|
| 62 | CHO, OH (salicylaldehyde) | HN-piperazine-p-tolyl | 5-formylfuran-2-boronic acid | Product; Molecular Weight: 364.4806 |
| 63 | CHO, OH (salicylaldehyde) | HN-piperazine-p-tolyl | 6-methylpyridine-3-boronic acid | Product; Molecular Weight: 373.4907 |

The compounds shown in Table 2 were obtained by reacting NPB bromide (see column 1 of Table 2) with a boronic acid using a palladium catalysed Suzuki coupling reaction as shown in Scheme 1.

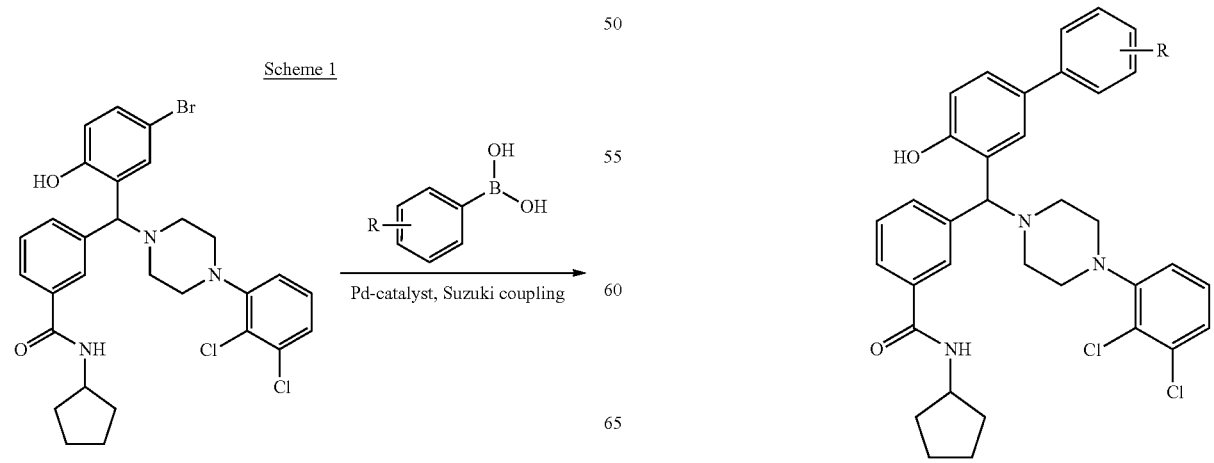

Scheme 1

TABLE 2
| NPB-Br | Boronic acid | Product |
|---|---|---|
| 16 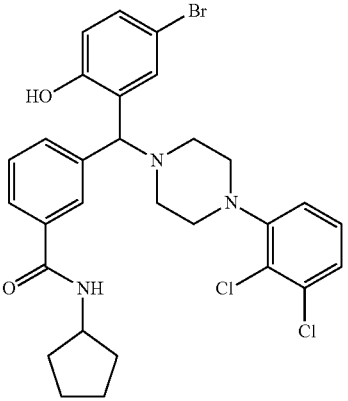 [SMILES: O=C(NC1CCCC1)c1cccc(C(c2cc(Br)ccc2O)N2CCN(c3cccc(Cl)c3Cl)CC2)c1] | 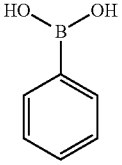 | 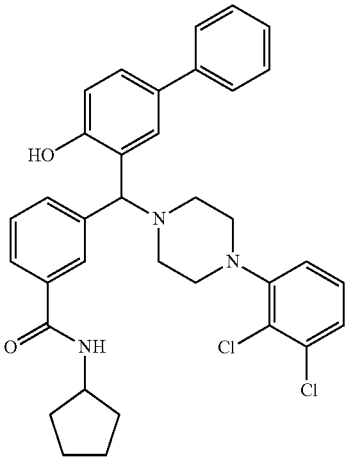 [SMILES: O=C(NC1CCCC1)c1cccc(C(c2cc(-c3ccccc3)ccc2O)N2CCN(c3cccc(Cl)c3Cl)CC2)c1] |
| 17 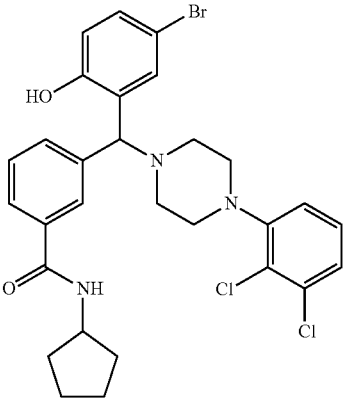 [SMILES: O=C(NC1CCCC1)c1cccc(C(c2cc(Br)ccc2O)N2CCN(c3cccc(Cl)c3Cl)CC2)c1] | 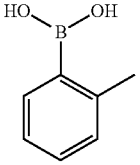 | 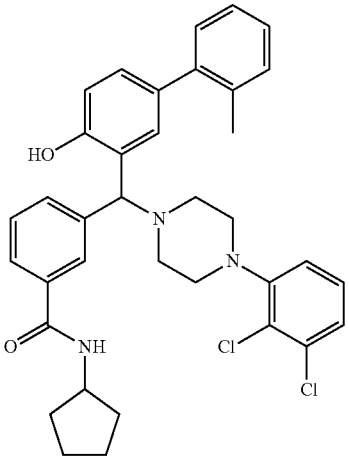 [SMILES: Cc1ccccc1-c1ccc(O)c(C(c2cccc(C(=O)NC3CCCC3)c2)N2CCN(c3cccc(Cl)c3Cl)CC2)c1] |
| 18 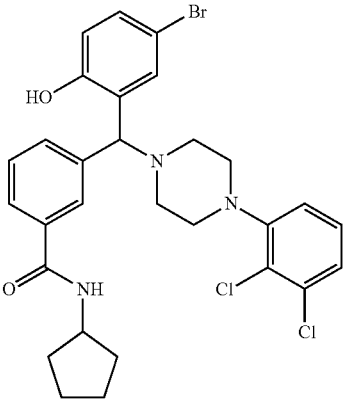 [SMILES: O=C(NC1CCCC1)c1cccc(C(c2cc(Br)ccc2O)N2CCN(c3cccc(Cl)c3Cl)CC2)c1] | 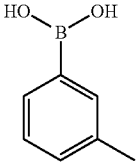 | 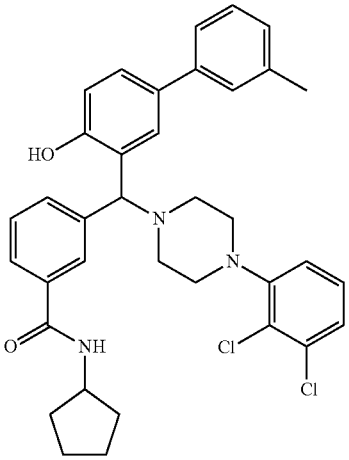 [SMILES: Cc1cccc(-c2ccc(O)c(C(c3cccc(C(=O)NC4CCCC4)c3)N3CCN(c4cccc(Cl)c4Cl)CC3)c2)c1] |

TABLE 2-continued

| NPB-Br | Boronic acid | Product |
|---|---|---|
| 19 | | |
| 20 | | |
| 21 | | |

TABLE 2-continued
| NPB-Br | Boronic acid | Product |
|---|---|---|
| 22 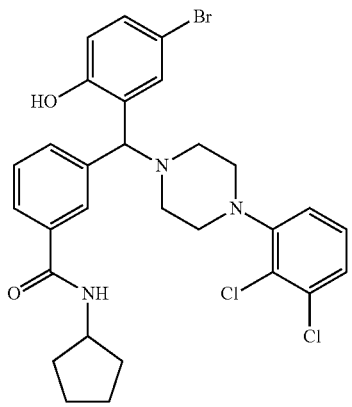 [SMILES: O=C(NC1CCCC1)c1cccc(C(c2cc(Br)ccc2O)N2CCN(c3cccc(Cl)c3Cl)CC2)c1] | 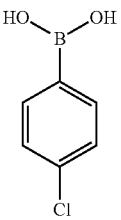 | 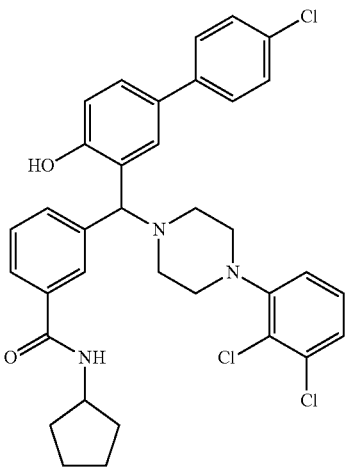 [SMILES: O=C(NC1CCCC1)c1cccc(C(c2cc(-c3ccc(Cl)cc3)ccc2O)N2CCN(c3cccc(Cl)c3Cl)CC2)c1] |
| 23 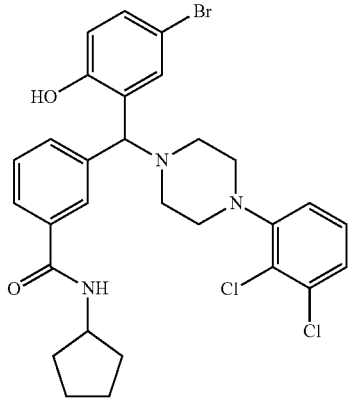 [SMILES: O=C(NC1CCCC1)c1cccc(C(c2cc(Br)ccc2O)N2CCN(c3cccc(Cl)c3Cl)CC2)c1] | 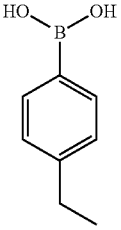 | 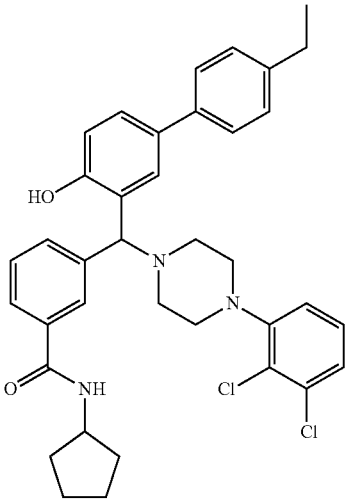 [SMILES: CCc1ccc(-c2ccc(O)c(C(c3cccc(C(=O)NC4CCCC4)c3)N3CCN(c4cccc(Cl)c4Cl)CC3)c2)cc1] |
| 24 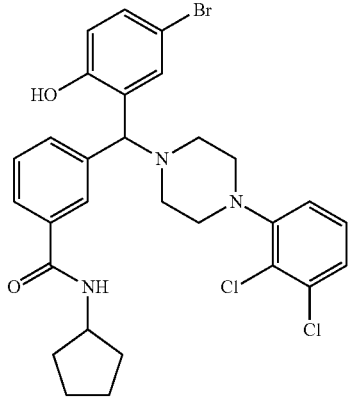 [SMILES: O=C(NC1CCCC1)c1cccc(C(c2cc(Br)ccc2O)N2CCN(c3cccc(Cl)c3Cl)CC2)c1] | 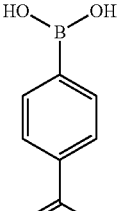 | 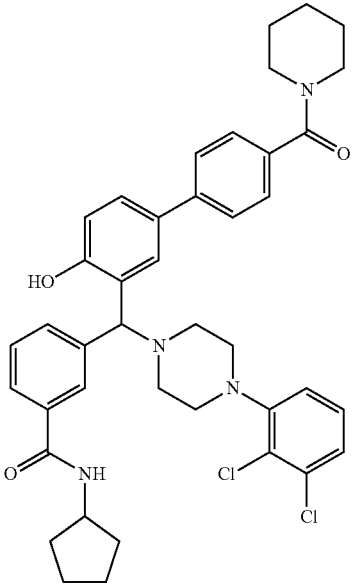 [SMILES: O=C(NC1CCCC1)c1cccc(C(c2cc(-c3ccc(C(=O)N4CCCCC4)cc3)ccc2O)N2CCN(c3cccc(Cl)c3Cl)CC2)c1] |

TABLE 2-continued
| NPB-Br | Boronic acid | Product |
|---|---|---|
| 25 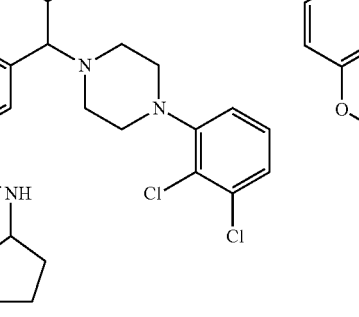 | 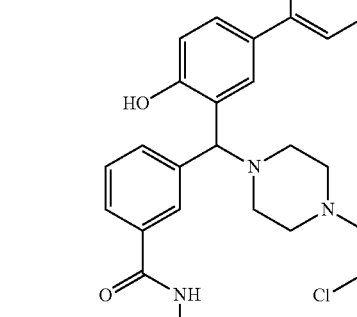 | 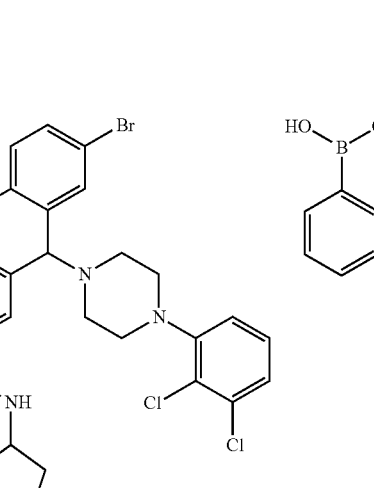 |
| 26 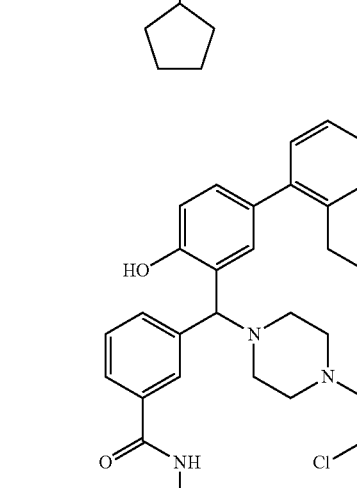 | 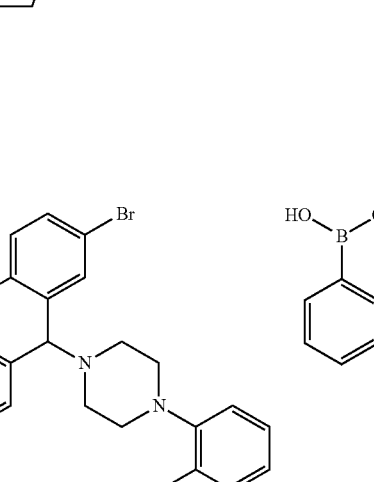 | 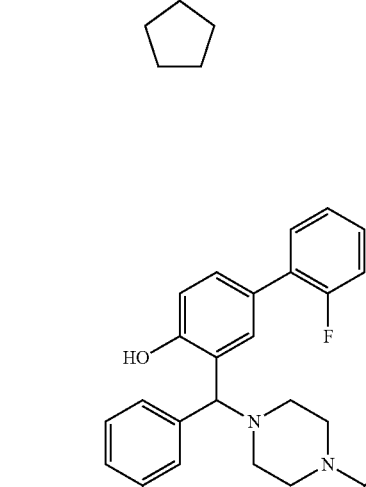 |
| 27 | | |

TABLE 2-continued
| NPB-Br | Boronic acid | Product |
|---|---|---|
| 28 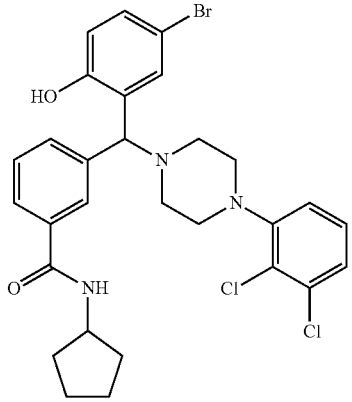 [SMILES: O=C(NC1CCCC1)c1cccc(C(c2cc(Br)ccc2O)N2CCN(c3cccc(Cl)c3Cl)CC2)c1] | 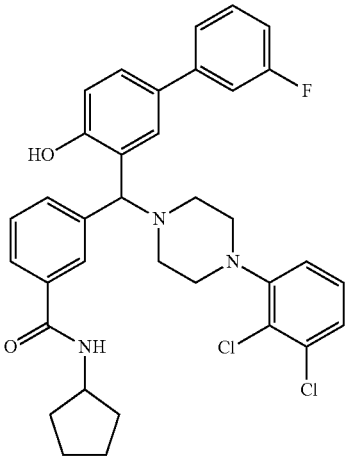 [SMILES: O=C(NC1CCCC1)c1cccc(C(c2cc(-c3cccc(F)c3)ccc2O)N2CCN(c3cccc(Cl)c3Cl)CC2)c1] | 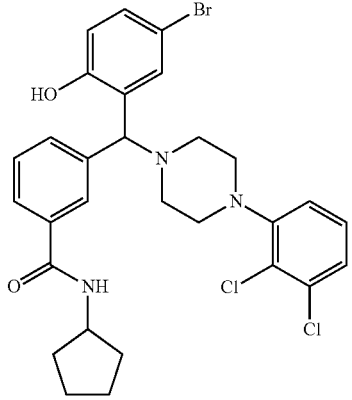 [SMILES: O=C(NC1CCCC1)c1cccc(C(c2cc(Br)ccc2O)N2CCN(c3cccc(Cl)c3Cl)CC2)c1] |
| 29 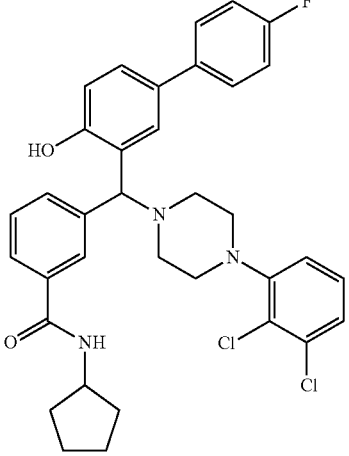 | 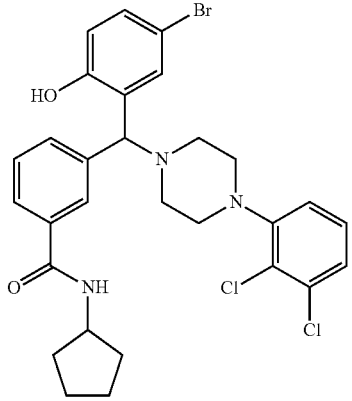 [SMILES: O=C(NC1CCCC1)c1cccc(C(c2cc(Br)ccc2O)N2CCN(c3cccc(Cl)c3Cl)CC2)c1] | 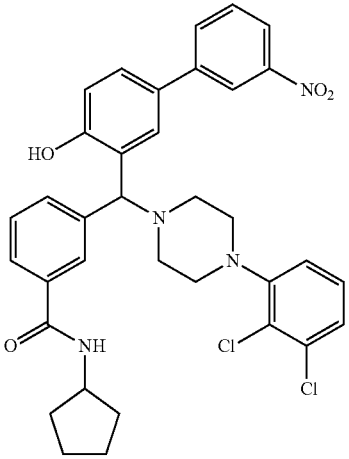 [SMILES: O=C(NC1CCCC1)c1cccc(C(c2cc(-c3cccc([N+](=O)[O-])c3)ccc2O)N2CCN(c3cccc(Cl)c3Cl)CC2)c1] |
| 30 | | |

TABLE 2-continued
| NPB-Br | Boronic acid | Product |
| --- | --- | --- |
| 31 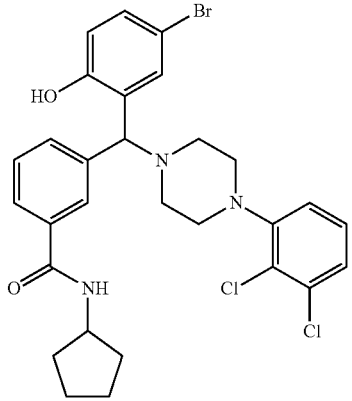 [SMILES: O=C(NC1CCCC1)c1cccc(C(c2cc(Br)ccc2O)N2CCN(c3cccc(Cl)c3Cl)CC2)c1] | 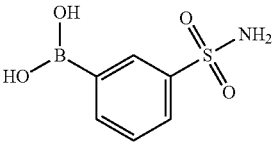 [SMILES: NS(=O)(=O)c1cccc(B(O)O)c1] | 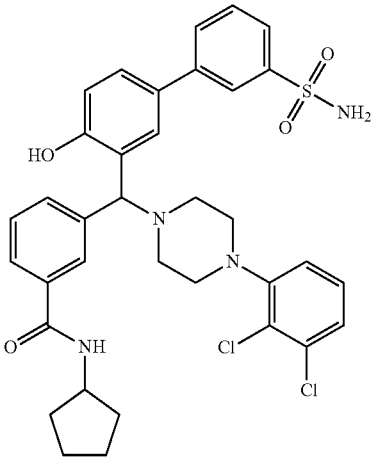 [SMILES: NS(=O)(=O)c1cccc(-c2ccc(O)c(C(c3cccc(C(=O)NC4CCCC4)c3)N3CCN(c4cccc(Cl)c4Cl)CC3)c2)c1] |
| 32 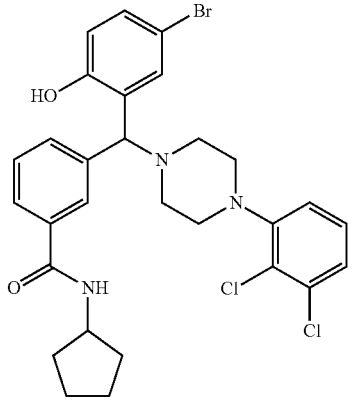 [SMILES: O=C(NC1CCCC1)c1cccc(C(c2cc(Br)ccc2O)N2CCN(c3cccc(Cl)c3Cl)CC2)c1] | 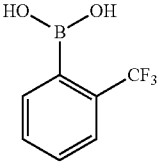 [SMILES: OB(O)c1ccccc1C(F)(F)F] | 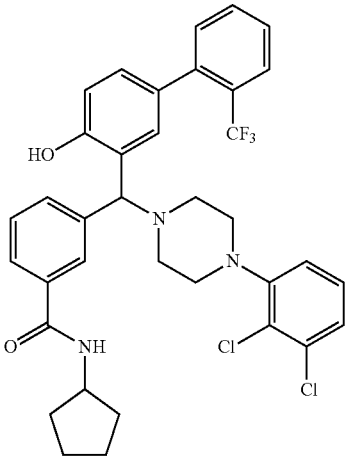 [SMILES: O=C(NC1CCCC1)c1cccc(C(c2cc(-c3ccccc3C(F)(F)F)ccc2O)N2CCN(c3cccc(Cl)c3Cl)CC2)c1] |
| 33 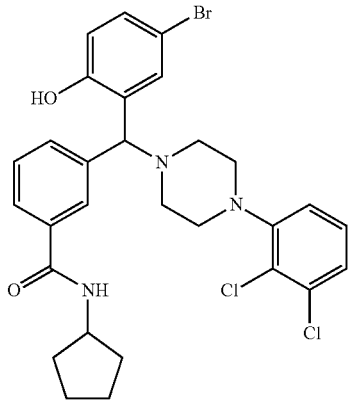 [SMILES: O=C(NC1CCCC1)c1cccc(C(c2cc(Br)ccc2O)N2CCN(c3cccc(Cl)c3Cl)CC2)c1] | 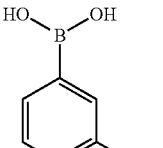 | 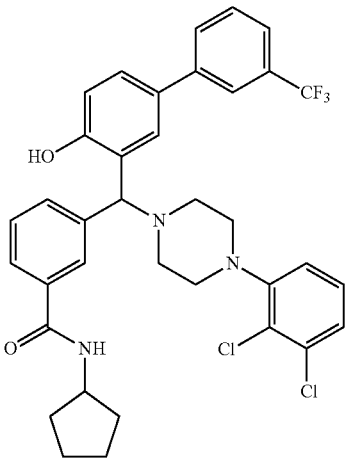 [SMILES: O=C(NC1CCCC1)c1cccc(C(c2cc(-c3cccc(C(F)(F)F)c3)ccc2O)N2CCN(c3cccc(Cl)c3Cl)CC2)c1] |

TABLE 2-continued
| NPB-Br | Boronic acid | Product |
|---|---|---|
| 34 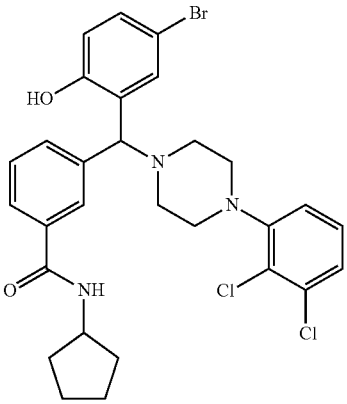 [SMILES: O=C(NC1CCCC1)c1cccc(C(c2cc(Br)ccc2O)N2CCN(c3cccc(Cl)c3Cl)CC2)c1] | 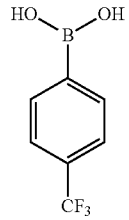 | 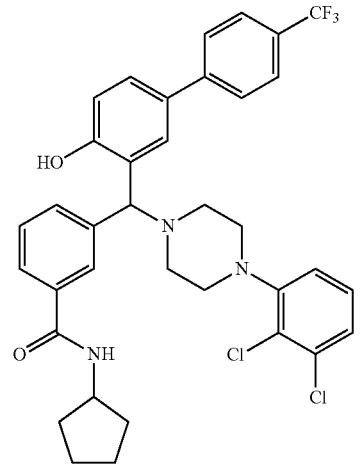 [SMILES: O=C(NC1CCCC1)c1cccc(C(c2cc(-c3ccc(C(F)(F)F)cc3)ccc2O)N2CCN(c3cccc(Cl)c3Cl)CC2)c1] |
| 35 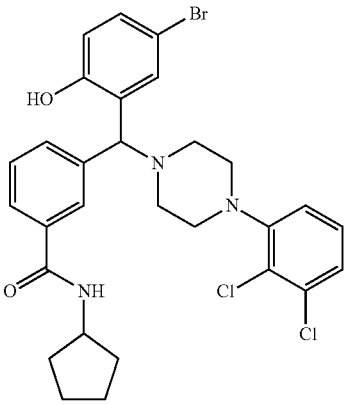 [SMILES: O=C(NC1CCCC1)c1cccc(C(c2cc(Br)ccc2O)N2CCN(c3cccc(Cl)c3Cl)CC2)c1] | 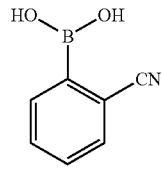 | 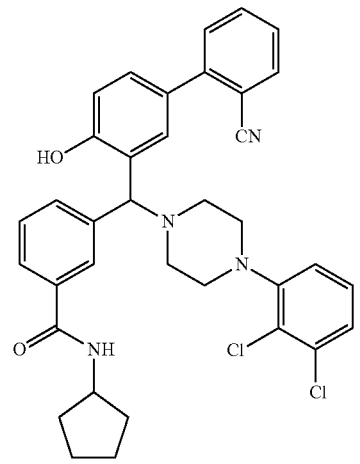 [SMILES: N#Cc1ccccc1-c1ccc(O)c(C(c2cccc(C(=O)NC3CCCC3)c2)N2CCN(c3cccc(Cl)c3Cl)CC2)c1] |
| 36 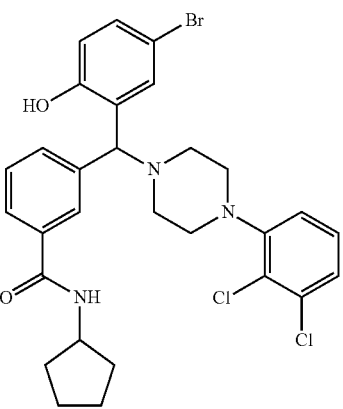 [SMILES: O=C(NC1CCCC1)c1cccc(C(c2cc(Br)ccc2O)N2CCN(c3cccc(Cl)c3Cl)CC2)c1] | 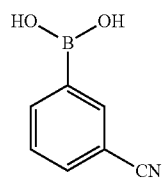 [SMILES: N#Cc1cccc(B(O)O)c1] | 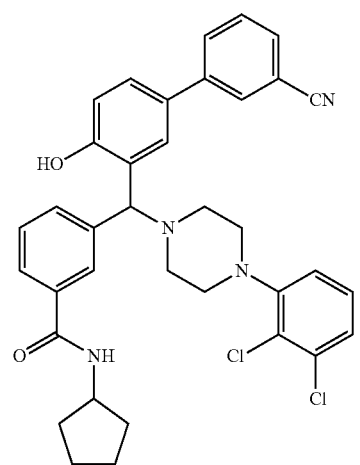 [SMILES: N#Cc1cccc(-c2ccc(O)c(C(c3cccc(C(=O)NC4CCCC4)c3)N3CCN(c4cccc(Cl)c4Cl)CC3)c2)c1] |

TABLE 2-continued
| NPB-Br | Boronic acid | Product |
|---|---|---|
| 37 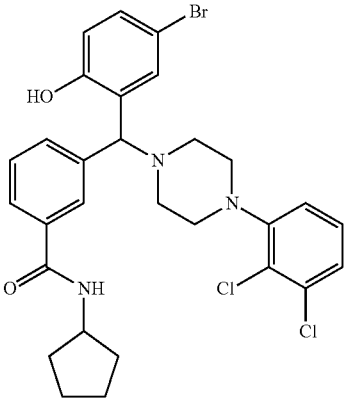 [SMILES: O=C(NC1CCCC1)c1cccc(C(c2cc(Br)ccc2O)N2CCN(c3cccc(Cl)c3Cl)CC2)c1] | 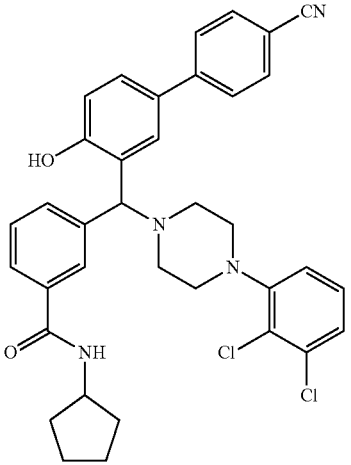 [SMILES: N#Cc1ccc(-c2ccc(O)c(C(c3cccc(C(=O)NC4CCCC4)c3)N3CCN(c4cccc(Cl)c4Cl)CC3)c2)cc1] | 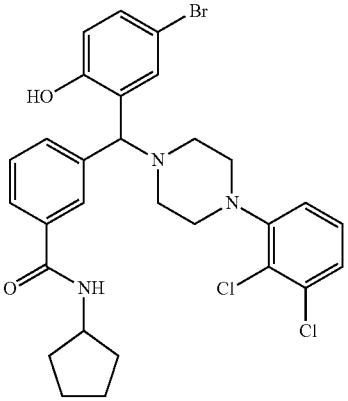 [SMILES: O=C(NC1CCCC1)c1cccc(C(c2cc(Br)ccc2O)N2CCN(c3cccc(Cl)c3Cl)CC2)c1] |
| 38 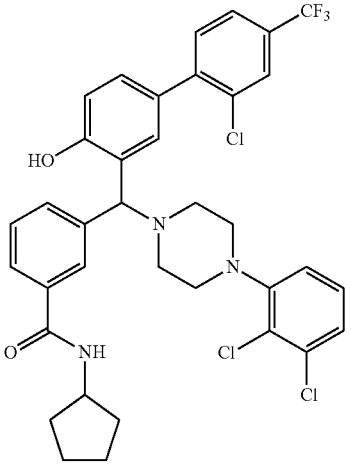 [SMILES: O=C(NC1CCCC1)c1cccc(C(c2cc(-c3ccc(C(F)(F)F)cc3Cl)ccc2O)N2CCN(c3cccc(Cl)c3Cl)CC2)c1] | 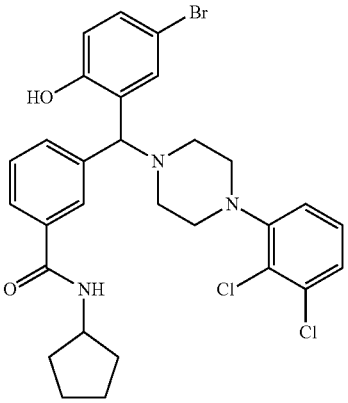 [SMILES: O=C(NC1CCCC1)c1cccc(C(c2cc(Br)ccc2O)N2CCN(c3cccc(Cl)c3Cl)CC2)c1] | 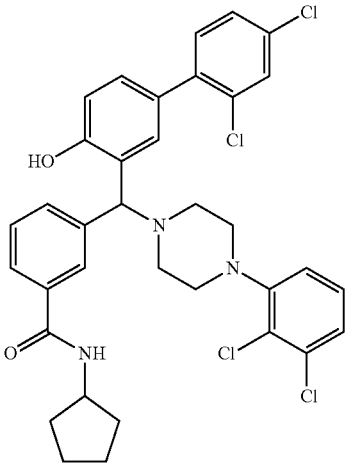 [SMILES: O=C(NC1CCCC1)c1cccc(C(c2cc(-c3ccc(Cl)cc3Cl)ccc2O)N2CCN(c3cccc(Cl)c3Cl)CC2)c1] |
| 39 | | |

TABLE 2-continued

| NPB-Br | Boronic acid | Product |
|---|---|---|
| 40 | | |

Figure 1B:
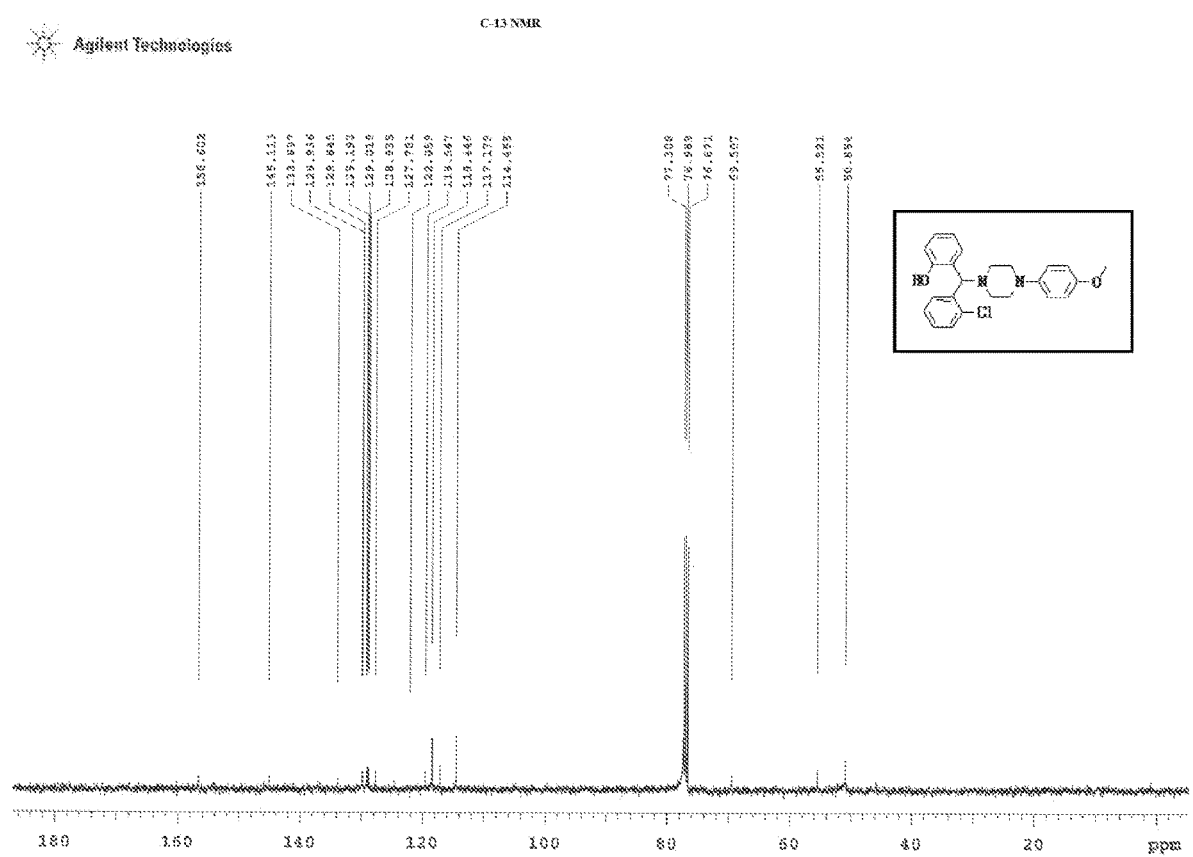

Characterization of Compound 1:

¹H NMR (CDCl₃, 400 MHz) δ: 3.691 (s, 3H), 5.303 (s, 1H, C—H), 1.184-3.691 (m, 8H-piperazine protons), 7.597-7.615 (d, 1H, J=7.2 Hz), 7.341-7.323 (d, 1H, J=7.2 Hz), 7.060-7.189 (m, 4H—ArH), 6.555-6.815 (m, 5H—ArH), 6.956-6.974, (d, 1H, J=7.2 Hz) 11.85 (s, 1H—OH brd peak); ¹³C NMR (400 MHz, CDCl3) δ: 50.854, 55.521, 69.50, 114.45, 117.17, 118.44, 119.547, 122.05, 127.78, 128.83, 129.01, 129.19, 129.84, 129.93, 133.89, 145.11, 156.60; Melting point 120-124° C. (FIG. 1)

Figure 2:
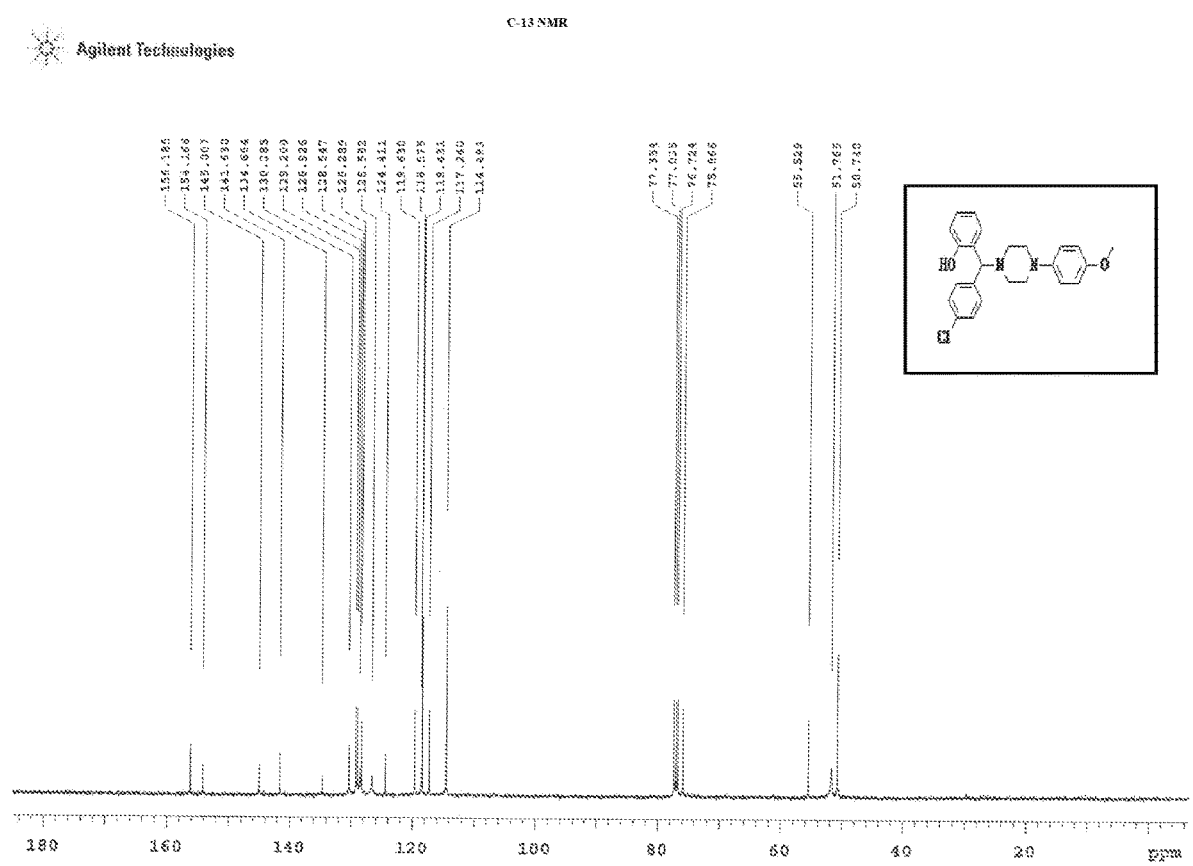

Characterization of Compound 2:

¹H NMR (CDCl₃, 400 MHz) δ: 2.539-3.065 (m, 8H), 3.674 (s, 3H), 4.359 (s, 1H), 6.651 (m, 1H), 6.740-6.804 (m, 5H), 6.855-6.872 (d, 1H, J=6.8 Hz), 7.086 (m, 1H), 7.165 (m, 2H), 7.280 (m, 1H), 7.361 (m, 1H); ¹³C NMR (400 MHz, CDCl3) δ: 50.74, 51.76, 55.52, 75.86, 114.49, 117.24, 118.43, 119.62, 124.41, 126.58, 128.28, 128.54, 128.92, 129.20, 130.28, 134.66, 141.63, 145.07, 154, 156.18; Melting point 85-89° C. (FIG. 2)

Figure 3A:
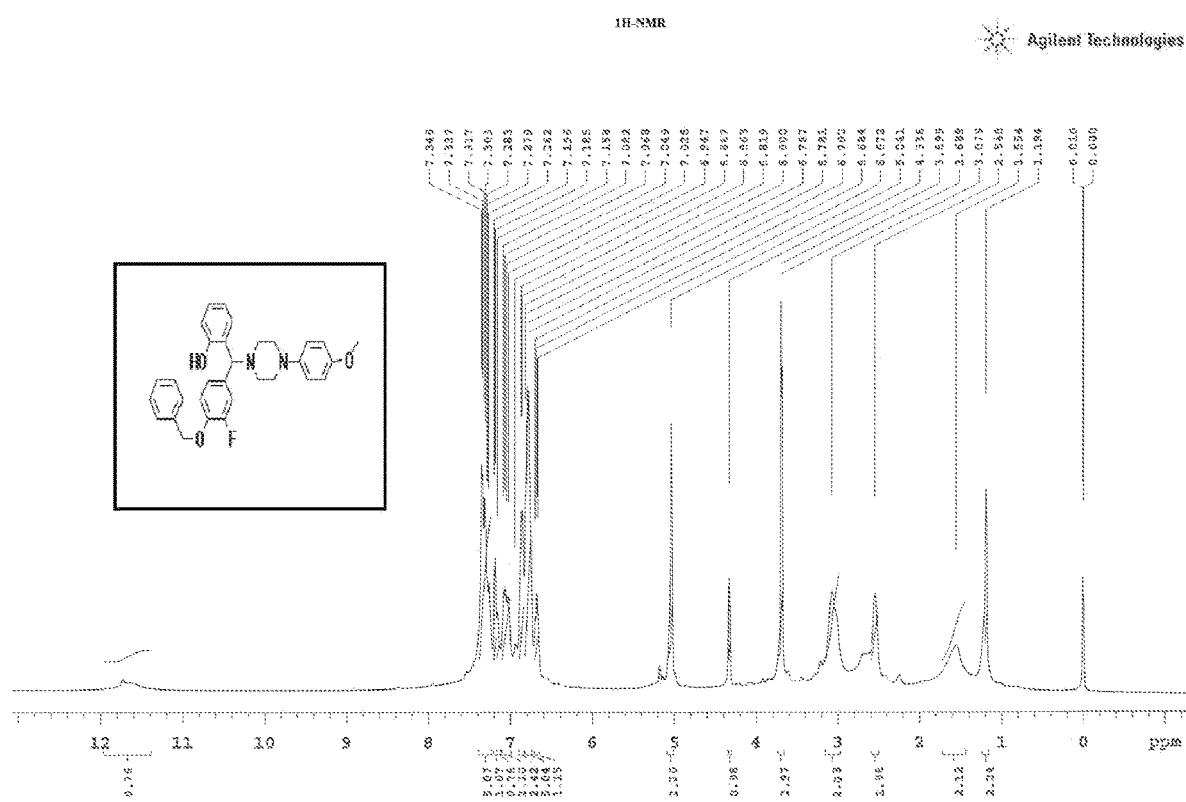
Figure 3B:
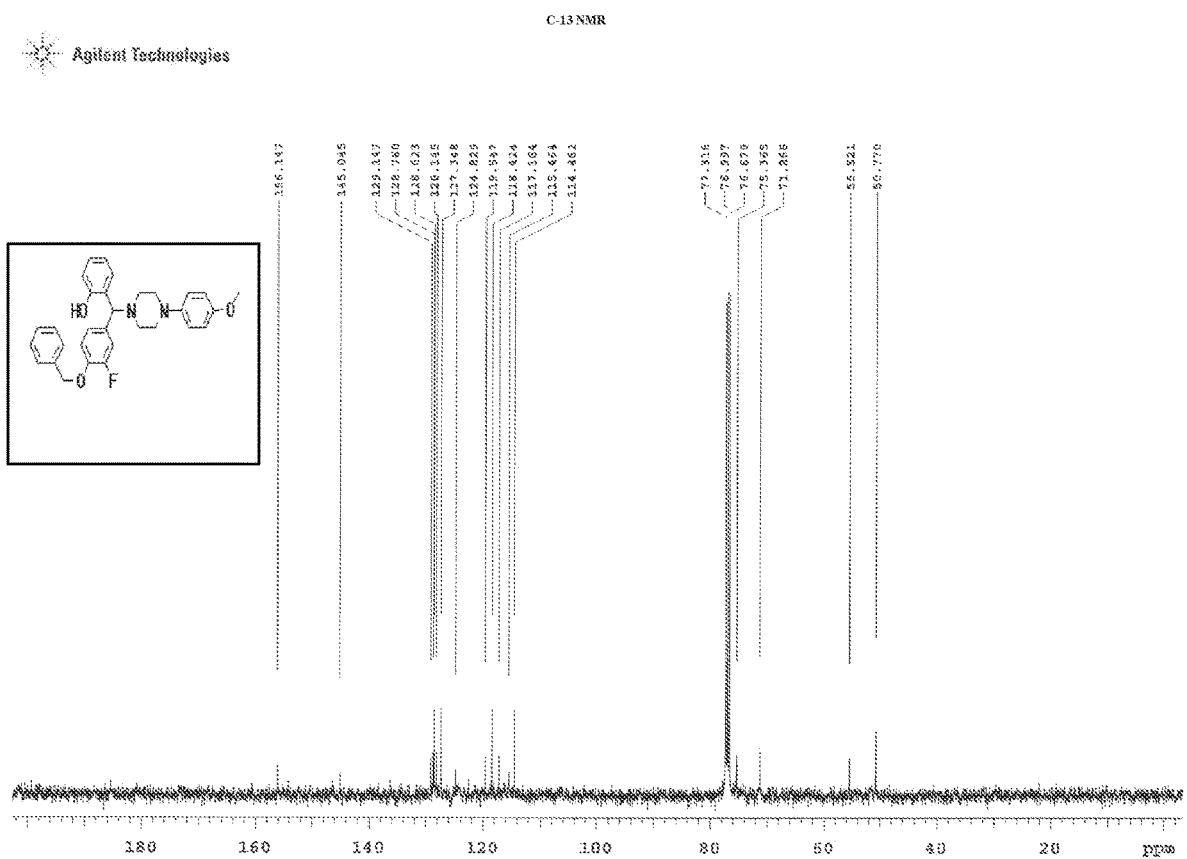

Characterization of Compound 3:

¹H NMR (CDCl₃, 400 MHz) δ: 1.194-3.079 (m, 8H), 3.689 (s, 3H), 4.336 (s, 1H), 5.041 (s, 2H), 6.672-6.702 (m, 1H), 6.781-6.819 (m, 5H), 6.863-6.867 (m, 2H), 7.026-7.082 (m, 2H), 7.196 (m, 1H), 7.279-7.348 (m, 5H); ¹³C NMR (400 MHz, CDCl3) δ: 50.770, 55.52, 71.26, 75.36, 114.46, 115.46, 117.16, 118.42, 119.54, 124.82, 127.34, 128.14, 128.62, 128.76, 129.14, 145.04, 156.14; Melting point 72-76° C. (FIG. 3)

Figure 4A:
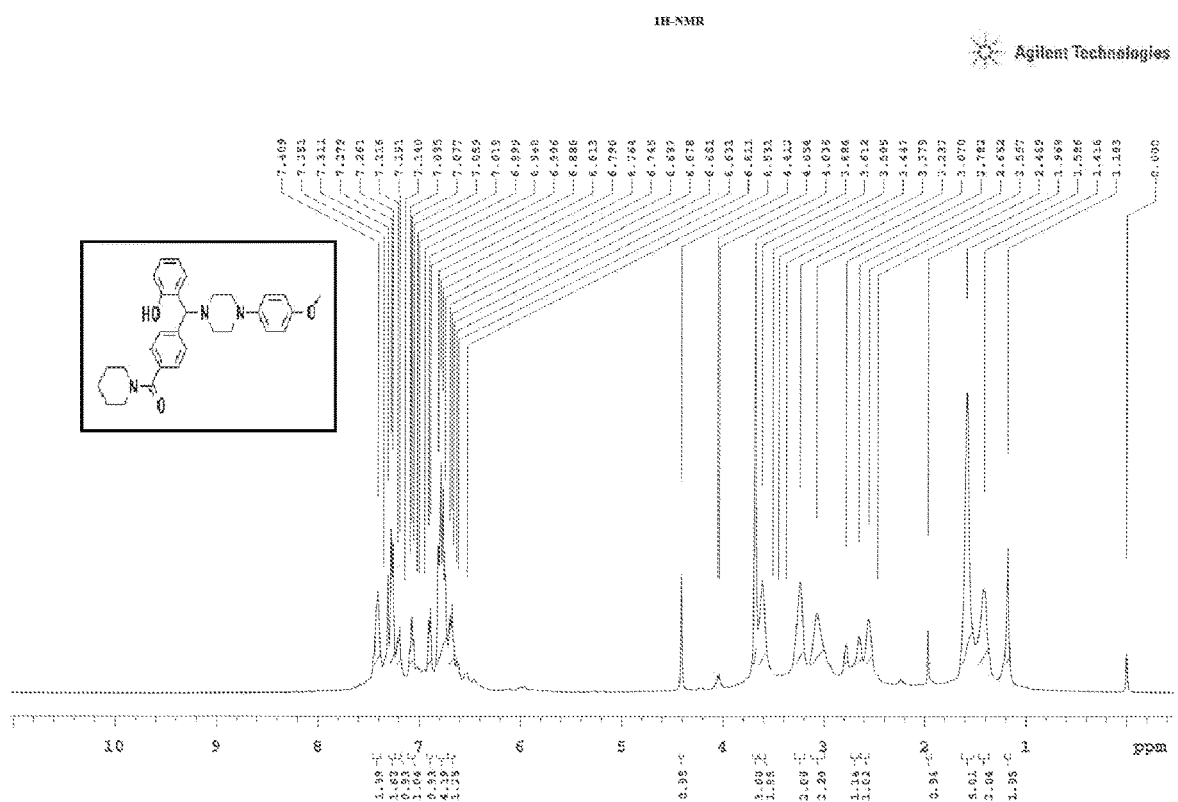
Figure 4B:
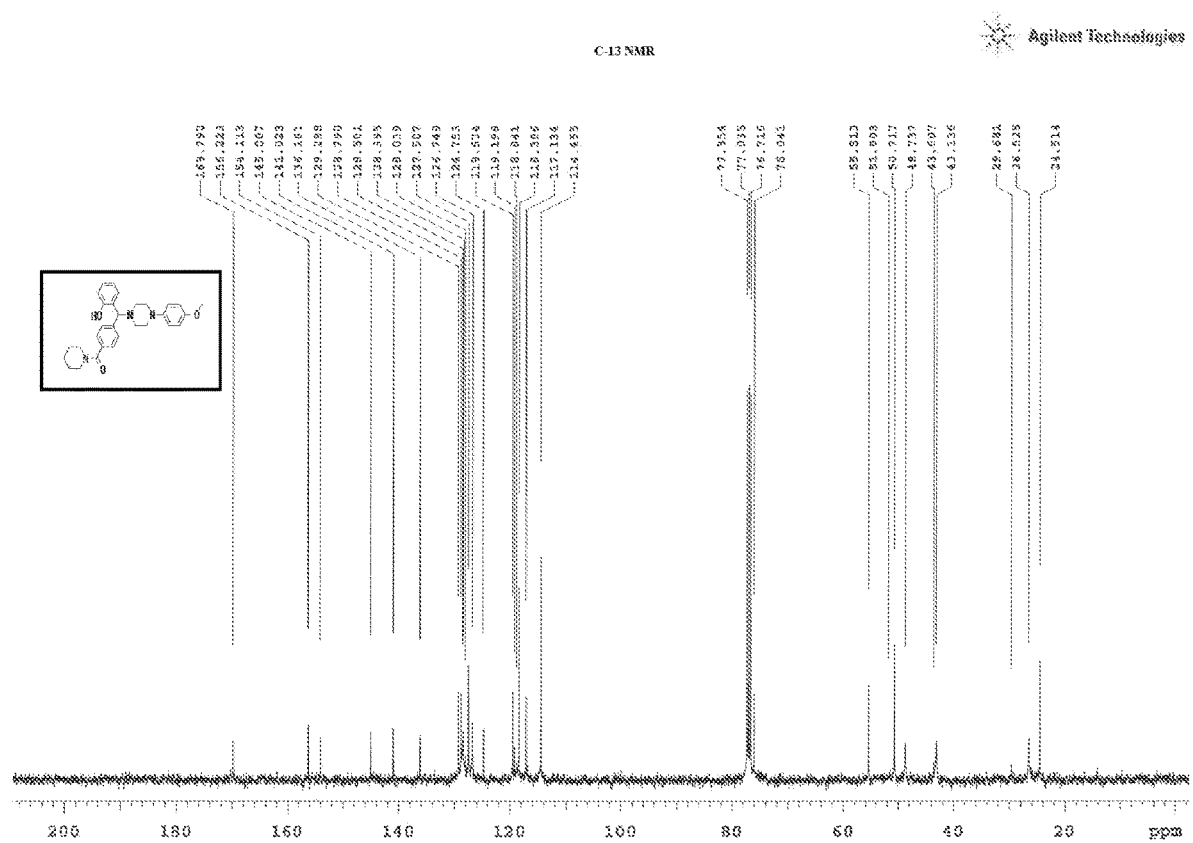

Characterization of Compound 4:

¹H NMR (CDCl₃, 400 MHz) δ: 1.183-2.469 (m, 10H), 2.557-3.684 (m, 8H), 3.684 (s, 3H), 4.412 (s, 1H), 6.631 (m, 2H), 6.745-6.813 (m, 4H), 7.059-7.095 (m, 1H), 7.191-7.216 (m, 1H), 7.261-7.269 (m, 2H), 7.351-7.409 (m, 2H); ¹³C NMR (400 MHz, CDCl3) δ: 24.51, 26.525, 29.68, 43.60, 48.73, 50.71, 51.80, 55.51, 76.04, 114.45, 117.134, 118.366, 119.198, 119.52, 124.75, 126.74, 127.50, 128.04, 128.50, 128.79, 129.29, 136.18, 141.02, 145, 154, 156.2, 169.79 (C=O); Melting point 78-82° C. (FIG. 4)

Figure 5A:
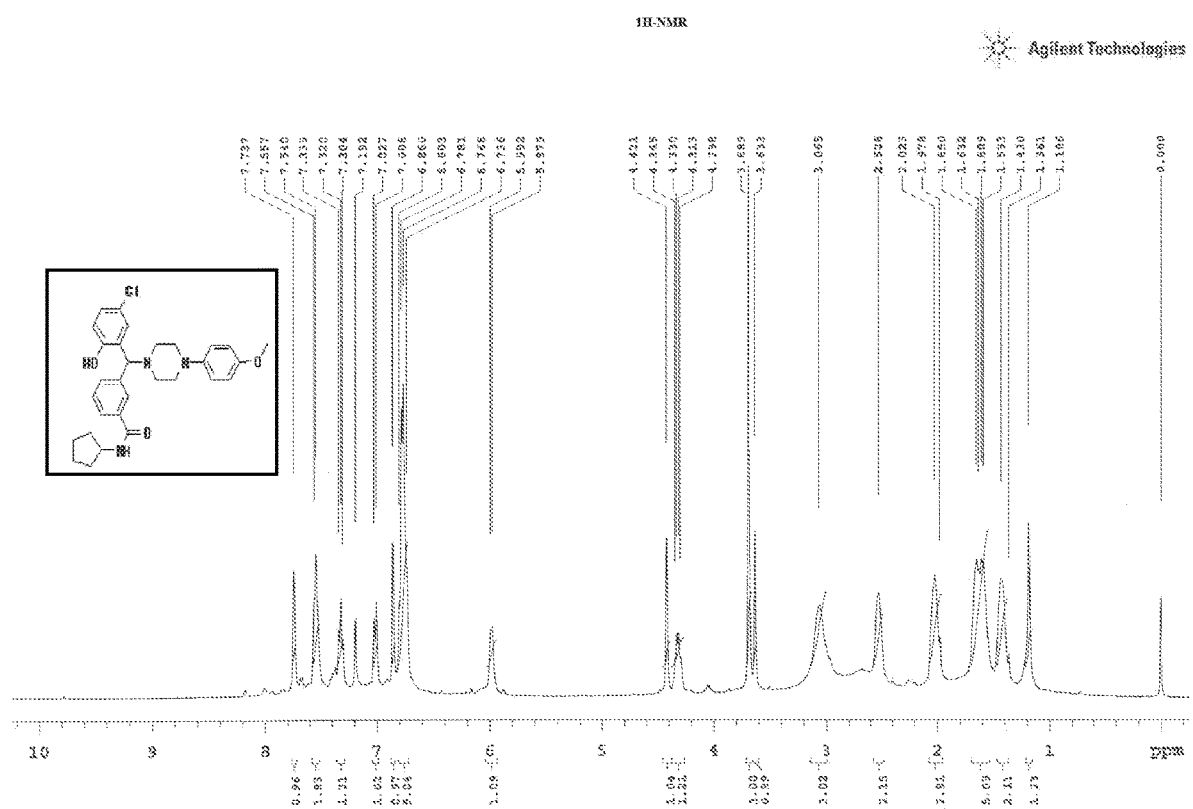
Figure 5B:
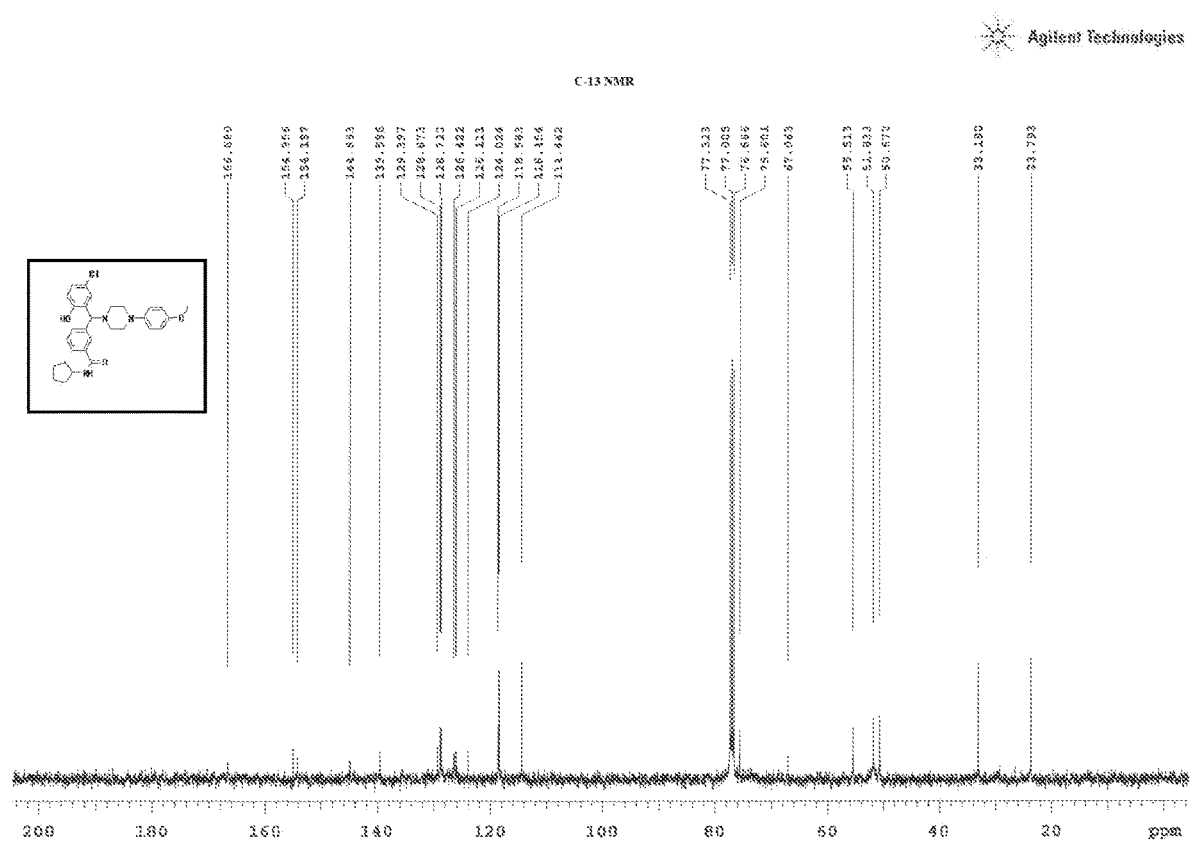

Characterization of Compound 5:

¹H NMR (CDCl₃, 400 MHz) δ: 1.186-1.650 (m, 8H), 1.978-3.633 (m, 8H), 3.689 (s, 3H), 4.298-4.345 (m, 1H), 4.421 (s, 1H), 5.979-5.992 (s, 1H) 6.736-6.803 (m, 5H), 6.860 (m, 1H), 7.192 (s, 1H), 7.737 (s, 1H), 7.304-7.339 (m, 1H), 7.540-7.557 (m, 2H); ¹³C NMR (400 MHz, CDCl3) δ: 23.79, 33.18, 50.67, 51.83, 55.51, 67.06, 75.06, 114.46, 118.45, 118.58, 124.02, 126.11, 126.42, 128.72, 128.87, 129.39, 139.39, 144.89, 154.19, 154.95, 166.68; Melting point 102-106° C. (FIG. 5)

Figure 6:
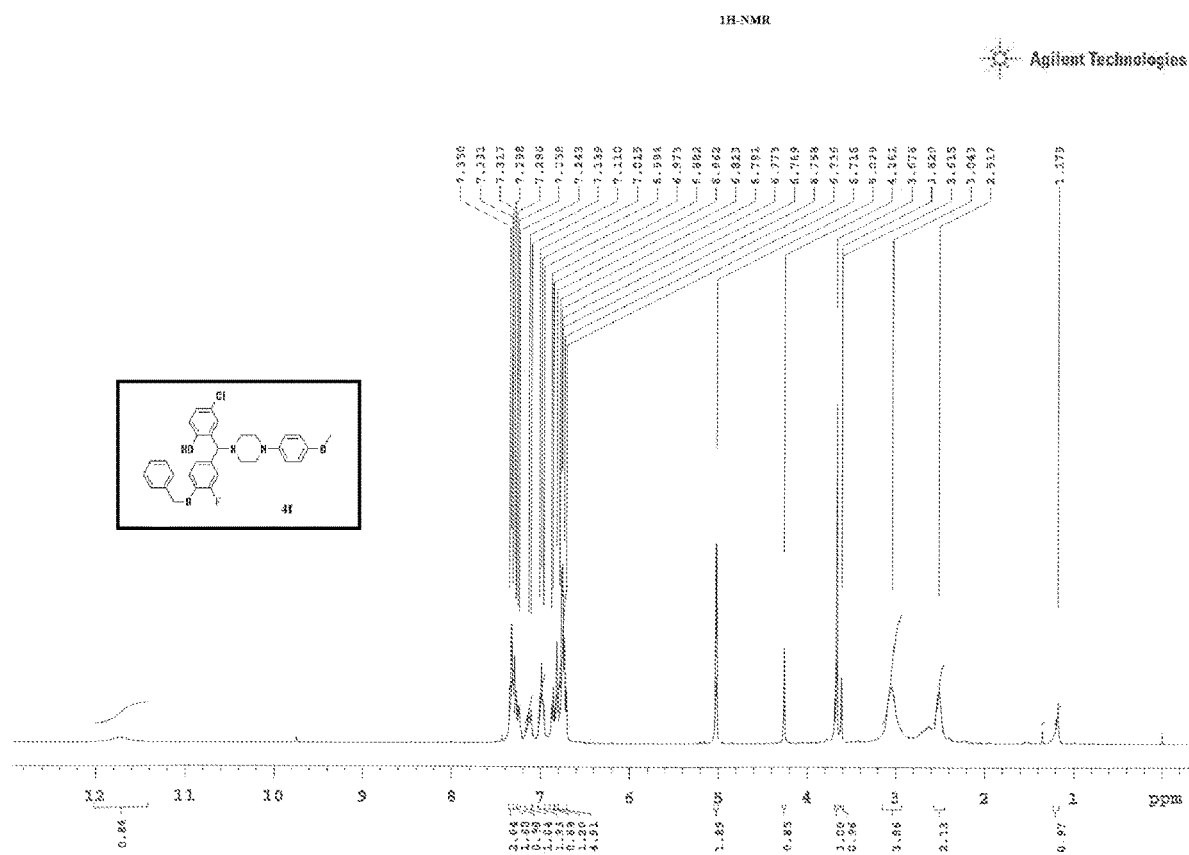

Characterization of Compound 6:

¹H NMR (CDCl₃, 400 MHz) δ: 1.179-3.620 (m, 8H), 3.676 (s, 3H), 4.261 (s, 1H), 5.029 (s, 2H), 6.716-6.791 (m, 5H), 6.823 (m, 1H), 6.862-6.882 (m, 1H), 6.973-7.015 (m, 2H), 7.110-7.139 (m, 1H), 7.243-7.258 (m, 2H), 7.280-7.317 (m, 1H), 7.331-7.350 (m, 2H); ¹³C NMR (400 MHz, CDCl3) δ: 50.70, 51.59, 55.52, 71.27, 74.93, 114.48, 115.52, 118.58, 123.97, 124.39, 126.3, 127.3, 128.2, 128.8, 132.1, 136.27, 144.96, 146.74, 154.19, 154.93; Melting point 60-64° C. (FIG. 6)

Figure 7A:
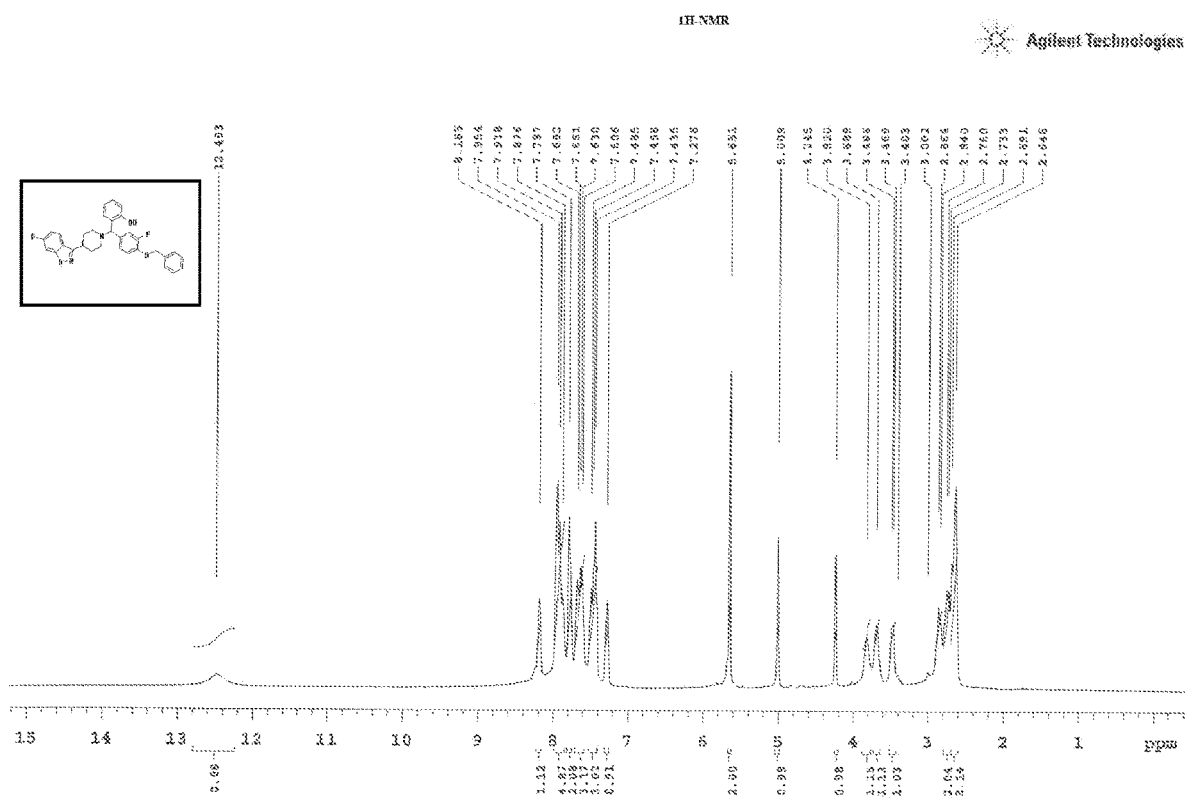
Figure 7B:
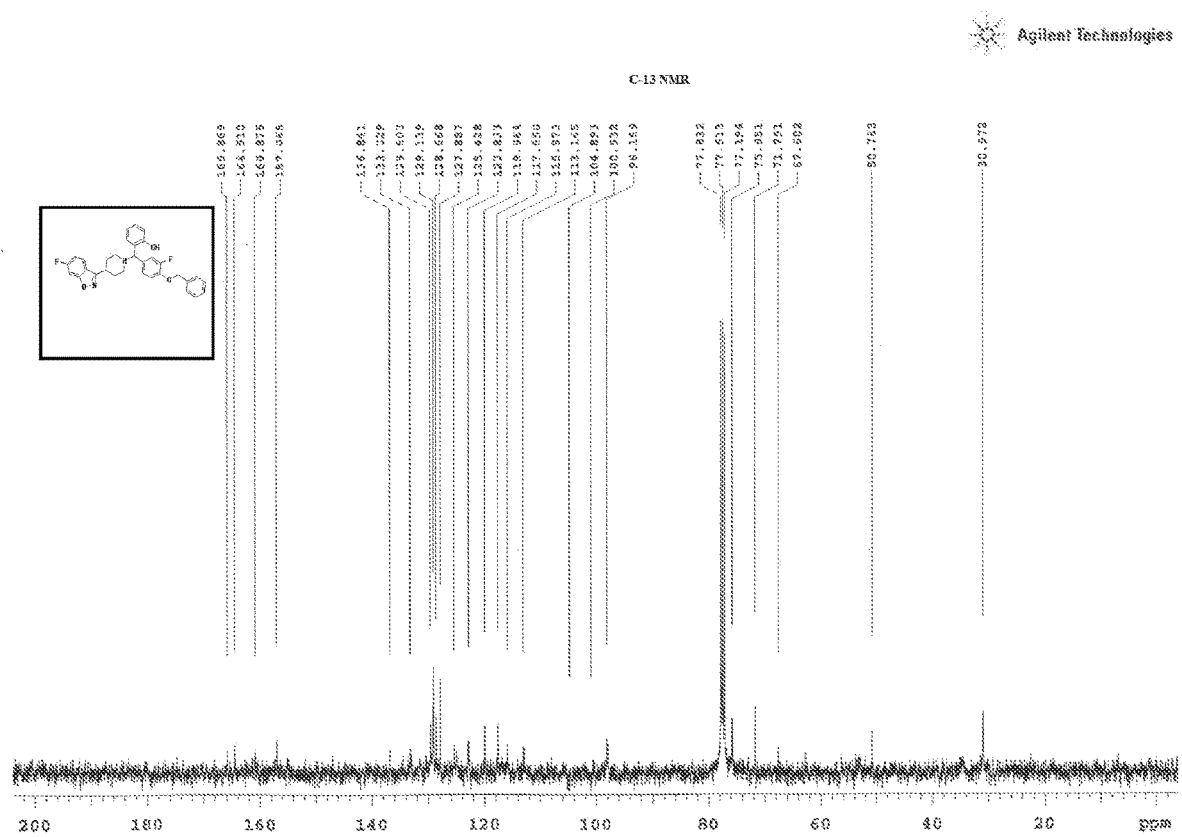

Characterization of Compound 7:

¹H NMR (CDCl₃, 400 MHz) δ: 2.648-3.820 (m, 8H) 4.245 (s, 1H), 5.009 (s, 1H), 5.651 (s, 2H), 7.276 (s, 1H), 7.436-7.485 (m, 3H), 7.606-7.682 (m, 3H), 7.797 (m, 2H), 7.876-7.954 (m, 5H), 8.185 (s, 1H); ¹³C NMR (400 MHz, CDCl3) δ: 30.972, 50.76, 67.60, 71.79, 75.85, 98.16, 100.9, 104.9, 113.16, 115.97, 117.65, 119.96, 122.84, 125.4, 127.8, 128.6, 129.1, 129.6, 133.2, 136.8, 157.06, 160.87, 164.51, 165.86; Melting point 58-62° C. (FIG. 7)

Figure 8:
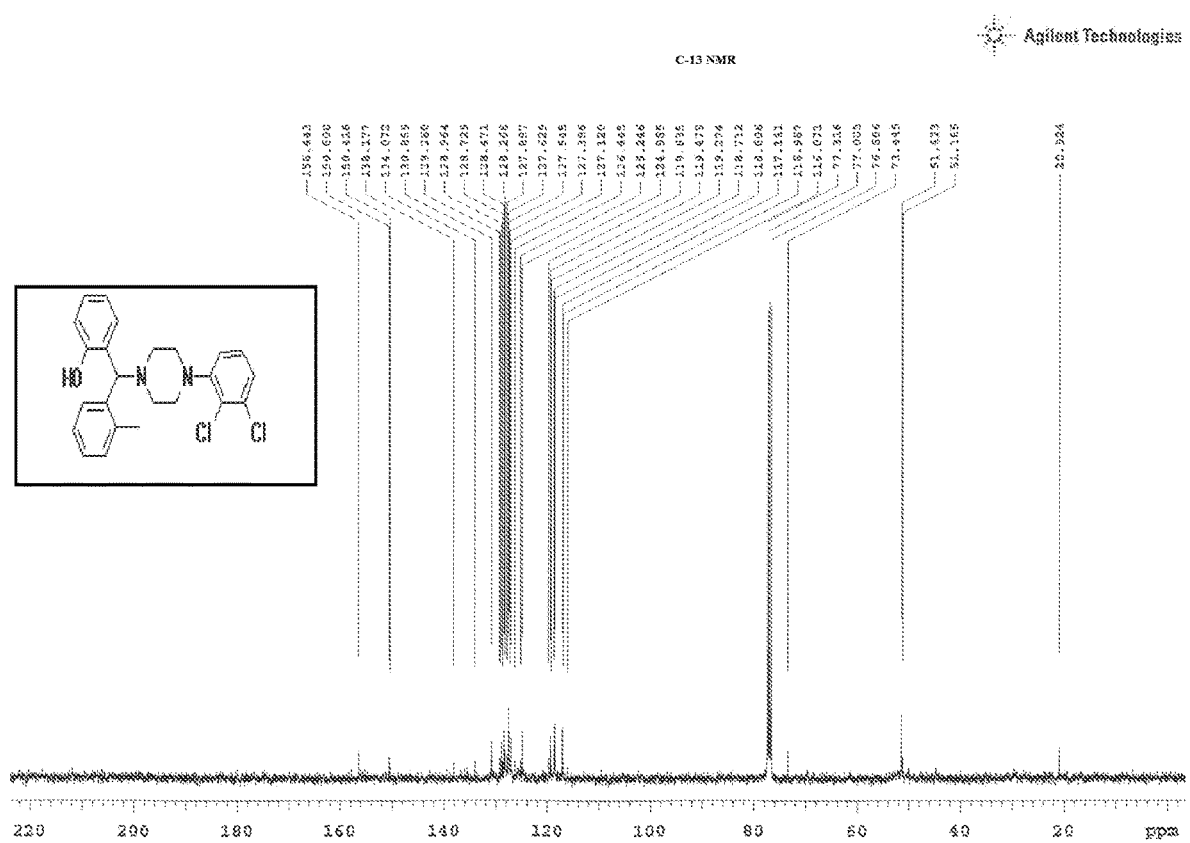

Characterization of Compound 8:

¹H NMR (CDCl₃, 400 MHz) δ: 2.479 (s, 3H), 4.927 (s, 1H), 2.260-3.063 (m, 8H), 6.533-6.551 (d, 1H, J=7.2 Hz), 6.631-6.692 (m, 2H), 6.739-6.758 (d, 1H, J=7.6 Hz), 6.789-6.809 (d, 1H, J=8 Hz), 6.864 (m, 3H), 7.092-7.183 (m, 1H), 7.281-7.297 (m, 1H), 7.537-7.552 (d, 1H, J=6 Hz); ¹³C NMR (400 MHz, CDCl3) δ: 20.92, 51.16, 51.42, 73.44, 116.07, 116.96, 117.14, 118.716, 119.27, 119.83, 124.965, 125.24, 126.445, 127.12, 127.545, 128.266, 128.729, 129.260, 130.869, 134.072, 138.171, 150.600, 156.443 Melting point 108-112° C. (FIG. 8)

Figure 9A:
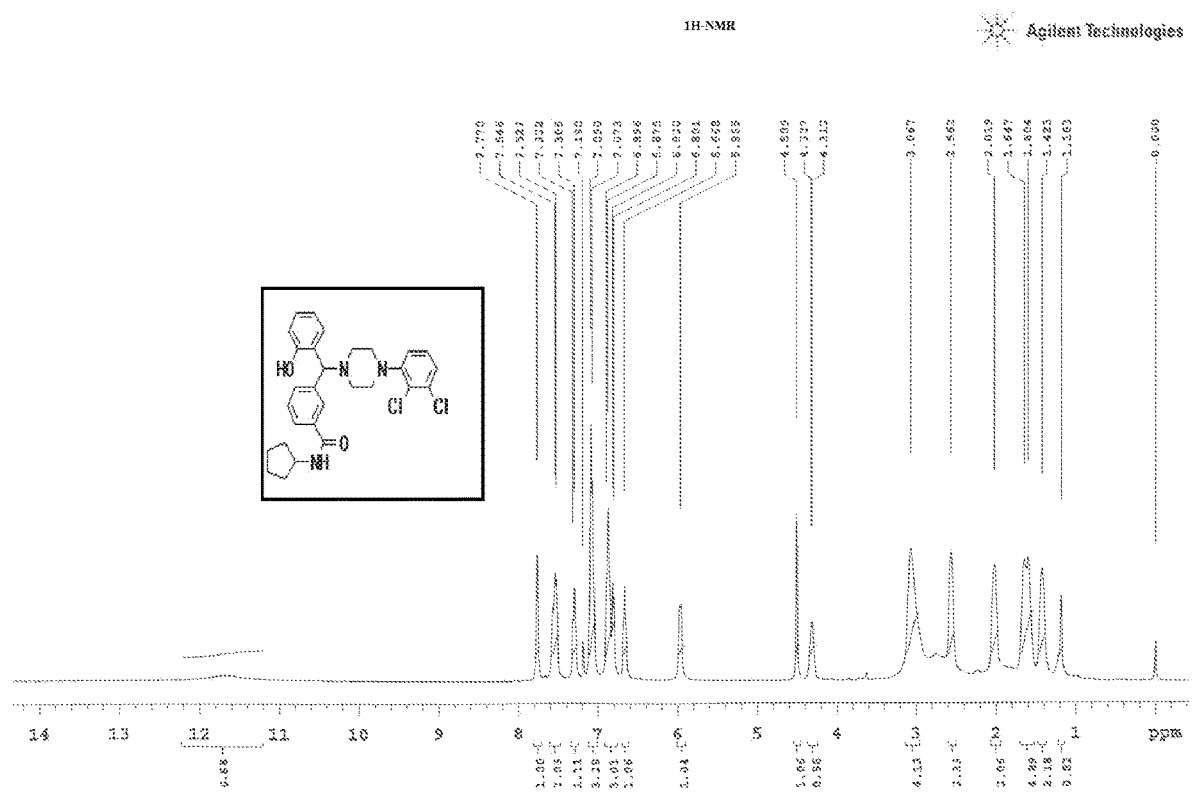
Figure 9B:
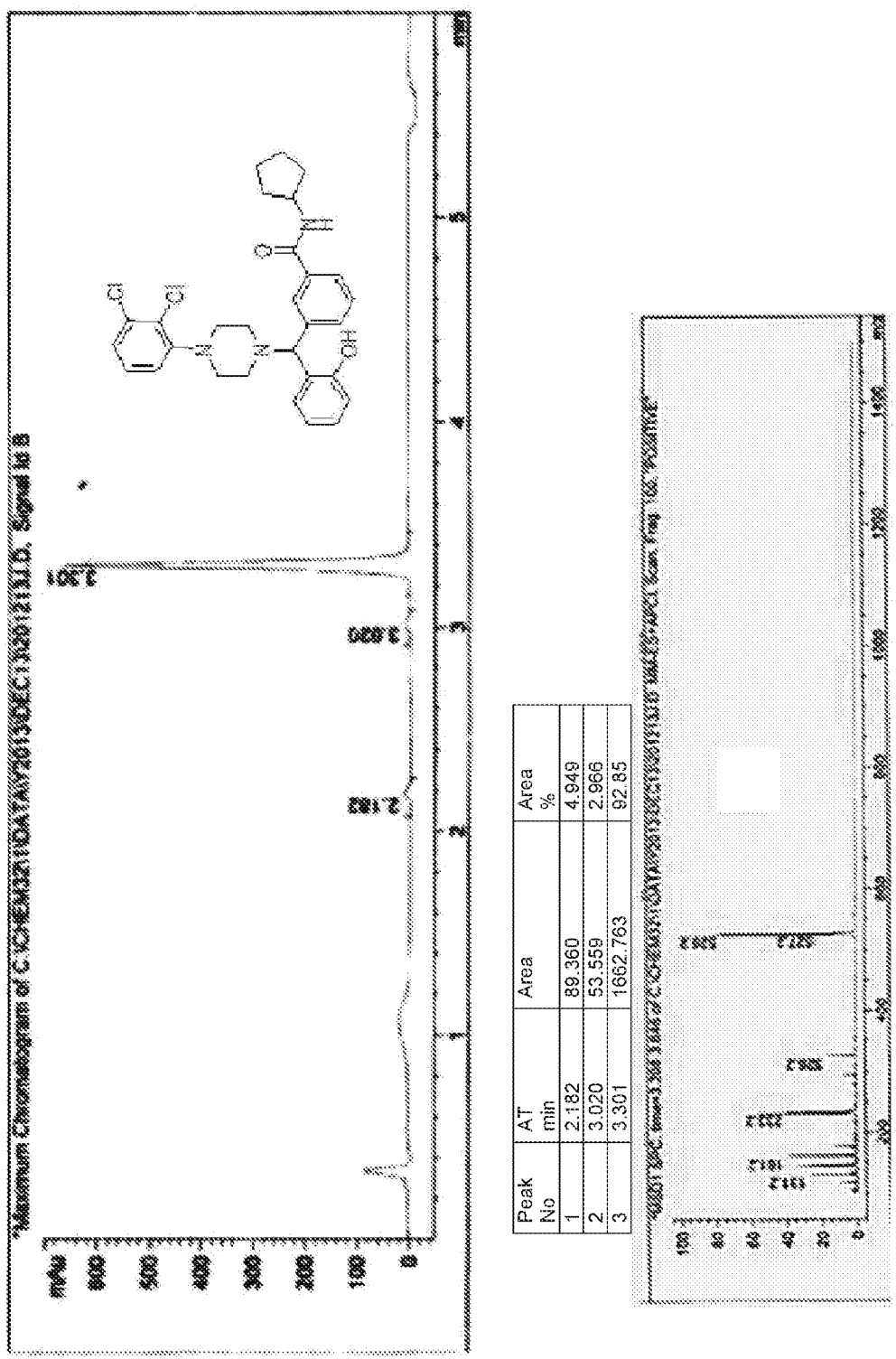

Characterization of Compound 9 (NPB):

¹H NMR (CDCl₃, 400 MHz) δ: 1.183-1.647 (m, 8H), 2.019-3.067 (m, 8H), 4.509 (s, 1H), 4.312-4.327 (m, 1H, NH), 5.965 (s, 1H), 6.668 (m, 1H), 6.801-6.896 (m, 3H), 7.073-7.190 (m, 3H), 7.305 (m, 1H), 7.527-7.542 (m, 2H), 7.770 (s, 1H); ¹³C NMR (400 MHz, CDCl3) δ: 23.78, 33.18, 51.22, 51.78, 76.10, 117.14, 118.59, 119.67, 124.69, 124.98, 126.22, 127.53, 128.85, 129.29, 131.08, 134.08, 135.53, 140.28, 150.5, 156.1, 166.73; m/z (M+2, 526.2, 527.2) Melting point 174-178° C. (FIG. 9)

Figure 10:
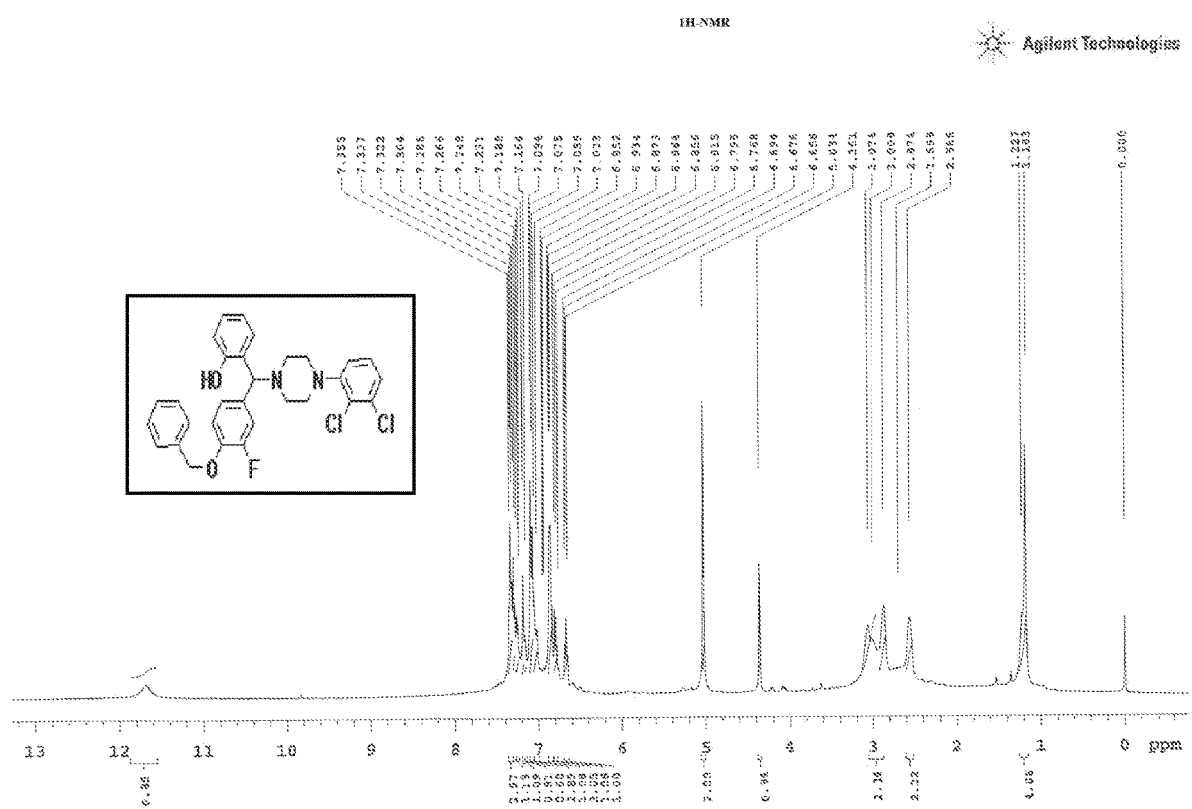

Characterization of Compound 10:

$^1$H NMR (CDCl$_3$, 400 MHz) δ: 1.183-3.074 (m, 8H), 4.361 (s, 1H), 5.034 (s, 2H), 6.658-6.694 (t, 1H, J=7.2 Hz), 6.768 (m, 1H), 6.856-6.873 (m, 3H), 7.023 (m, 1H), 7.055-7.094 (m, 3H), 7.164 (m, 1H), 7.231 (m, 1H), 7.266 (m, 1H), 7.304 (m, 1H), 7.322-7.355 (m, 2H); $^{13}$C NMR (400 MHz, CDCl3) δ: 51.264, 71.260, 75.434, 117.15, 118.6, 119.6, 124.8, 124.9, 127.3, 127.5, 128.1, 128.6, 128.8, 129.18, 150.5, 156.09; Melting point 75-80° C. (FIG. 10)

Example 2

Compound of Formula I Decreases the Cell Viability of a Range of Carcinoma Cells Oncogenicity Assay We initially investigated the effect of newly synthesized small molecule compounds against MCF7 cells (ER+ MC cells) using an AlamarBlue® cell viability assay. Among the series of novel small molecule compounds, NPB was identified as an efficacious small molecule compound reducing viability of MCF7 cells compared to vehicle (DMSO) treated cells. Among the compounds, Compound 9 N-cyclopentyl-3-((4-(2,3-dichlorophenyl)piperazin-1-yl)(2-hydroxyphenyl)methyl)benzamide (NPB) is identified as the most potent antiproliferative compound with the IC$_{50}$ of 6.5 μM. We next determined the inhibitory concentration 50% (IC$_{50}$) of NPB in wide-range of carcinoma cell lines including those derived from ER– mammary (BT549, MDA-MB-231), ER+ mammary (MCF7, T47D, and BT474), endometrial (Ishikawa, ECC-1, RL95-2, and AN3), ovarian (SK-OV-3, OVCAR-2, Caov-3, HEY C2, and OVCA433), hepatocellular (Hep3B, H2P, and H2M), colon (HCT116, DLD-1, and Caco-2), prostate (PC3, LNCaP, and DU145) and pancreatic (AsPC-1, BxPC-3) carcinoma. As normal cell controls, we also included immortalized mammary epithelial cells (MCF10A and MCF12A), and immortalized hepatocytes (LO2) in the panel of cell lines. The IC$_{50}$ values for NPB in the carcinoma cell lines are tabulated in FIG. 11.

Example 3

NPB Induces Apoptotic Cell Death in Range of Carcinoma Cell Lines

In addition, NPB is evaluated against several cancer-derived cell lines to determine effect on whole cell viability, apoptosis, and cytotoxicity using ApoTox-Glo™ Triplex Assay Kit, Promega (Singapore) according to manufacturer's instructions (FIG. 12). In brief, cells are seeded in black opaque 96-well plates (Corning®, Singapore). After an overnight incubation of cells, the medium is changed to the indicated NPB concentration. After about 48 hours of incubation, the viability/cytotoxicity reagent containing both GF-AFC substrate and bis-AAF-R110 substrate are added to the cells as suggested by the supplier. After about 45 minutes incubation at about 37° C., fluorescence is recorded at 400 nm excitation/505 nm emission for viability and 485 nm excitation/520 nm emission for cytotoxicity using a Tecan microplate reader for fluorescence (Tecan, Singapore). Caspase-Glo 3/7 Reagent is further added to the cells and after about 25 minutes of incubation at room temperature, luminescence is recorded using Tecan microplate reader. Numbers of viable, cytotoxic, and apoptotic cells are measured in triplicates.

Annexin V and Propidium Iodide (Annexin V-PI) Apoptosis Assay

Phosphatidylserine exposure and cell death are assessed by FACS analysis using Annexin-V-FLUOS Staining Kit (Life Technologies, Singapore) and PI-stained cells. Briefly, 1×10$^5$ MCF cells/well (190 μL/well) are seeded in 6-well plates and incubated with different concentrations of NPB for about 24 hours and DMSO treated samples are used as control. Cells are then washed with Annexin V binding buffer (10 mM HEPES/NaOH, pH7.4, 140 mM NaCl, 2.5 mM CaCl$_2$), stained with Annexin V FITC for about 30 minutes at room temperature in the dark, then washed again and re-suspended in Annexin V binding buffer containing PI. Samples are analyzed immediately on a BD FACSAria Cell Sorter (BD Biosciences, San Jose, Calif.).

Loss of membrane integrity and translocation of phosphatidylserine to outer leaflet of plasma membrane are the early events of apoptosis which can be detected using FITC conjugated annexin-V and propidium iodide staining. It is observed that NPB induces apoptosis in MCF7 cells using FITC-annexin V and propidium iodide. On treatment with NPB, increase in both early (PI negative, FITC-Annexin V positive) and late apoptotic cells (PI positive, FITC-Annexin V positive) is observed in a dose dependent manner as shown in FIG. 13A.

Example 4

Molecular Interaction of NPB with Recombinant BAD Protein

To provide molecular interaction of the most promising candidate, NPB binding affinity to BAD, we performed surface plasmon resonance (SPR) measurements with immobilized BAD subunit using NPB as the analyte. We know that BAD could bind to BAD subunit in vitro. Hence, we analyzed the interaction using the BIAcore system. The recombinant BAD was immobilized on CM5 sensor chip. To determine the association and dissociation curves, various concentrations of NPB were injected individually onto the surface of a sensor chip coated with BAD. The overlaid sensorgrams shown in FIG. 14 were analyzed collectively. The direct binding of BAD to NPB was demonstrated (FIG. 14A). The calculation of kinetic parameters for the interaction of NPB with BAD revealed the association rate constant of $(1.4±0.4)×10^3$ $M^{-1}S^{-1}$ and dissociation rate constant of $(5.4±0.38)×10^3$ $S^{-1}$ of binding affinity, which yielded dissociation equilibrium constants (Kd) of 37.12 μM. These kinetic parameters shows affinity support for the interaction of BAD with NPB structure.

Surface Plasmon Resonance Analysis

Molecular interactions were analyzed based on surface plasmon resonance using a BIAcore-2000 system (BIAcore AB, Uppsala, Sweden). Human recombinant BAD protein (Catalog No. MBS143012, MyBiosource, USA) was immobilized on a sensor chip as described by the manufacturer protocol. To examine the interaction of BAD with NPB, various concentrations of NPB (20 to 100 μM) in the running buffer (HBS-EP, pH 7.4, BIAcore AB) were injected onto the surface of the BAD-immobilized sensor chip with a flow rate of 15 μl/min as per the manufacturer's directions. NPB was allowed to interact with BAD subunit for 2 min for association and dissociation, respectively, after which the sensor chip was regenerated by injecting 1 M NaCl for 2 min before the next injection. Using BIA evaluation software 4.1 (BIAcore AB), the kinetic parameters were such as association and dissociation rate constants (ka and kd), dissociation equilibrium constants (Kd) using a 1:1 binding model with mass transfer. Sensograms obtained were overlaid using BIA evaluation software.

Example 5

Effect of NPB on BAD Phosphorylation is Specific for Ser99 (Human)

Phosphorylation of hBAD at residues Ser-75 (mouse BAD serine residue 112) and Ser-99 (mouse BAD serine residue 136) are crucial in regulating the activity of the BCL-2 family of anti-apoptotic proteins [15]. hBAD phosphorylation either at Ser-75 or Ser99 (or the corresponding residues in mouse bad) results in loss of the ability of hBAD to heterodimerize with BCL-xL or BCL-2 [15]. To further validate the predicted target, we first analyzed the effect of NPB on phosphorylation of hBAD at Ser99 by western blot analysis. Treatment of MCF7 cells with NPB produced a dose dependent decrease in phosphorylation of hBAD Ser99 without a significant change in total hBAD protein (FIG. 14B). The calculated $EC_{50}$ for inhibition of BAD Ser99 phosphorylation by NPB was 0.41±0.21 µM.

Figure 15:
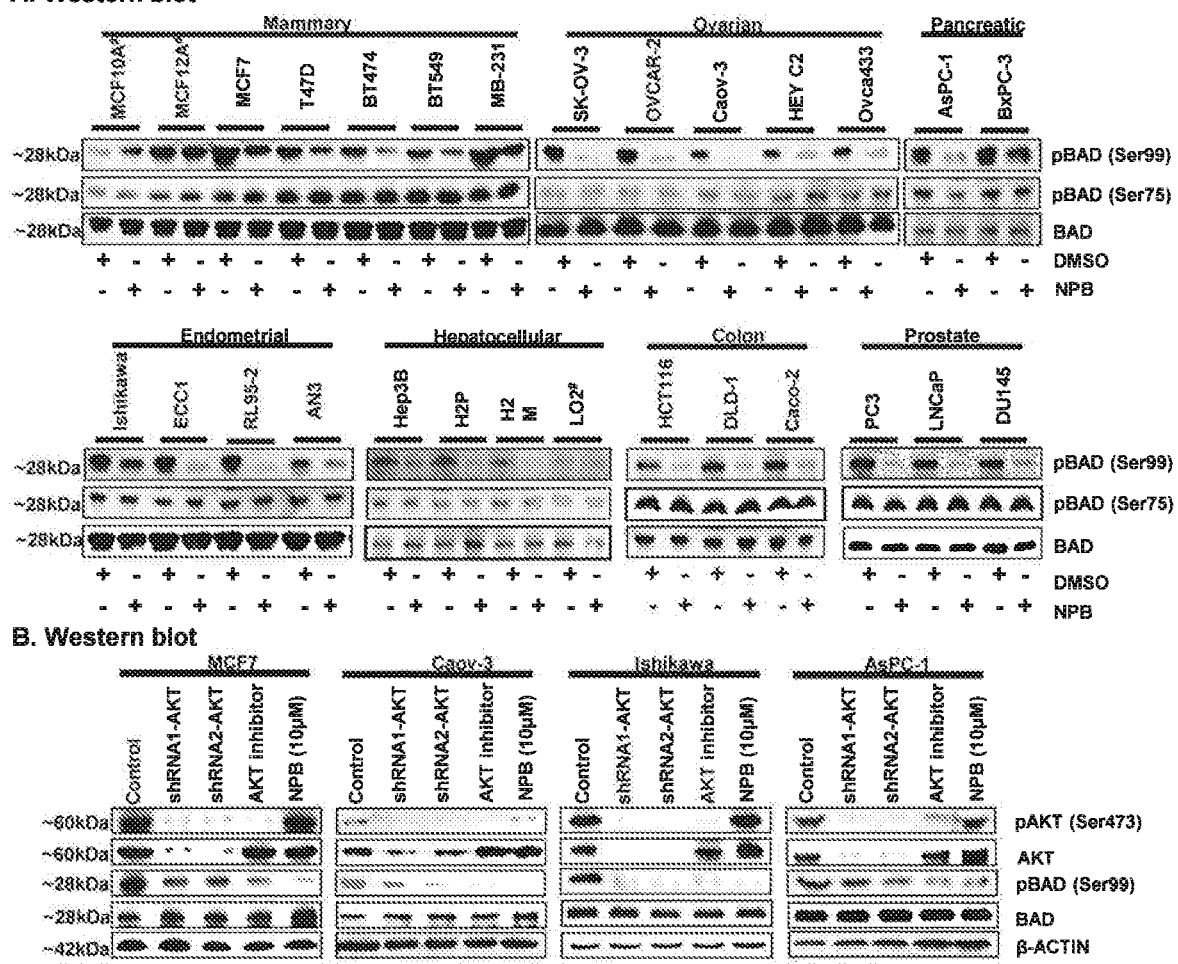

We next analyzed the effect of NPB on phosphorylation of hBAD at both Ser75 and Ser99 by western blot analysis in 25 carcinoma cell lines derived seven different types of cancer. It was observed that NPB largely inhibits the phosphorylation of BAD at the Ser99 site in all the tested carcinoma cell lines; however, NPB demonstrated no effect on the phosphorylation of hBAD at the Ser75 site in the same cells indicating that NPB specifically inhibited phosphorylation at Ser99 of hBAD (FIG. 15).

siRNA-Mediated Depletion of BAD Expression Revert Effect of NPB in Carcinoma Cell Lines.

To confirm the functional specificity of NPB directed to the BAD protein, we further examined the effect of NPB exposure after siRNA-mediated depletion of BAD expression in 6 carcinoma cell lines (MCF7, BT474, Caov-3, Ishikawa, AsPC-1 and DLD-1). Transient-transfection of the different carcinoma cells with siRNA directed to the BAD transcript decreased BAD expression and also decreased levels of phosphor-Ser99 BAD compared to their control cells (transfected with scrambled oligo) as observed by western blot analysis (FIG. 16A). Cell viability nor apoptosis were significantly altered upon siRNA mediated depletion of BAD as previously reported [26]. As described above, NPB treatment of the control transfected carcinoma cell lines decreased BAD phosphorylation (Ser99) compared to vehicle-treated cells. Concomitantly, exposure of the same carcinoma cell lines to NPB decreased cell viability and increased caspase 3/7 activity compared to vehicle-exposed cells. In contrast, NPB did not affect cell viability nor caspase3/7 activity in carcinoma cell lines with depleted expression of BAD (FIGS. 16B&C).

Example 6

NPB Inhibits BAD Phosphorylation Independent of AKT Signaling in Carcinoma Cell Lines The upstream AKT Ser/Thr kinase regulates the phosphorylation of hBAD at Ser99 [13]. We therefore determined whether NPB inhibits the phosphorylation of hBAD (Ser99) via modulation of the activity of AKT (as indicated by phosphorylation of Ser473) using western blot analysis. We observed no change in the levels of pAKT or levels of total AKT protein after exposure of four different carcinoma cells lines (MCF7, Caov-3, Ishikawa, and AsPC-1) to 10 µM NPB. However, all NPB treated carcinoma cell lines (MCF7, Caov-3, Ishikawa, and AsPC-1) exhibited inhibition of BAD phosphorylation at the Ser99 site and with no change in the level of total BAD protein (FIG. 15B). Additionally, we examined BAD phosphorylation after depletion of AKT using two independent shRNA targeting AKT expression or inhibition of AKT activity with AKT inhibitor IV as a positive control in the different carcinoma cell lines. We observed that depleted expression of AKT in the carcinoma cell lines was associated with a concomitant decrease in pAKT (Ser474) and pBAD (Ser99) levels compared to control cells; indicative that BAD Ser99 phosphorylation is AKT dependent in all tested cancer-derived cell lines and as previously published by others [13, 15, 27-29]. NPB therefore specifically inhibits BAD phosphorylation at Ser99 without affecting the activity of the upstream kinase (AKT) [29]. These results are concordant with the in silico target prediction and NPB binding to BAD observed by SPR. Hence, NPB specifically inhibits phosphorylation of BAD at Ser99 independent of the upstream (AKT) kinase.

Example 7

5- to 6-week-old BALB/c-nu female mice were subcutaneously implanted with 17β-estradiol pellets (Innovative Research of America) at 0.72 mg/pellet with a 60-day release in the scruff of the neck after three days mice were injected subcutaneously with 100 µl of cell suspension ($1 \times 10^7$ cells) in right flanks. Tumour growth was monitored by measuring the tumour size using callipers. About 12 days after implantation, mice were randomized and divided into three groups (each group, n=8), according to treatments administered 200 µl of NPB (dissolved in 5% DMSO, 50% PEG400 and 45% water pH 5.0) by intraperitoneal injection every day for seven days. The first group of mice was treated with vehicle, the second with 5 mg/kg dose of NPB, and the third with 20 mg/kg dose of NPB. Animal weight and tumour volumes were measured daily. After completion tumours were excised, photographed, weighed, and fixed or stored in liquid nitrogen for later analysis. Histological analysis was performed as previously described (30-32).

We examined the in vivo efficacy of NPB in a xenograft (MCF7) of MC. Randomly grouped mice with preformed tumours (volume ~150 cm³) were injected intraperitoneally with vehicle or NPB at 5 mg/kg or 20 mg/kg. A significant reduction in tumour volume was observed in NPB-treated mice as compared to their vehicle-treated counterparts (FIG. 17A). During this period, animal weight was not significantly different between the groups (FIG. 17A, below). However, the tumour weight of NPB-treated animals was reduced compared to vehicle-treated mice and in a dose-dependent manner (FIG. 17B). We further analysed the effect of NPB on hBAD Ser99 phosphorylation levels in tumour tissue using WB analysis (FIG. 17C). NPB treatment significantly inhibited phosphorylation of BAD (at Ser99) in a tumour compared to control specimens. No change was observed in total levels of BAD protein between NPB treated, and the control treated tumours.

Figure 17D:
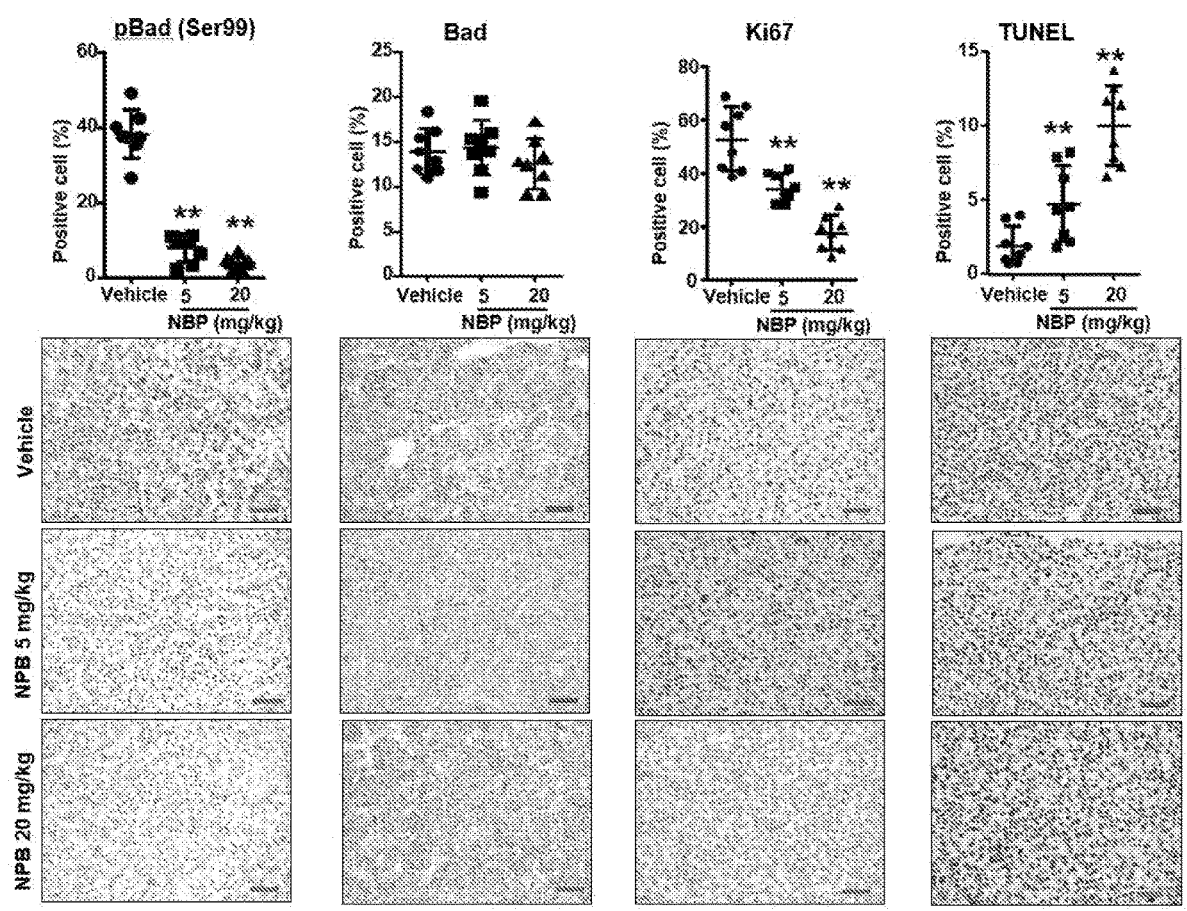

Histological analyses of tumour specimens resected from the animals treated with NPB showed significantly reduced p-BAD (Ser99) compared to vehicle-treated tumours (FIG. 17D), whereas BAD protein was not significantly different between the groups. Animals treated with NPB exhibited a significantly decreased percentage of Ki67 positive cells in tumours and a significantly increased TUNEL positivity compared to vehicle-treated (FIG. 17D).

Example 8

To elucidate the possibility that NPB decreased hBAD Ser99 phosphorylation by modulation of kinase activity, we assessed the effects of NPB on various kinases using Human Phospho-Kinase Antibody Array Kit from R&D Systems. No significant changes in kinase activity or phosphorylated substrates were observed in MCF7 cells exposed to NPB compared to DMSO exposed cells despite NPB inhibition of hBAD Ser99 phosphorylation in the same extract (FIG. 18).

Example 9

Figure 19:
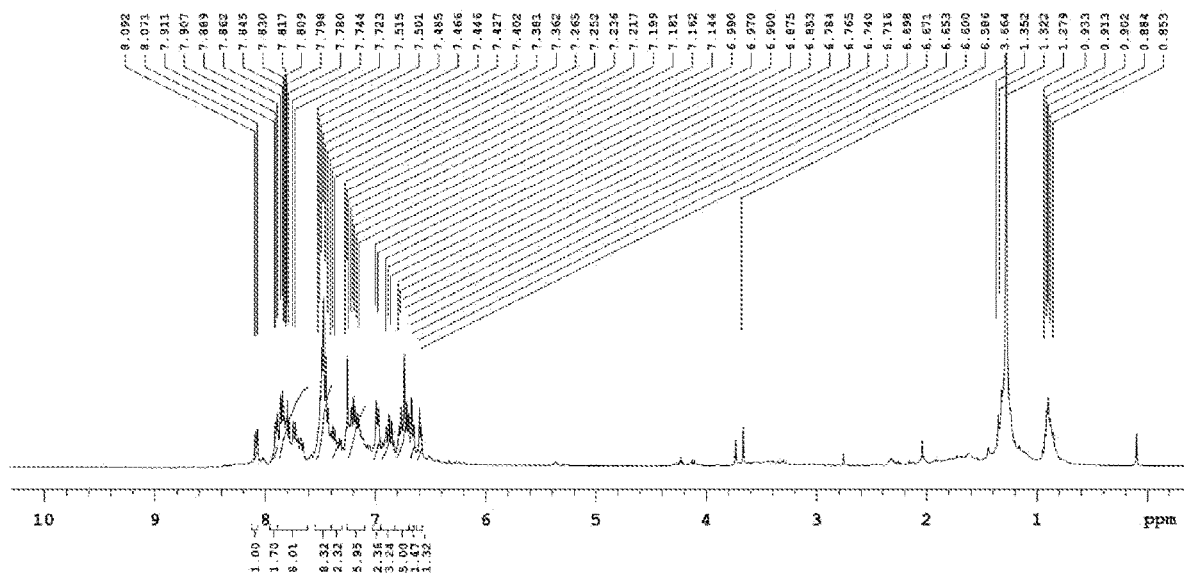
FIG. 19 depicts the $^1$H-NMR spectra of Compound NCK5.
Figure 20:
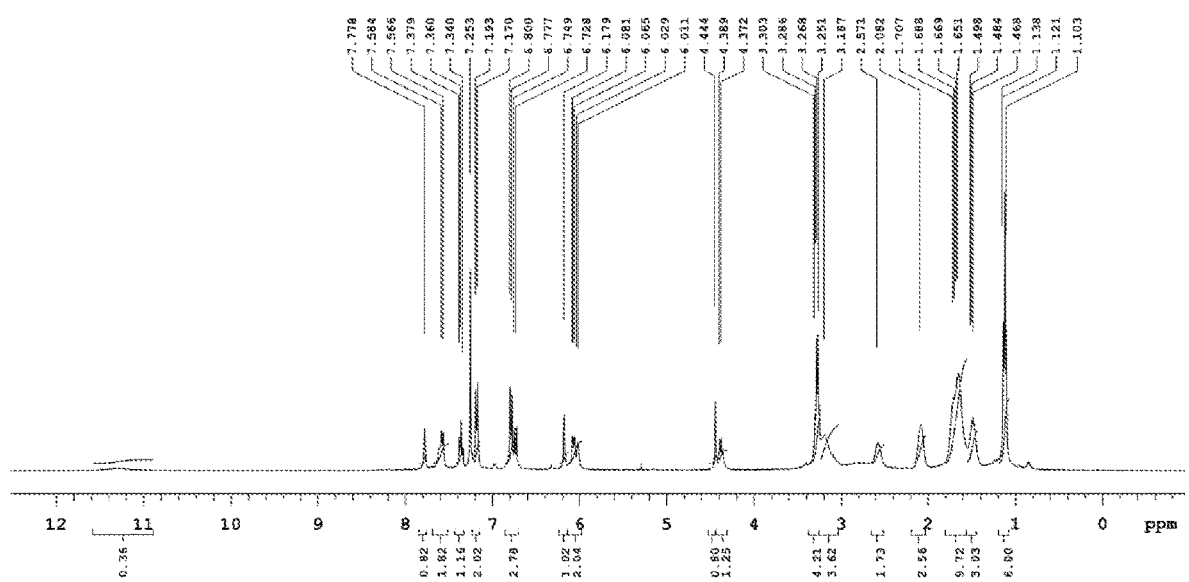
FIG. 20 depicts the $^1$H-NMR spectra of Compound NCK16.
Figure 21:
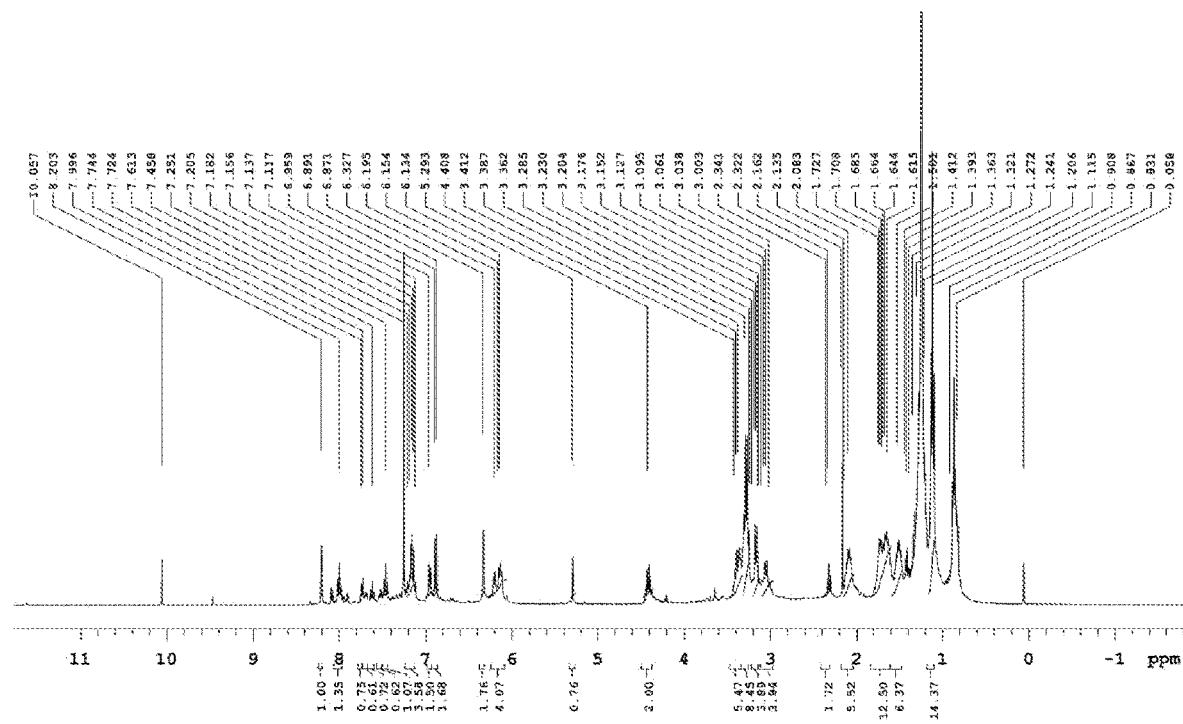
FIG. 21 depicts the $^1$H-NMR spectra of Compound NCK18.
Figure 22:
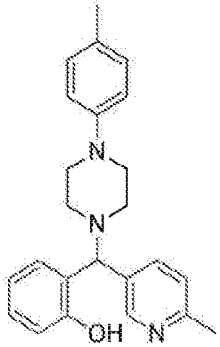

We also generated further analogues of NPB (FIGS. 19,20,21) according to the claimed chemical template and which may exhibit better pharmacokinetic profiles than NPB. Their structure and in vitro efficacy as determined by IC50 is shown in FIG. 22.

REFERENCES

1. Rakesh K S, Jagadish S, Vinayaka A C, Hemshekhar M, Paul M, Thushara R M, Sundaram M S, Swaroop T R, Mohan C D and Sadashiva M P. A New Ibuprofen Derivative Inhibits Platelet Aggregation and ROS Mediated Platelet Apoptosis. PloS one. 2014; 9(9):e107182.
2. Krautwald S, Ziegler E, Rolver L, Linkermann A, Keyser K A, Steen P, Wollert K C, Korf-Klingebiel M and Kunzendorf U. Effective blockage of both the extrinsic and intrinsic pathways of apoptosis in mice by TAT-crmA. The Journal of biological chemistry. 2010; 285(26): 19997-20005.
3. Riedl S J and Shi Y. Molecular mechanisms of caspase regulation during apoptosis. Nat Rev Mol Cell Biol. 2004; 5(11):897-907.
4. Hardwick J M and Soane L. Multiple functions of BCL-2 family proteins. Cold Spring Harbor perspectives in biology. 2013; 5(2).
5. Czabotar P E and Lessene G. Bcl-2 family proteins as therapeutic targets. Current pharmaceutical design. 2010; 16(28):3132-3148.
6. Anilkumar U and Prehn J H. Anti-apoptotic BCL-2 family proteins in acute neural injury. Frontiers in cellular neuroscience. 2014; 8:281.
7. Alberts B, Johnson A, Lewis J, Raff M, Roberts K and Walter P. Molecular Biology of the Cell. New York: Garland Science; 2008. Classic textbook now in its 5th Edition. 2010.
8. Hutt K J. The role of BH3-only proteins in apoptosis within the ovary. Reproduction (Cambridge, England). 2015; 149(2):R81-r89.
9. Ambrosini G, Adida C and Altieri D C. A novel anti-apoptosis gene, survivin, expressed in cancer and lymphoma. Nature medicine. 1997; 3(8):917-921.
10. Keerthy H K, Mohan C D, Siveen K S, Fuchs J E, Rangappa S, Sundaram M S, Li F, Girish K S, Sethi G and Bender A. Novel synthetic biscoumarins target tumor necrosis factor-α in hepatocellular carcinoma in vitro and in vivo. Journal of Biological Chemistry. 2014; 289(46): 31879-31890.
11. Smith A J, Karpova Y, D'Agostino R, Jr., Willingham M and Kulik G. Expression of the Bcl-2 protein BAD promotes prostate cancer growth. PloS one. 2009; 4(7): e6224.
12. Doerflinger M, Glab J A and Puthalakath H. BH3-only proteins: A 20-year stock-take. The FEBS journal. 2015.
13. Hayakawa J, Ohmichi M, Kurachi H, Kanda Y, Hisamoto K, Nishio Y, Adachi K, Tasaka K, Kanzaki T and Murata Y. Inhibition of BAD phosphorylation either at serine 112 via extracellular signal-regulated protein kinase cascade or at serine 136 via Akt cascade sensitizes human ovarian cancer cells to cisplatin. Cancer research. 2000; 60(21):5988-5994.
14. Macdonald A, Campbell D G, Toth R, McLauchlan H, Hastie C J and Arthur J S. Pim kinases phosphorylate multiple sites on Bad and promote 14-3-3 binding and dissociation from Bcl-X L. BMC cell biology. 2006; 7:1.
15. Fang X, Yu S, Eder A, Mao M, Bast R C, Jr., Boyd D and Mills G B. Regulation of BAD phosphorylation at serine 112 by the Ras-mitogen-activated protein kinase pathway. Oncogene. 1999; 18(48):6635-6640.
16. Masters S C, Yang H, Datta S R, Greenberg M E and Fu H. 14-3-3 inhibits Bad-induced cell death through interaction with serine-136. Molecular pharmacology. 2001; 60(6):1325-1331.
17. Harada H, Becknell B, Wilm M, Mann M, Huang L J-s, Taylor S S, Scott J D and Korsmeyer S J. Phosphorylation and inactivation of BAD by mitochondria-anchored protein kinase A. Molecular cell. 1999; 3(4):413-422.
18. Jiang P, Du W, Heese K and Wu M. The Bad guy cooperates with good cop p53: Bad is transcriptionally up-regulated by p53 and forms a Bad/p53 complex at the mitochondria to induce apoptosis. Molecular and cellular biology. 2006; 26(23):9071-9082.
19. Marchion D C, Cottrill H M, Xiong Y, Chen N, Bicaku E, Fulp W J, Bansal N, Chon H S, Stickles X B, Kamath S G, Hakam A, Li L, Su D, Moreno C, Judson P L, Berchuck A, et al. BAD phosphorylation determines ovarian cancer chemosensitivity and patient survival. Clinical cancer research: an official journal of the American Association for Cancer Research. 2011; 17(19):6356-6366.
20. Sastry K S R, Al-Muftah M A, Li P, Al-Kowari M K, Wang E, Ismail Chouchane A, Kizhakayil D, Kulik G, Marincola F M, Haoudi A and Chouchane L. Targeting proapoptotic protein BAD inhibits survival and self-renewal of cancer stem cells. Cell death and differentiation. 2014; 21(12):1936-1949.
21. Anderson M A, Huang D and Roberts A. Targeting BCL2 for the treatment of lymphoid malignancies. Seminars in hematology. 2014; 51(3):219-227.
22. Oltersdorf T, Elmore S W, Shoemaker A R, Armstrong R C, Augeri D J, Belli B A, Bruncko M, Deckwerth T L, Dinges J and Hajduk P J. An inhibitor of Bcl-2 family proteins induces regression of solid tumours. Nature. 2005; 435(7042):677-681.
23. Keerthy H K, Garg M, Mohan C D, Madan V, Kanojia D, Shobith R, Nanjundaswamy S, Mason D J, Bender A and Rangappa K S. Synthesis and characterization of novel 2-amino-chromene-nitriles that target Bcl-2 in acute myeloid leukemia cell lines. PloS one. 2014; 9(9): e107118.
24. Bruncko M, Oost T K, Belli B A, Ding H, Joseph M K, Kunzer A, Martineau D, McClellan W J, Mitten M, Ng S C, Nimmer P M, Oltersdorf T, Park C M, Petros A M, Shoemaker A R, Song X, et al. Studies leading to potent, dual inhibitors of Bcl-2 and Bcl-xL. Journal of medicinal chemistry. 2007; 50(4):641-662.
25. Petros A M, Nettesheim D G, Wang Y, Olejniczak E T, Meadows R P, Mack J, Swift K, Matayoshi E D, Zhang H, Thompson C B and Fesik S W. Rationale for Bcl-xL/Bad peptide complex formation from structure, mutagenesis, and biophysical studies. Protein science: a publication of the Protein Society. 2000; 9(12):2528-2534.
26. Boisvert-Adamo K and Aplin A E. Mutant B-RAF mediates resistance to anoikis via Bad and Bim. Oncogene. 2008; 27(23):3301-3312.

27. Seow H F, Yip W K, Loh H W, Ithnin H, Por P and Rohaizak M. Immunohistochemical detection of phospho-Akt, phospho-BAD, HER2 and oestrogen receptors alpha and beta in Malaysian breast cancer patients. Pathology oncology research: POR. 2010; 16(2):239-248.
28. Kanamori Y, Kigawa J, Itamochi H, Shimada M, Takahashi M, Kamazawa S, Sato S, Akeshima R and Terakawa N. Correlation between loss of PTEN expression and Akt phosphorylation in endometrial carcinoma. Clinical cancer research: an official journal of the American Association for Cancer Research. 2001; 7(4):892-895.
29. Datta S R, Brunet A and Greenberg M E. Cellular survival: a play in three Akts. Genes & development. 1999; 13(22):2905-2927.
30. Pandey V, Wu Z S, Zhang M, Li R, Zhang J, Zhu T, et al. Trefoil factor 3 promotes metastatic seeding and predicts poor survival outcome of patients with mammary carcinoma. Breast Cancer Res. 2014; 16(5):429.
31. Wang X N, Wang S J, Pandey V, Chen P, Li Q, Wu Z S, et al. Trefoil factor 3 as a novel biomarker to distinguish between adenocarcinoma and squamous cell carcinoma. Medicine (Baltimore). 2015; 94(20):e860.
32. You M, Chen Y, Chong Q, Wu M, Pandey V, Chen R, et al. Trefoil factor 3 mediation of oncogenicity and chemoresistance in hepatocellular carcinoma is AKT-BCL-2 dependent. Oncotarget. 2017.

The invention claimed is:

1. A compound of general formula (IB):

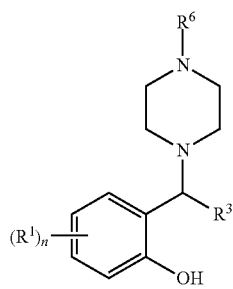

(IB)

wherein:
each $R^1$ is independently halo, $NR^{10}R^{11}$, $C_{1-6}$ alkyl, $C_{1-6}$ haloalkyl, $-O(C_{1-6}$ alkyl), $-O(C_{1-6}$ haloalkyl), aryl, heteroaryl, $-O$-aryl or $-O$-heteroaryl,
wherein
each $R^{10}$ and $R^{11}$ is independently selected from H or $C_{1-6}$ alkyl;
aryl or heteroaryl groups $R^1$ are optionally substituted with one or more substituents selected from halo, OH, cyano, nitro, $-NR^4R^5$, $-S(O)_pNR^4R^5$, $-C(O)NR^4R^5$, $-C_{1-6}$ alkyl, or $-O(C_{1-6}$ alkyl), wherein either of the $-C_{1-6}$ alkyl, or $-O(C_{1-6}$ alkyl) groups are optionally substituted with one or more substituents selected from OH, halo, arylO($C_{1-6}$ alkyl), or $O(C_{1-6}$ haloalkyl);
p is 1 or 2;
each $R^4$ and $R^5$ is independently selected from H or $C_{1-4}$ alkyl or $R^4$ and $R^5$ together with a nitrogen atom to which they are attached may form a 3-8-membered heterocyclic ring, optionally containing one or more additional heteroatoms selected from O, N and S;

n is 0, 1, 2, 3, or 4;
$R^6$ is selected from aryl substituted with one or more substituents selected from halo, $C_{1-4}$ alkyl, $C_{1-4}$ haloalkyl, $-O(C_{1-4}$ alkyl) and $-O(C_{1-4}$ haloalkyl); heteroaryl selected from indolyl, isoindolyl, benzoxazolyl and benzisoxazolyl and optionally substituted with one or more substituents selected from halo, $C_{1-4}$ alkyl, $C_{1-4}$ haloalkyl, $-O(C_{1-4}$ alkyl) and $-O(C_{1-4}$ haloalkyl); $-O$-aryl substituted with one or more substituents selected from halo, $C_{1-4}$ alkyl, $C_{1-4}$ haloalkyl, $-O(C_{1-4}$ alkyl) and $-O(C_{1-4}$ haloalkyl); $-O$-heteroaryl selected from indolyl, isoindolyl, benzoxazolyl and benzisoxazolyl and optionally substituted with one or more substituents selected from halo, $C_{1-4}$ alkyl, $C_{1-4}$ haloalkyl, $-O(C_{1-4}$ alkyl) and $-O(C_{1-4}$ haloalkyl); and $C_{1-4}$ alkyl substituted with two aryl or two heteroaryl groups, wherein at least one of the aryl and heteroaryl groups is substituted with one or more substituents selected from halo, $C_{1-4}$ alkyl, $C_{1-4}$ haloalkyl, $-O(C_{1-4}$ alkyl) and $-O(C_{1-4}$ haloalkyl);
$R^3$ is aryl or heteroaryl any of which is optionally substituted with one or more substituents $R^7$ selected from halo, $-C_{1-4}$ alkyl optionally substituted with aryl, $-O(C_{1-4}$ alkyl) optionally substituted with aryl, $-C_{1-4}$ haloalkyl, $-C(C_{1-4}$ haloalkyl) or $-C(O)NR^8R^9$;
each $R^8$ and $R^9$ is independently selected from H, $C_{1-4}$ alkyl or $C_{3-6}$ cycloalkyl or $R^8$ and $R^9$ together with the nitrogen atom to which they are attached may form a 5- or 6-membered heterocyclic ring, optionally containing one or more additional heteroatoms selected from O, N and S;
or a pharmaceutically acceptable salt, solvate or hydrate thereof or a deuterated or tritiated variant thereof, including all stereoisomers.

2. A compound according to claim 1, wherein $R^3$ is phenyl optionally substituted with one or more substituents $R^7$ such that the compound of general formula (IB) is a compound of general formula (ID):

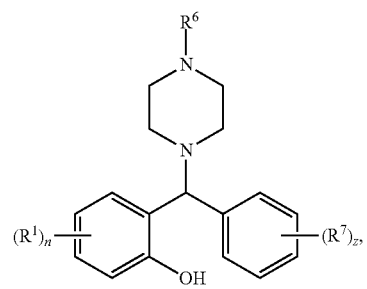

(ID)

wherein z is 0 to 5 or a pharmaceutically acceptable salt, solvate or hydrate thereof or a deuterated or tritiated variant thereof, including all stereoisomers.

3. A compound according to claim 1, wherein n is 0.

4. A compound according to claim 1, wherein n is other than 0 and $R^1$ is halo or an aryl or heteroaryl group optionally substituted as defined in claim 1.

5. A compound according to claim 4, wherein $R^1$ is an aryl or heteroaryl group optionally substituted with halo, OH, cyano, nitro, —$SO_2NH_2$, —$C(O)NR^4R^5$, —$C_{1-4}$ alkyl optionally substituted with aryl, —$C_{1-4}$ haloalkyl, —$O(C_{1-4}$ alkyl) optionally substituted with aryl or —$O(C_{1-4}$ haloalkyl), where $R^4$ and $R^5$ together with the nitrogen atom to which they are attached form a piperidine or pyrrolidine ring.

6. A compound according to claim 5, wherein $R^1$ is an aryl or heteroaryl group optionally substituted with chloro, fluoro, methyl, ethyl, trifluoromethyl, benzyl, methoxy, ethoxy, benzyloxy, trifluoromethoxy or piperidine-1-carbonyl.

7. A compound according to claim 1, wherein $R^3$ is heteroaryl optionally substituted with one or more substituents $R^7$ selected from halo, —$C_{1-4}$ alkyl optionally substituted with aryl, —$O(C_{1-4}$ alkyl) optionally substituted with aryl, —$C_{1-4}$ haloalkyl, —$O(C_{1-4}$ haloalkyl) or —$C(O)NR^8R^9$, wherein each $R^8$ and $R^9$ is independently selected from H, $C_{1-4}$ alkyl or $C_{3-6}$ cycloalkyl or $R^8$ and $R^9$ together with the nitrogen atom to which they are attached may form a 5- or 6-membered heterocyclic ring, optionally containing one or more additional heteroatoms selected from O, N and S.

8. A compound according to claim 1 wherein each $R^1$ is independently halo, $C_{1-6}$ alkyl, $C_{1-6}$ haloalkyl, aryl or heteroaryl, wherein aryl or heteroaryl groups are optionally substituted with one or more substituents selected from halo, OH, cyano, nitro, —$S(O)_pNR^4R^5$, —$C(O)NR^4R^5$, —$C_{1-6}$ alkyl optionally substituted with aryl, —$C_{1-6}$ haloalkyl, —$O(C_{1-6}$ alkyl) optionally substituted with aryl or —$O(C_{1-6}$ haloalkyl);

p is 0, 1 or 2;

each $R^4$ and $R^5$ is independently selected from H or $C_{1-4}$ alkyl or $R^4$ and $R^5$ together with the nitrogen atom to which they are attached may form a 5- or 6-membered heterocyclic ring, optionally containing one or more additional heteroatoms selected from O, N and S.

9. A compound according to claim 1, wherein $R^6$ is phenyl, —O-phenyl, —CH(phenyl)$_2$, or —CH(heteroaryl)$_2$, where the heteroaryl group is selected from pyridinyl, indolyl, isoindolyl, benzoxazolyl and benzisoxazolyl, and wherein any of the above $R^6$ groups may be substituted as defined in claim 1.

10. A compound according to claim 1, wherein $R^6$ is

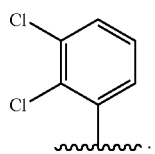

11. A compound according to claim 2, wherein z is 0, 1 or 2; $R^7$ is absent or $R^7$ is halo, —$C_{1-4}$ alkyl, benzyl, —$O(C_{1-4}$ alkyl), benzyloxy, —$C_{1-4}$ haloalkyl, —$O_{1-4}$ haloalkyl) or —$C(O)NR^8R^9$, where $R^8$ and $R^9$ together with the nitrogen atom to which they are attached form a piperidinyl ring or wherein $R^8$ is H and $R^9$ is $C_{3-6}$ cycloalkyl.

12. A compound according to claim 2, wherein z is 1, $R^7$ is $C(O)NR^8R^9$, $R^8$ is H, and $R^9$ is $C_{3-6}$ cycloalkyl.

13. A compound of claim 12 selected from the group consisting of:

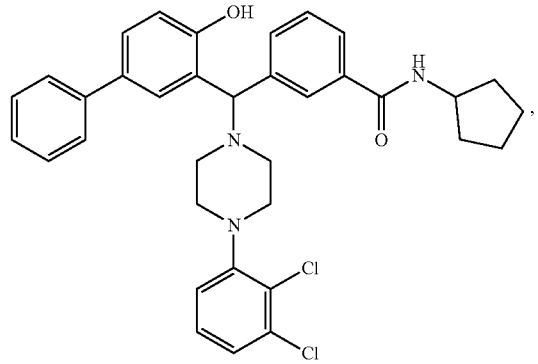

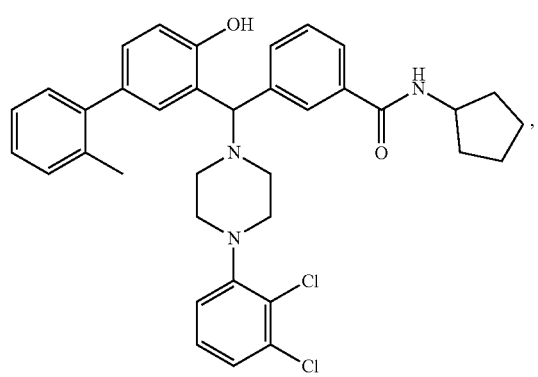

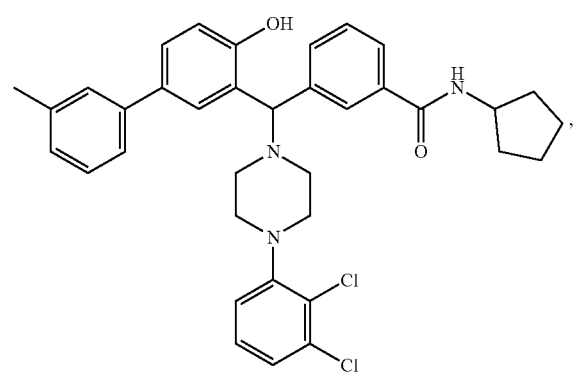

59
-continued
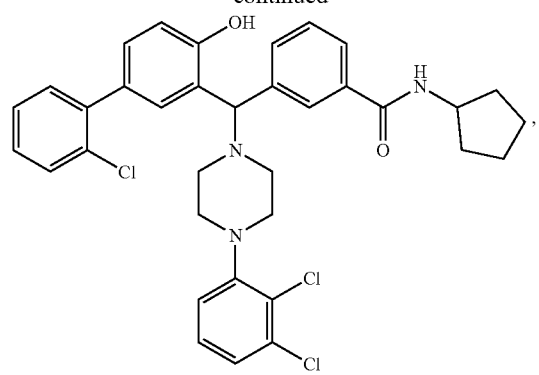
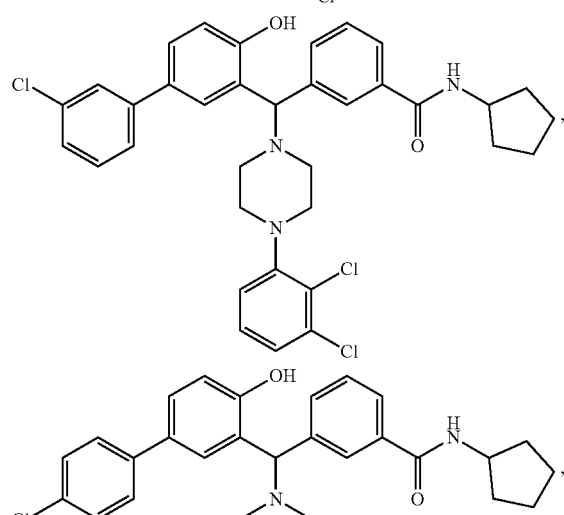
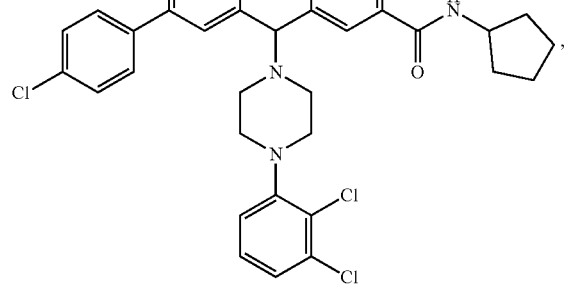
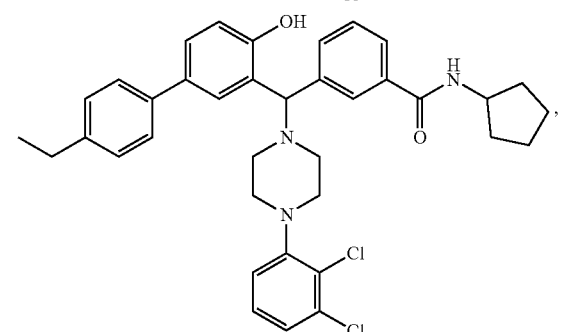
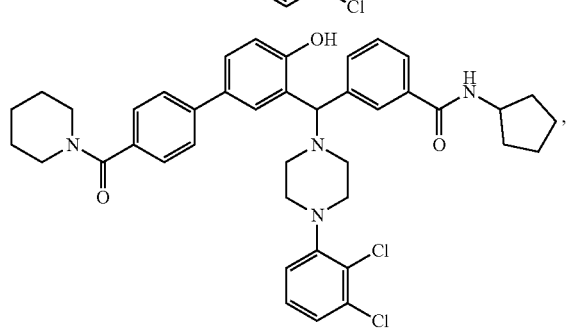
60
-continued
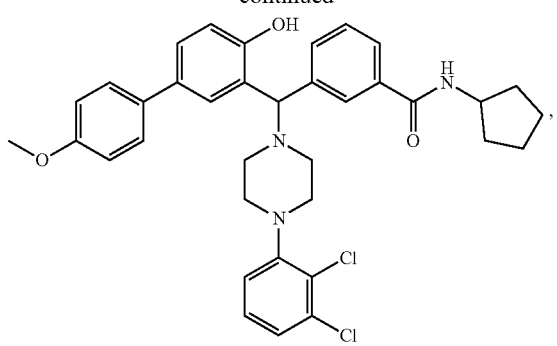
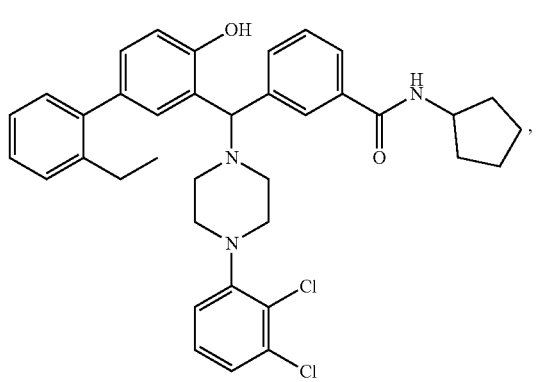
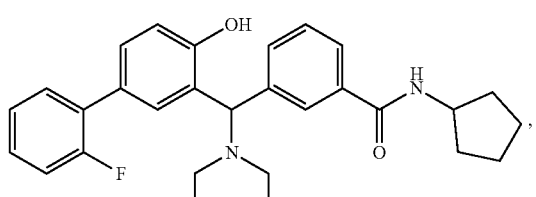
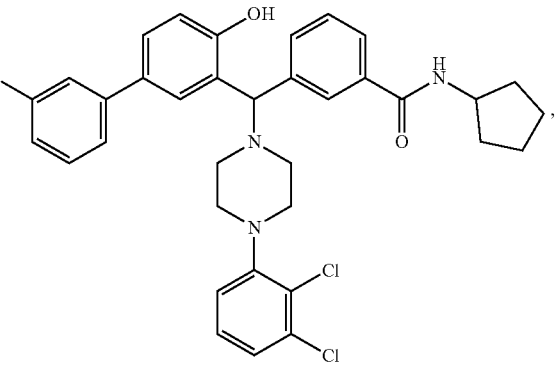

61
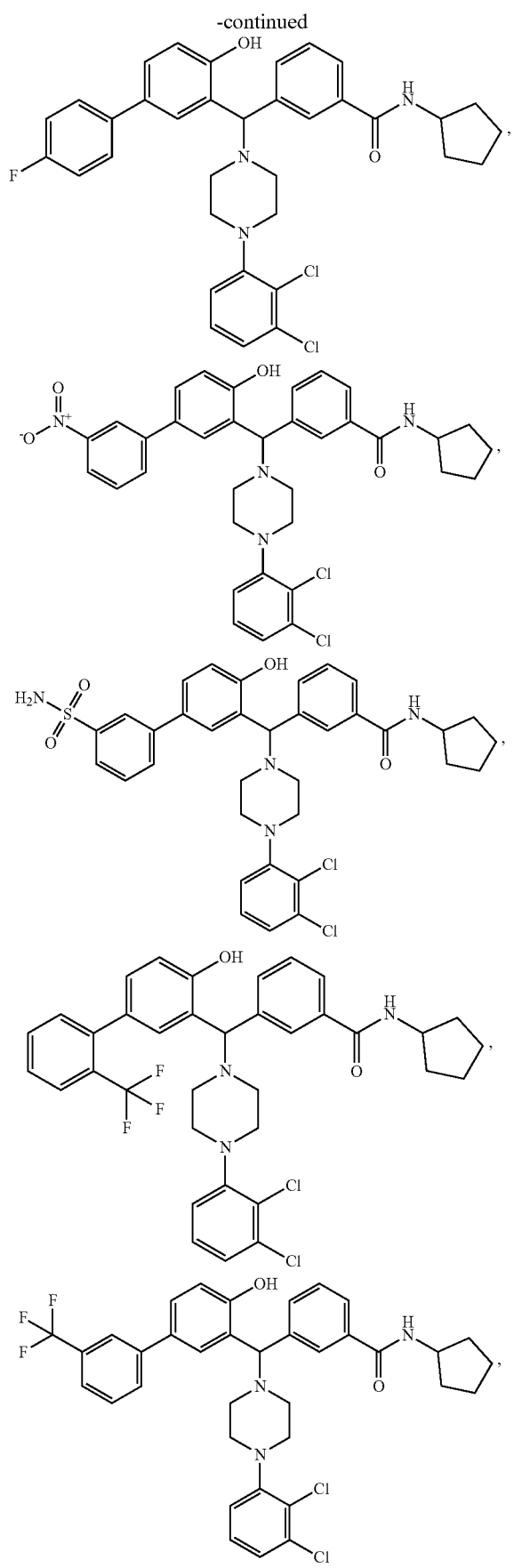
62
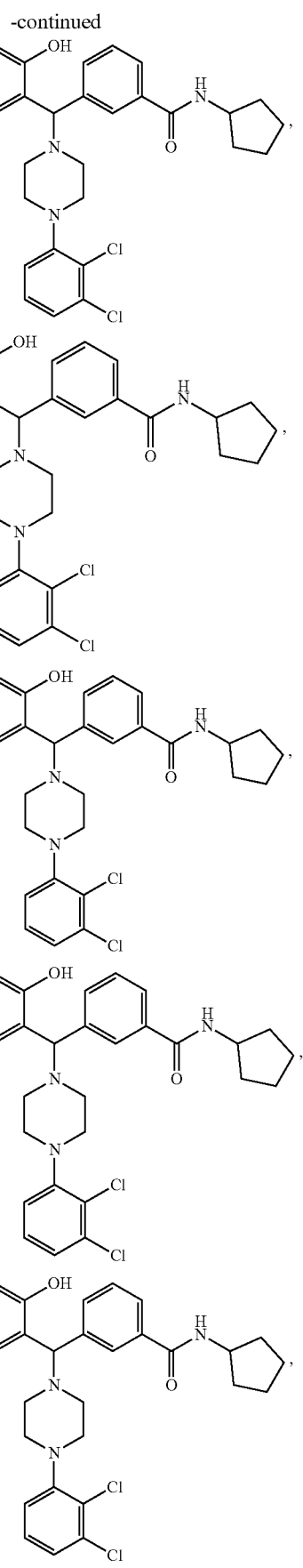

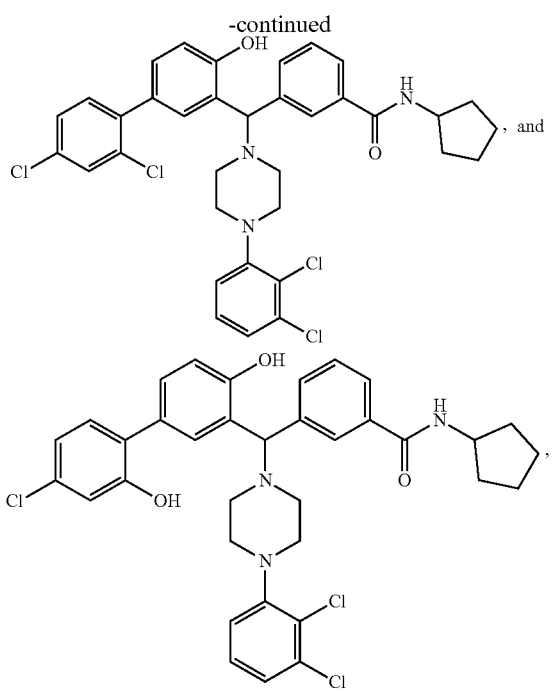

or a pharmaceutically acceptable salt, solvate or hydrate thereof or a deuterated or tritiated variant thereof, including all stereoisomers.

14. A compound selected from:
2-((2-chlorophenyl)(4-(4-methoxyphenyl)piperazin-1-yl)methyl)phenol (Compound 1);
2-((4-chlorophenyl)(4-(4-methoxyphenyl)piperazin-1-yl)methyl)phenol (Compound 2);
2-((4-(benzyloxy)-3-fluorophenyl)(4-(4-methoxyphenyl)piperazin-1-yl)methyl)phenol (Compound 3);
(4-((2-hydroxyphenyl)(4-(4-Methoxyphenyl)piperazinyl)methyl)phenyl)(piperidin-1-yl)methanone (Compound 4);
3-((5-chloro-2-hydroxyphenyl)(4-(4-methoxyphenyl)piperazin-1-yl)methyl)-N-cyclopentylbenzamide (Compound 5);
2-((4-(benzyloxy)-3-fluorophenyl)(4-(4-methoxyphenyl)piperazin-1-yl)methyl)-4-chlorophenol (Compound 6);
2-((4-(2,3-dichlorophenyl)piperazin-1-yl)(o-tolyl)methyl)phenol (Compound 8);
N-cyclopentyl-3-((4-(2,3-dichlorophenyl)piperazin-1-yl)(2-hydroxyphenyl)methyl) benzamide (Compound 9, NPB);
2-((4-(benzyloxy)-3-fluorophenyl)(4-(2,3-dichlorophenyl)piperazin-1-yl)methyl)phenol (Compound 10);
2-((4-((4-chlorophenyl)(phenyl)methyl)piperazin-1-yl)(phenyl)methyl)phenol (Compound 11);
2-((4-((4-chlorophenyl)(phenyl)methyl)piperazin-1-yl)(p-tolyl)methyl)phenol (Compound 12);
2-(4-chlorophenyl)(4-((4-chlorophenyl)(phenyl)methyl)piperazin-1-yl)methyl)phenol (Compound 13);
2-((4-((4-chlorophenyl)(phenyl)methyl)piperazin-1-yl)(4-ethylphenyl)methyl)phenol (Compound 14);
(4-((4-((4-chlorophenyl)(phenypmethyl)piperazin-1-yl)(2-hydroxyphenyl)methyl)phenyl) (piperidin-1-yl)methanone (Compound 15);
N-cyclopentyl-3-(4-(2,3-dichlorophenyl)piperazin-1-yl)(4-hydroxy-[1,1'-biphenyl]-3-yl)methyl)benzamide (Compound 16);
N-cyclopentyl-3-((4-(2,3-dichlorophenyl)piperazin-1-yl)(4-hydroxy-2'-methyl-[1,1'-biphenyl]-3-yl)methyl)benzamide (Compound 17);
N-cyclopentyl-3-((4-(2,3-dichlorophenyl)piperazin-1-yl)(4-hydroxy-3'-methyl-[1,1'-biphenyl]-3-yl)methyl)benzamide (Compound 18);
N-cyclopentyl-3-((4-(2,3-dichbrophenyl)piperazin-1-yl)(4-hydroxy-4'-methyl-[1,1'-biphenyl]-3-yl)methyl)benzamide (Compound 19);
3-((2'-chloro-4-hydroxy-[1,1'-biphenyl]-3-yl)(4-(2,3-dichlorophenyl)piperazin-1-yl)methyl)-N-cyclopentylbenzamide (Compound 20);
3((3'-chloro-4-hydroxy-[1,1'-biphenyl]-3-yl)(4-(2,3-dichlorophenyl)piperazin-1-yl)methyl)-N-cyclopentylbenzamide (Compound 21);
3-((4'-chloro-4-hydroxy-[1,1'-biphenyl]-3-yl)(4-(2,3-dichlorophenyl)piperazin-1-yl)methyl)-N-cyclopentylbenzamide (Compound 22);
N-cyclopentyl-3-((4-(2,3-dichlorophenyl)piperazin-1-yl)(4'-ethyl-4-hydroxy-[1,1'-biphenyl]-3-yl)methyl)benzamide (Compound 23);
N-cyclopentyl-3-((4-(2,3-dichlorophenyl)piperazin-1-yl)(4-hydroxy-4'-(piperidine-1-carbonyl)-[1,1'-biphenyl]-3-yl)methyl)benzamide (Compound 24);
N-cyclopentyl-3-((4-(2,3-dichlorophenyl)piperazin-1-yl)(4-hydroxy-4'-methoxy-[1,1'-biphenyl]-3-yl)methyl)benzamide (Compound 25);
N-cyclopentyl-3-((4-(2,3-dichlorophenyl)piperazin-1-yl)(2'-ethyl-4-hydroxy-[1,1'-biphenyl]-3-yl)methyl)benzamide (Compound 26);
N-cyclopentyl-3-((4-(2,3-dichlorophenyl)piperazin-1-yl)(2'-fluoro-4-hydroxy-[1,1'-biphenyl]-3-yl)methyl)benzamide (Compound 27);
N-cyclopentyl-3-((4-(2,3-dichlorophenyl)piperazin-1-yl)(3'-fluoro-4-hydroxy-[1,1'-biphenyl]-3-yl)methyl)benzamide (Compound 28);
N-cyclopentyl-3-((4-(2,3-dichlorophenyl)piperazin-1-yl)(4'-fluoro-4-hydroxy-[1,1'-biphenyl]-3-yl)methyl)benzamide (Compound 29);
N-cyclopentyl-3-((4-(2,3-dichlorophenyl)piperazin-1-yl)(4-hydroxy-3'-nitro-[1,1'-biphenyl]-3-yl)methyl)benzamide (Compound 30);
N-cyclopentyl-3-((4-(2,3-dichlorophenyl)piperazin-1-yl)(4-hydroxy-3'-sulfamoyl-[1,1'-biphenyl]-3-yl)methyl)benzamide (Compound 31);
N-cyclopentyl-3-((4-(2,3-dichlorophenyl)piperazin-1-yl)(4-hydroxy-2'-(trifluoromethyl)-[1,1'-biphenyl]-3-yl)methyl)benzamide (Compound 32);
N-cyclopentyl-3-((4-(2,3-dichlorophenyl)piperazin-1-yl)(4-hydroxy-3'-(trifluoromethyl)-[1,1'-biphenyl]-3-yl)methyl)benzamide (Compound 33);
N-cyclopentyl-3-((4-(2,3-dichlorophenyl)piperazin-1-yl)(4-hydroxy-4'-(trifluoromethyl)-[1,1'-biphenyl]-3-yl)methyl)benzamide (Compound 34);
3-((2'-cyano-4-hydroxy-[1,1'-biphenyl]-3-yl)(4-(2,3-dichlorophenyl)piperazin-1-yl)methyl)-N-cyclopentylbenzamide (Compound 35);
3-((3'-cyano-4-hydroxy-[1,1'-biphenyl]-3-yl)(4-(2,3-dichlorophenyl)piperazin-1-yl)methyl)-N-cyclopentylbenzamide (Compound 36)
3-((4'-cyano-4-hydroxy-[1,1'-biphenyl]-3-yl)(4-(2,3-dichlorophenyl)piperazin-1-yl)methyl)-N-cyclopentylbenzamide (Compound 37);
3-((2'-chloro-4-hydroxy-4'-(trifluoromethyl)-[1,1'-biphenyl]-3-yl)(4-(2,3-dichlorophenyl) piperazin-1-yl)methyl)-N-cyclopentylbenzamide (Compound 38);

N-cyclopentyl-3((2',4'-dichloro-4-hydroxy-[1,1'-biphenyl]-3-yl)(4-(2,3-dichlorophenyl) piperazin-1-yl)methyl)benzamide (Compound 39);

3-((4'-chloro-2',4-dihydroxy-[1,1'-biphenyl]-3-yl)(4-(2,3-dichlorophenyl)piperazin-1-yl)methyl)-N-cyclopentyl-benzamide (Compound 40);

3-((4-(4-chlorophenyl)piperazin-1-yl)(2-hydroxyphenyl)methyl)-N-cyclopentylbenzamide (Compound 41, NCK1)

2-((4-chlorophenyl)(4-(2,3-dichlorophenyl)piperazin-1-yl)methyl)phenol (Compound 42, NCK2)

2-((4-(2,3-dichlorophenyl)piperazin-1-yl)(3-methoxyphenyl)methyl)phenol (Compound 43, NCK3)

1-(5-((4-(2,3-dichlorophenyl)piperazin-1-yl)(2-hydroxyphenyl)methyl)thiophen-2-yl)ethanone (Compound 44, NCK4)

2-((4-(2,3-dichlorophenyl)piperazin-1-yl)(naphthalen-1-yl)methyl)phenol (Compound 45, NCK5)

5-((4-(2,3-dichlorophenyl)piperazin-1-yl)(2-hydroxyphenyl)methyl)furan-2-carbaldehyde (Compound 46, NCK6)

2-((4-(2,3-dichlorophenyl)piperazin-1-yl)(2-fluoro-3-methylpyridin-4-yl)methyl)phenol (Compound 47, NCK7)

2-((4-(2,3-dichlorophenyl)piperazin-1-yl)(4-(trifluoromethyl)phenyl)methyl)phenol (Compound 48, NCK8)

2-((6-chloro-5-methylpyridin-3-yl)(4-(2,3-dichlorophenyl)piperazin-1-yl)methyl)phenol (Compound 49, NCK9)

2-((4-(2,3-dichlorophenyl)piperazin-1-yl)(pyridin-3-yl)methyl)phenol (Compound 50, NCK10)

1-(5-((4-(4-chlorophenyl)piperazin-1-yl)(2-hydroxyphenyl)methyl)thiophen-2-yl)ethanone (Compound 51, NCK14)

3-((4-(4-chlorophenyl)piperazin-1-yl)(4-(diethylamino)-2-hydroxyphenyl)methyl)-N-cyclopentylbenzamide (Compound 52, NCK16)

N-cyclopentyl-3-((4-(2,3-dichlorophenyl)piperazin-1-yl)(4-(diethylamino)-2-hydroxyphenyl)methyl)benzamide (Compound 53, NCK18)

N-cyclopentyl-3-((4-(2,3-dichlorophenyl)piperazin-1-yl)(2-hydroxy-4,6-dimethoxyphenyl)methyl)benzamide (Compound 54, NCK19)

2-((4-chlorophenyl)(4-(4-chlorophenyl)piperazin-1-yl)methyl)phenol (Compound 55, NCK20)

2-((4-(4-chlorophenyl)piperazin-1-yl)(6-methylpyridin-3-yl)methyl)phenol (Compound 56, NCK21)

2-(o-tolyl(4-(p-tolyl)piperazin-1-yl)methyl)phenol (Compound 57, SG1)

2-((4-(p-tolyl)piperazin-1-yl)(4-(trifluoromethyl)phenyl)methyl)phenol (Compound 58, SG2)

N-cyclopentyl-4-((2-hydroxyphenyl)(4-(p-tolyl)piperazin-1-yl)methyl)benzamide (Compound 59, SG3)

2-((4-chlorophenyl)(4-(p-tolyl)piperazin-1-yl)methyl)phenol (Compound 60, SG4)

2-((3-methoxyphenyl)(4-(p-tolyl)piperazin-1-yl)methyl)phenol (Compound 61, SG5)

5-((2-hydroxyphenyl)(4-(p-tolyl)piperazin-1-yl)methyl)furan-2-carbaldehyde (Compound 62, SG6)

2-((6-methylpyridin-3-yl)(4-(p-tolyl)piperazin-1-yl)methyl)phenol (Compound 63, SG7);

or a pharmaceutically acceptable salt, solvate or hydrate thereof or a deuterated or tritiated variant thereof, including all stereoisomers.

15. A pharmaceutical composition comprising a compound according to claim 1 and a pharmaceutically acceptable excipient.

16. A pharmaceutical composition according to claim 15 which is formulated for intraperitoneal administration, hepatoportal administration, intravenous administration, intra articular administration, pancreatic duodenal artery administration, intramuscular administration, or any combination thereof.

17. A method for the treatment of cancer, the method comprising administering to a patient in need of such treatment an effective amount of a compound according to claim 1, wherein the cancer is breast cancer, endometrial cancer, ovarian cancer, liver cancer, colon cancer, prostate cancer or pancreatic cancer.

18. The method according to claim 17, wherein the cancer is a cancer in which there is BAD phosphorylation.

* * * * *

UNITED STATES PATENT AND TRADEMARK OFFICE
CERTIFICATE OF CORRECTION

PATENT NO. : 11,292,773 B2
APPLICATION NO. : 16/605630
DATED : April 5, 2022
INVENTOR(S) : Peter Edward Lobie et al.

It is certified that error appears in the above-identified patent and that said Letters Patent is hereby corrected as shown below:

In the Claims

At Column 57, Line 4, "—$C_{14}$ alkyl" should be -- —$C_{1-4}$ alkyl --.

At Column 57, Line 62, "—$O_{1-4}$ haloalkyl)" should be -- -O($C_{1-4}$ haloalkyl) --.

At Column 63, Line 62, "(4-((4-((4-chlorophenyl)(phenypmethyl)piperazin-1-yl)" should be -- (4-((4-((4-chlorophenyl)(phenyl)methyl)piperazin-1-yl) --.

At Column 63, Line 65, "N-cyclopentyl-3-(4-(2,3-dichlorophenyl)piperazin-1-yl)" should be -- N-cyclopentyl-3-((4-(2,3-dichlorophenyl)piperazin-1-yl) --.

At Column 64, Line 7, "N-cyclopentyl-3-((4-(2,3-dichbrophenyl)piperazin-1-yl)" should be -- N-cyclopentyl-3-((4-(2,3-dichlorophenyl)piperazin-1-yl) --.

At Column 64, Line 14, "3((3'-chloro-4-hydroxy-" should be -- 3-((3'-chloro-4-hydroxy- --.

At Column 64, Line 61, "36)" should be -- 36); --.

At Column 65, Line 1, "N-cyclopentyl-3((2',4'-dichloro-4-hydroxy-[1, 1 '-biphe" should be -- N-cyclopentyl-3-((2',4'-dichloro-4-hydroxy-[1, 1 '-biphe --.

At Column 65, Line 9, "NCK1)" should be -- NCK1); --.

At Column 65, Line 11, "NCK2)" should be -- NCK2); --.

At Column 65, Line 13, "NCK3)" should be -- NCK3); --.

At Column 65, Line 16, "NCK4)" should be -- NCK4); --.

Signed and Sealed this
Thirteenth Day of August, 2024

Katherine Kelly Vidal
*Director of the United States Patent and Trademark Office*

CERTIFICATE OF CORRECTION (continued)
U.S. Pat. No. 11,292,773 B2

At Column 65, Line 18, "NCK5)" should be -- NCK5); --.

At Column 65, Line 22, "NCK6)" should be -- NCK6); --.

At Column 65, Line 25, "NCK7)" should be -- NCK7); --.

At Column 65, Line 27, "NCK8)" should be -- NCK8); --.

At Column 65, Line 30, "NCK9)" should be -- NCK9); --.

At Column 65, Line 32, "NCK10)" should be -- NCK10); --.

At Column 65, Line 35, "NCK14)" should be -- NCK14); --.

At Column 65, Line 38, "NCK16)" should be -- NCK16); --.

At Column 65, Line 41, "NCK18)" should be -- NCK18); --.

At Column 66, Line 3, "NCK19)" should be -- NCK19); --.

At Column 66, Line 5, "NCK20)" should be -- NCK20); --.

At Column 66, Line 7, "NCK21)" should be -- NCK21); --.

At Column 66, Line 9, "SG1)" should be -- SG1); --.

At Column 66, Line 11, "SG2)" should be -- SG2); --.

At Column 66, Line 13, "SG3)" should be -- SG3); --.

At Column 66, Line 15, "SG4)" should be -- SG4); --.

At Column 66, Line 17, "SG5)" should be -- SG5); --.

At Column 66, Line 19, "SG6)" should be -- SG6); --.